US012571032B2

(12) United States Patent
Ayer et al.

(10) Patent No.: US 12,571,032 B2
(45) Date of Patent: *Mar. 10, 2026

(54) POLYMERASE-TEMPLATE COMPLEXES

(71) Applicant: Roche Sequencing Solutions, Inc., Pleasanton, CA (US)

(72) Inventors: Aruna Ayer, Santa Clara, CA (US); Preethi Sarvabhowman, Santa Clara, CA (US); Charles Schwab, San Ramon, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 272 days.

This patent is subject to a terminal disclaimer.

(21) Appl. No.: 17/313,640

(22) Filed: May 6, 2021

(65) Prior Publication Data

US 2021/0277462 A1 Sep. 9, 2021

Related U.S. Application Data

(63) Continuation of application No. 16/505,496, filed on Jul. 8, 2019, now Pat. No. 11,034,999, which is a continuation of application No. 15/444,042, filed on Feb. 27, 2017, now abandoned.

(60) Provisional application No. 62/406,431, filed on Oct. 11, 2016, provisional application No. 62/301,607, filed on Feb. 29, 2016.

(51) Int. Cl.
| | |
|---|---|
| *C12Q 1/6869* | (2018.01) |
| *C12N 9/12* | (2006.01) |
| *C12N 9/96* | (2006.01) |
| *C12Q 1/6806* | (2018.01) |

(52) U.S. Cl.
CPC ......... *C12Q 1/6869* (2013.01); *C12N 9/1252* (2013.01); *C12N 9/96* (2013.01); *C12Q 1/6806* (2013.01); *C12Y 207/07007* (2013.01)

(58) Field of Classification Search
CPC .. C12Q 1/6869; C12Q 1/6806; C12Q 1/6809; C12N 9/1252
See application file for complete search history.

(56) References Cited

U.S. PATENT DOCUMENTS

2016/0222363 A1* 8/2016 Ayer .................... C12N 9/1252

OTHER PUBLICATIONS

Volozhantsev, N.V. et al., Molecular Characterization of Podoviral Bacteriophages Virulent for Clostridium perfringesns and Their Comparison with Members of the Picovirinae, Plos One, vol. 7, e38283, pp. 1-12 (Year: 2012).*

* cited by examiner

*Primary Examiner* — Gary Benzion
*Assistant Examiner* — Lisa Horth
(74) *Attorney, Agent, or Firm* — Charney IP Law LLC; Thomas M. Finetti

(57) ABSTRACT

The present disclosure provides methods and compositions for enhancing the processivity of a polymerase in catalyzing template-dependent DNA synthesis in high concentrations of salt. Also disclosed are methods and compositions for enhancing the assembly of polymerase-template complex compatible with active DNA synthesis in the presence of low levels of nucleotides and at a high temperature, such as temperatures at or near the melting temperature of the polymerase.

21 Claims, 14 Drawing Sheets
Specification includes a Sequence Listing.

ASSOCIATION KINETICS OF POL-TEMPLATE

- POL BINDS TEMPLATE TO SATURATION AT 75-300mM Kglu IN 30MIN IN THE ABSENCE OF NUCLEOTIDES.
- NUCLEOTIDES INTERFERE WITH POL-TEMPLATE SATURATION AT 300mM KGlu.

| | 0X | 1X | 2X | 4X | 6X | 8X | 1X |
|---|---|---|---|---|---|---|---|
| FLUOROPHORE-QUENCHER | | | | | | | |
| ONLY FLUOROPHORE | | | | | | | |

| BINDING CONDITION | 0 MIN | 10 MIN | 20 MIN | 40 MIN | 60 MIN | 90 MIN | 120 MIN | 180 MIN |
|---|---|---|---|---|---|---|---|---|
| 1.2uM dNpCpp/3mM Sr | | | | | | | | |
| 1.2uM dNpCpp | | | | | | | | |
| 1.2uM HEXAS | | | | | | | | |
| NO NUCS / Sr | | | | | | | | |

SEQUENCE LISTING

<160> NUMBER OF SEQ ID NOS: 22

<210> SEQ ID NO 1
<211> LENGTH: 727
<212> TYPE: PRT
<213> ORGANISM: Clostridium phage phiCPV4

<400> SEQUENCE: 1

-continued

```
Met Asp Lys His Thr Gln Tyr Val Lys Glu His Ser Phe Asn Tyr Asp
1               5               10                  15

Glu Tyr Lys Lys Ala Asn Phe Asp Lys Ile Glu Cys Leu Ile Phe Asp
            20                  25                  30

Thr Glu Ser Cys Thr Asn Tyr Glu Asn Asp Asn Thr Gly Ala Arg Val
            35                  40                  45

Tyr Gly Trp Gly Leu Gly Val Thr Arg Asn His Asn Met Ile Tyr Gly
    50                  55                  60

Gln Asn Leu Asn Gln Phe Trp Glu Val Cys Gln Asn Ile Phe Asn Asp
65                  70                  75                  80

Trp Tyr His Asp Asn Lys His Thr Ile Lys Ile Thr Lys Thr Lys Lys
                85                  90                  95

Gly Phe Pro Lys Arg Lys Tyr Ile Lys Phe Pro Ile Ala Val His Asn
            100                 105                 110

Leu Gly Trp Asp Val Glu Phe Leu Lys Tyr Ser Leu Val Glu Asn Gly
            115                 120                 125

Phe Asn Tyr Asp Lys Gly Leu Leu Lys Thr Val Phe Ser Lys Gly Ala
    130                 135                 140

Pro Tyr Gln Thr Val Thr Asp Val Glu Glu Pro Lys Thr Phe His Ile
145                 150                 155                 160

Val Gln Asn Asn Asn Ile Val Tyr Gly Cys Asn Val Tyr Met Asp Lys
                165                 170                 175

Phe Phe Glu Val Glu Asn Lys Asp Gly Ser Thr Thr Glu Ile Gly Leu
            180                 185                 190

Cys Leu Asp Phe Phe Asp Ser Tyr Lys Ile Ile Thr Cys Ala Glu Ser
            195                 200                 205

Gln Phe His Asn Tyr Val His Asp Val Asp Pro Met Phe Tyr Lys Met
    210                 215                 220

Gly Glu Glu Tyr Asp Tyr Asp Thr Trp Arg Ser Pro Thr His Lys Gln
225                 230                 235                 240

Thr Thr Leu Glu Leu Arg Tyr Gln Tyr Asn Asp Ile Tyr Met Leu Arg
            245                 250                 255

Glu Val Ile Glu Gln Phe Tyr Ile Asp Gly Leu Cys Gly Gly Glu Leu
            260                 265                 270

Pro Leu Thr Gly Met Arg Thr Ala Ser Ser Ile Ala Phe Asn Val Leu
            275                 280                 285

Lys Lys Met Thr Phe Gly Glu Glu Lys Thr Glu Glu Gly Tyr Ile Asn
    290                 295                 300

Tyr Phe Glu Leu Asp Lys Lys Thr Lys Phe Glu Phe Leu Arg Lys Arg
305                 310                 315                 320

Ile Glu Met Glu Ser Tyr Thr Gly Gly Tyr Thr His Ala Asn His Lys
            325                 330                 335

Ala Val Gly Lys Thr Ile Asn Lys Ile Gly Cys Ser Leu Asp Ile Asn
            340                 345                 350

Ser Ser Tyr Pro Ser Gln Met Ala Tyr Lys Val Phe Pro Tyr Gly Lys
    355                 360                 365

Pro Val Arg Lys Thr Trp Gly Arg Lys Pro Lys Thr Glu Lys Asn Glu
    370                 375                 380

Val Tyr Leu Ile Glu Val Gly Phe Asp Phe Val Glu Pro Lys His Glu
385                 390                 395                 400

Glu Tyr Ala Leu Asp Ile Phe Lys Ile Gly Ala Val Asn Ser Lys Ala
            405                 410                 415
```

-continued

```
Leu Ser Pro Ile Thr Gly Ala Val Ser Gly Gln Glu Tyr Phe Cys Thr
            420             425                 430

Asn Ile Lys Asp Gly Lys Ala Ile Pro Val Tyr Lys Glu Leu Lys Asp
            435             440                 445

Thr Lys Leu Thr Thr Asn Tyr Asn Val Val Leu Thr Ser Val Glu Tyr
            450             455                 460

Glu Phe Trp Ile Lys His Phe Asn Phe Gly Val Phe Lys Lys Asp Glu
465                 470             475                 480

Tyr Asp Cys Phe Glu Val Asp Asn Leu Glu Phe Thr Gly Leu Lys Ile
                485             490                 495

Gly Ser Ile Leu Tyr Tyr Lys Ala Glu Lys Gly Lys Phe Lys Pro Tyr
            500             505                 510

Val Asp His Phe Thr Lys Met Lys Val Glu Asn Lys Lys Leu Gly Asn
            515             520                 525

Lys Pro Leu Thr Asn Gln Ala Lys Leu Ile Leu Asn Gly Ala Tyr Gly
            530             535                 540

Lys Phe Gly Thr Lys Gln Asn Lys Glu Glu Lys Asp Leu Ile Met Asp
545                 550             555                 560

Lys Asn Gly Leu Leu Thr Phe Thr Gly Ser Val Thr Glu Tyr Glu Gly
                565             570                 575

Lys Glu Phe Tyr Arg Pro Tyr Ala Ser Phe Val Thr Ala Tyr Gly Arg
            580             585                 590

Leu Gln Leu Trp Asn Ala Ile Ile Tyr Ala Val Gly Val Glu Asn Phe
            595             600                 605

Leu Tyr Cys Asp Thr Asp Ser Ile Tyr Cys Asn Arg Glu Val Asn Ser
            610             615                 620

Leu Ile Glu Asp Met Asn Ala Ile Gly Glu Thr Ile Asp Lys Thr Ile
625                 630             635                 640

Leu Gly Lys Trp Asp Val Glu His Val Phe Asp Lys Phe Lys Val Leu
                645             650                 655

Gly Gln Lys Lys Tyr Met Tyr His Asp Cys Lys Glu Asp Lys Thr Asp
            660             665                 670

Leu Lys Cys Cys Gly Leu Pro Ser Asp Ala Arg Lys Ile Ile Ile Gly
            675             680                 685

Gln Gly Phe Asp Glu Phe Tyr Leu Gly Lys Asn Val Glu Gly Lys Lys
            690             695                 700

Gln Arg Lys Lys Val Ile Gly Gly Cys Leu Leu Leu Asp Thr Leu Phe
705                 710             715                 720

Thr Ile Lys Lys Ile Met Phe
                725
```

```
<210> SEQ ID NO 2
<211> LENGTH: 739
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met His His His His His His His Ser Gly Gly Ser Asp Lys His
1                 5                 10                  15

Thr Gln Tyr Val Lys Glu His Ser Phe Asn Tyr Asp Glu Tyr Lys Lys
            20              25                  30

Ala Asn Phe Asp Lys Ile Glu Cys Leu Ile Phe Asp Thr Glu Ser Cys
            35              40                  45
```

```
Thr Asn Tyr Glu Asn Asp Asn Thr Gly Ala Arg Val Tyr Gly Trp Gly
    50              55              60

Leu Gly Val Thr Arg Asn His Asn Met Ile Tyr Gly Gln Asn Leu Asn
65              70              75              80

Gln Phe Trp Glu Val Cys Gln Asn Ile Phe Asn Asp Trp Tyr His Asp
            85              90              95

Asn Lys His Thr Ile Lys Ile Thr Lys Thr Lys Lys Gly Phe Pro Lys
            100             105             110

Arg Lys Tyr Ile Lys Phe Pro Ile Ala Val His Asn Leu Gly Trp Asp
        115             120             125

Val Glu Phe Leu Lys Tyr Ser Leu Val Glu Asn Gly Phe Asn Tyr Asp
    130             135             140

Lys Gly Leu Leu Lys Thr Val Phe Ser Lys Gly Ala Pro Tyr Gln Thr
145             150             155             160

Val Thr Asp Val Glu Glu Pro Lys Thr Phe His Ile Val Gln Asn Asn
            165             170             175

Asn Ile Val Tyr Gly Cys Asn Val Tyr Met Asp Lys Phe Phe Glu Val
            180             185             190

Glu Asn Lys Asp Gly Ser Thr Thr Glu Ile Gly Leu Cys Leu Asp Phe
        195             200             205

Phe Asp Ser Tyr Lys Ile Ile Thr Cys Ala Glu Ser Gln Phe His Asn
    210             215             220

Tyr Val His Asp Val Asp Pro Met Phe Tyr Lys Met Gly Glu Glu Tyr
225             230             235             240

Asp Tyr Asp Thr Trp Arg Ser Pro Thr His Lys Gln Thr Thr Leu Glu
            245             250             255

Leu Arg Tyr Gln Tyr Asn Asp Ile Tyr Met Leu Arg Glu Val Ile Glu
            260             265             270

Gln Phe Tyr Ile Asp Gly Leu Cys Gly Gly Glu Leu Pro Leu Thr Gly
        275             280             285

Met Arg Thr Ala Ser Ser Ile Ala Phe Asn Val Leu Lys Lys Met Thr
    290             295             300

Phe Gly Glu Glu Lys Thr Glu Glu Gly Tyr Ile Asn Tyr Phe Glu Leu
305             310             315             320

Asp Lys Lys Thr Lys Phe Glu Phe Leu Arg Lys Arg Ile Glu Met Glu
            325             330             335

Ser Tyr Thr Gly Gly Tyr Thr His Ala Asn His Lys Ala Val Gly Lys
            340             345             350

Thr Ile Asn Lys Ile Gly Cys Ser Leu Asp Ile Asn Ser Ser Tyr Pro
        355             360             365

Ser Gln Met Ala Tyr Lys Val Phe Pro Tyr Gly Lys Pro Val Arg Lys
    370             375             380

Thr Trp Gly Arg Lys Pro Lys Thr Glu Lys Asn Glu Val Tyr Leu Ile
385             390             395             400

Glu Val Gly Phe Asp Phe Val Glu Pro Lys His Glu Glu Tyr Ala Leu
            405             410             415

Asp Ile Phe Lys Ile Gly Ala Val Asn Ser Lys Ala Leu Ser Pro Ile
            420             425             430

Thr Gly Ala Val Ser Gly Gln Glu Tyr Phe Cys Thr Asn Ile Lys Asp
        435             440             445

Gly Lys Ala Ile Pro Val Tyr Lys Glu Leu Lys Asp Thr Lys Leu Thr
    450             455             460
```

-continued

```
Thr Asn Tyr Asn Val Val Leu Thr Ser Val Glu Tyr Glu Phe Trp Ile
465                 470                 475                 480

Lys His Phe Asn Phe Gly Val Phe Lys Lys Asp Glu Tyr Asp Cys Phe
                485                 490                 495

Glu Val Asp Asn Leu Glu Phe Thr Gly Leu Lys Ile Gly Ser Ile Leu
            500                 505                 510

Tyr Tyr Lys Ala Glu Lys Gly Lys Phe Lys Pro Tyr Val Asp His Phe
        515                 520                 525

Thr Lys Met Lys Val Glu Asn Lys Lys Leu Gly Asn Lys Pro Leu Thr
    530                 535                 540

Asn Gln Ala Lys Leu Ile Leu Asn Gly Ala Tyr Gly Lys Phe Gly Thr
545                 550                 555                 560

Lys Gln Asn Lys Glu Glu Lys Asp Leu Ile Met Asp Lys Asn Gly Leu
                565                 570                 575

Leu Thr Phe Thr Gly Ser Val Thr Glu Tyr Glu Gly Lys Glu Phe Tyr
            580                 585                 590

Arg Pro Tyr Ala Ser Phe Val Thr Ala Tyr Gly Arg Leu Gln Leu Trp
        595                 600                 605

Asn Ala Ile Ile Tyr Ala Val Gly Val Glu Asn Phe Leu Tyr Cys Asp
    610                 615                 620

Thr Asp Ser Ile Tyr Cys Asn Arg Glu Val Asn Ser Leu Ile Glu Asp
625                 630                 635                 640

Met Asn Ala Ile Gly Glu Thr Ile Asp Lys Thr Ile Leu Gly Lys Trp
                645                 650                 655

Asp Val Glu His Val Phe Asp Lys Phe Lys Val Leu Gly Gln Lys Lys
            660                 665                 670

Tyr Met Tyr His Asp Cys Lys Glu Asp Lys Thr Asp Leu Lys Cys Cys
        675                 680                 685

Gly Leu Pro Ser Asp Ala Arg Lys Ile Ile Ile Gly Gln Gly Phe Asp
    690                 695                 700

Glu Phe Tyr Leu Gly Lys Asn Val Glu Gly Lys Lys Gln Arg Lys Lys
705                 710                 715                 720

Val Ile Gly Gly Cys Leu Leu Leu Asp Thr Leu Phe Thr Ile Lys Lys
                725                 730                 735

Ile Met Phe
```

<210> SEQ ID NO 3
<211> LENGTH: 2220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atgcatcacc atcatcatca ccaccacagc ggcggttccg acaaacacac gcagtacgtc       60
aaagagcata gcttcaatta tgacgagtat aagaaagcga atttcgacaa gatcgagtgc      120
ctgatctttg acaccgagag ctgcacgaat tatgagaacg ataataccgg tgcacgtgtt      180
tacggttggg gtcttggcgt cacccgcaac acaatatga tctacggcca aaatctgaat       240
cagttttggg aagtatgcca gaacattttc aatgattggt atcacgacaa caaacatacc      300
attaagatta ccaagaccaa gaaaggcttc ccgaaacgta agtacattaa gtttccgatt      360
gcagttcaca atttgggctg ggatgttgaa ttcctgaagt atagcctggt ggagaatggt      420
ttcaattacg acaagggtct gctgaaaact gttttttagca agggtgcgcc gtaccaaacc      480
```

```
gtgaccgatg ttgaggaacc gaaaacgttc catatcgtcc agaataacaa catcgtttat    540
ggttgtaacg tgtatatgga caaattcttt gaggtcgaga caaagacgg  ctctaccacc    600 gagattggcc tgtgcttgga tttcttcgat agctataaga tcatcacgtg tgctgagagc    660
cagttccaca attacgttca tgatgtggat ccaatgttct acaaatgggt tgaagagtat    720
gattacgata cttggcgtag cccgacgcac aagcagacca ccctggagct gcgctaccaa    780
tacaatgata tctatatgct gcgtgaagtc atcgaacagt tttacattga cggtttatgt    840
ggcggcgagc tgccgctgac cggcatgcgc accgcttcca gcattgcgtt caacgtgctg    900
aaaaagatga cctttggtga ggaaaagacg gaagagggct acatcaacta ttttgaattg    960
gacaagaaaa ccaaattcga gtttctgcgt aagcgcattg aaatggaatc gtacaccggt   1020
ggctatacgc acgcaaatca caagccgtt  ggtaagacta ttaacaagat cggttgctct   1080
ttggacatta acagctcata cccttcgcag atggcgtaca aggtctttcc gtatggcaaa   1140
ccggttcgta agacctgggg tcgtaaacca aagaccgaga agaacgaagt ttatctgatt   1200
gaagttggct ttgacttcgt ggagccgaaa cacgaagaat acgcgctgga tatctttaag   1260
attggtgcgg tgaactctaa agcgctgagc ccgatcaccg gcgctgtcag cggtcaagag   1320
tatttctgta cgaacattaa agacggcaaa gcaatcccgg tttacaaaga actgaaggac   1380
accaaattga ccactaacta caatgtcgtg ctgaccagcg tggagtacga gttctggatc   1440
aaacacttca attttggtgt gtttaagaaa gacgagtacg actgtttcga agttgacaat   1500 ctggagtttta cgggtctgaa gattggttcc attctgtact acaaggcaga gaaaggcaag   1560
tttaaacctt acgtggatca cttcacgaaa atgaaagtgg agaacaagaa actgggtaat   1620
aagccgctga cgaatcaggc aaagctgatt ctgaacggtg cgtacggcaa attcggcacc   1680
aaacaaaaca agaagagaa  agatttgatc atggataaga acggtttgct gaccttcacg   1740
ggtagcgtca cggaatacga gggtaaagaa ttctatcgtc cgtatgcgag cttcgttact   1800
gcctatggtc gcctgcaact gtggaacgcg attatctacg cggttggtgt ggagaatttt   1860
ctgtactgcg acaccgacag catctattgt aaccgtgaag ttaacagcct cattgaggat   1920
atgaacgcca ttggtgaaac catcgataaa acgattctgg gtaaatggga cgtggagcat   1980
gtctttgata agtttaaggt cctgggccag aagaagtaca tgtatcatga ttgcaaagaa   2040
gataaaacgg acctgaagtg ttgcggtctg ccgagcgatg cccgtaagat tatcattggt   2100
caaggtttcg acgagttta  tctgggcaaa aatgtcgaag gtaagaagca acgcaaaaaa   2160
gtgatcggcg gttgcctgct gctggacacc ctgtttacga tcaagaaaat catgttctaa   2220
```

```
<210> SEQ ID NO 4
<211> LENGTH: 869
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met His His His His His His His Ser Gly Asp Tyr Asp Ile Pro
1               5                   10                  15

Thr Thr Glu Asn Leu Tyr Phe Gln Gly Ala Met Val Asp Thr Leu Ser
            20                  25                  30

Gly Leu Ser Ser Glu Gln Gly Gln Ser Gly Asp Met Thr Ile Glu Glu
        35                  40                  45
```

-continued

```
Asp Ser Ala Thr His Ile Lys Phe Ser Lys Arg Asp Glu Asp Gly Lys
    50                  55                  60

Glu Leu Ala Gly Ala Thr Met Glu Leu Arg Asp Ser Ser Gly Lys Thr
65                  70                  75                  80

Ile Ser Thr Trp Ile Ser Asp Gly Gln Val Lys Asp Phe Tyr Leu Tyr
                85                  90                  95

Pro Gly Lys Tyr Thr Phe Val Glu Thr Ala Ala Pro Asp Gly Tyr Glu
            100                 105                 110

Val Ala Thr Ala Ile Thr Phe Thr Val Asn Glu Gln Gly Gln Val Thr
            115                 120                 125

Val Asn Gly Lys Ala Thr Lys Gly Asp Ala His Ile Gly Gly Ser Asp
    130                 135                 140

Lys His Thr Gln Tyr Val Lys Glu His Ser Phe Asn Tyr Asp Glu Tyr
145                 150                 155                 160

Lys Lys Ala Asn Phe Asp Lys Ile Glu Cys Leu Ile Phe Ala Thr Glu
                165                 170                 175

Ser Cys Thr Asn Tyr Glu Asn Asp Asn Thr Gly Ala Arg Val Tyr Gly
            180                 185                 190

Trp Gly Leu Gly Val Thr Arg Asn His Asn Met Ile Tyr Gly Gln Asn
            195                 200                 205

Leu Asn Gln Phe Trp Glu Val Cys Gln Asn Ile Phe Asn Asp Trp Tyr
    210                 215                 220

His Asp Asn Lys His Thr Ile Lys Ile Thr Lys Thr Lys Lys Gly Phe
225                 230                 235                 240

Pro Lys Arg Lys Tyr Ile Lys Phe Pro Ile Ala Val His Asn Leu Gly
                245                 250                 255

Trp Asp Val Glu Phe Leu Lys Tyr Ser Leu Val Glu Asn Gly Phe Asn
            260                 265                 270

Tyr Asp Lys Gly Leu Leu Lys Thr Val Phe Ser Lys Gly Ala Pro Tyr
            275                 280                 285

Gln Thr Val Thr Asp Val Glu Glu Pro Lys Thr Phe His Ile Val Gln
    290                 295                 300

Asn Asn Asn Ile Val Tyr Gly Cys Asn Val Tyr Met Asp Lys Phe Phe
305                 310                 315                 320

Glu Val Glu Asn Lys Asp Gly Ser Thr Thr Glu Ile Gly Leu Cys Leu
                325                 330                 335

Asp Phe Phe Asp Ser Tyr Lys Ile Ile Thr Cys Ala Glu Ser Gln Phe
            340                 345                 350

His Asn Tyr Val His Asp Val Asp Pro Met Phe Tyr Lys Met Gly Glu
            355                 360                 365

Glu Tyr Asp Tyr Asp Thr Trp Arg Ser Pro Thr His Lys Gln Thr Thr
    370                 375                 380

Leu Glu Leu Arg Tyr Gln Tyr Asn Asp Ile Tyr Met Leu Arg Glu Val
385                 390                 395                 400

Ile Glu Gln Phe Tyr Ile Asp Gly Leu Cys Gly Gly Glu Leu Pro Leu
                405                 410                 415

Thr Gly Met Arg Thr Ala Ser Ser Ile Ala Phe Asn Val Leu Lys Lys
            420                 425                 430

Met Thr Phe Gly Glu Glu Lys Thr Glu Glu Gly Tyr Ile Asn Tyr Phe
            435                 440                 445

Glu Leu Asp Lys Lys Thr Lys Phe Glu Phe Leu Arg Lys Arg Ile Glu
    450                 455                 460

Met Glu Ser Tyr Thr Gly Gly Tyr Thr His Ala Asn His Lys Ala Val
```

-continued

```
465                470                475                480
Gly Lys Thr Ile Asn Lys Ile Gly Cys Ser Leu Asp Ile Asn Ser Ala
                485                490                495

Tyr Pro Ser Gln Met Ala Tyr Lys Val Phe Pro Tyr Gly Lys Pro Val
            500                505                510

Arg Lys Thr Trp Gly Arg Lys Pro Lys Thr Glu Lys Asn Glu Val Tyr
            515                520                525

Leu Ile Glu Val Gly Phe Asp Phe Val Glu Pro Lys His Glu Glu Tyr
            530                535                540

Ala Leu Asp Ile Phe Lys Ile Gly Ala Val Asn Ser Lys Ala Leu Ser
545                550                555                560

Pro Ile Thr Gly Ala Val Ser Gly Gln Glu Tyr Phe Cys Thr Asn Ile
                565                570                575

Lys Asp Gly Lys Ala Ile Pro Val Tyr Lys Glu Leu Lys Asp Thr Lys
                580                585                590

Leu Thr Thr Asn Tyr Asn Val Val Leu Thr Ser Val Glu Tyr Glu Phe
            595                600                605

Trp Ile Lys His Phe Asn Phe Gly Val Phe Lys Lys Asp Glu Tyr Asp
            610                615                620

Cys Phe Glu Val Asp Asn Leu Glu Phe Thr Gly Leu Lys Ile Gly Ser
625                630                635                640

Ile Leu Tyr Tyr Lys Ala Glu Lys Gly Lys Phe Lys Pro Tyr Val Asp
                645                650                655

His Phe Met Lys Met Lys Val Glu Asn Lys Lys Leu Gly Asn Lys Pro
                660                665                670

Leu Thr Asn Gln Phe Lys Leu Ile Leu Asn Gly Ala Tyr Gly Lys Phe
            675                680                685

Gly Thr Lys Gln Asn Lys Glu Glu Lys Asp Leu Ile Met Asp Lys Asn
            690                695                700

Gly Leu Leu Thr Phe Thr Gly Ser Val Thr Glu Tyr Glu Gly Lys Glu
705                710                715                720

Phe Tyr Arg Pro Tyr Ala Ser Phe Val Thr Ala Tyr Gly Arg Leu Gln
                725                730                735

Leu Trp Asn Ala Ile Ile Tyr Ala Val Gly Val Glu Asn Phe Leu Tyr
                740                745                750

Cys Asp Thr Asp Ser Ile Tyr Cys Asn Arg Glu Val Asn Ser Leu Ile
            755                760                765

Glu Asp Met Asn Ala Ile Gly Glu Thr Ile Asp Lys Thr Ile Leu Gly
            770                775                780

Lys Trp Asp Val Glu His Val Phe Asp Lys Phe Lys Val Leu Gly Gln
785                790                795                800

Lys Lys Tyr Met Tyr His Asp Cys Lys Glu Asp Lys Thr Asp Leu Lys
                805                810                815

Cys Cys Gly Leu Pro Ser Asp Ala Arg Lys Ile Ile Ile Gly Gln Gly
            820                825                830

Phe Asp Glu Phe Tyr Leu Gly Lys Asn Val Glu Gly Lys Lys Gln Arg
            835                840                845

Lys Lys Val Ile Gly Gly Cys Leu Leu Leu Asp Thr Leu Phe Thr Ile
            850                855                860

Lys Lys Ile Met Phe
865
```

<210> SEQ ID NO 5

```
<211> LENGTH: 2610
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgcatcacc atcatcatca ccaccacagc ggtgactacg acatcccgac caccgagaac      60
ctgtacttcc agggcgccat ggtggacaca ctgagcggtc tgagcagtga acagggccag     120
agcggcgaca tgaccattga agaggacagc gccacccaca tcaagttcag caagcgtgac     180
gaggacggta aggaactggc cggcgccacc atggaactgc gtgacagcag cggcaagacc     240
atcagcacct ggatcagcga tggccaggtg aaggacttct acctgtaccc gggcaagtac     300
accttcgtgg agacagccgc accggacggt tacgaggttg ccaccgccat caccttcacc     360
gtgaacgagc agggccaagt gaccgttaac ggcaaggcca ccagggtga cgcccacatc      420 ggcggttccg acaaacacac gcagtacgtc aaagagcata gcttcaatta tgacgagtat     480
aagaaagcga atttcgacaa gatcgagtgc ctgatctttg cgaccgagag ctgcacgaat     540
tatgagaacg ataataccgg tgcacgtgtt tacggttggg gtcttggcgt cacccgcaac     600
cacaatatga tctacggcca aaatctgaat cagttttggg aagtatgcca gaacattttc     660
aatgattggt atcacgacaa caaacatacc attaagatta ccaagaccaa gaaaggcttc     720
ccgaaacgta agtacattaa gtttccgatt gcagttcaca atttgggctg ggatgttgaa     780
ttcctgaagt atagcctggt ggagaatggt ttcaattacg acaagggtct gctgaaaact     840
gtttttagca agggtgcgcc gtaccaaacc gtgaccgatg ttgaggaacc gaaaacgttc     900
catatcgtcc agaataacaa catcgtttat ggttgtaacg tgtatatgga caaattcttt     960
gaggtcgaga acaaagacgg ctctaccacc gagattggcc tgtgcttgga tttcttcgat    1020
agctataaga tcatcacgtg tgctgagagc cagttccaca attacgttca tgatgtggat    1080
ccaatgttct acaaaatggg tgaagagtat gattacgata cttggcgtag cccgacgcac    1140
aagcagacca ccctggagct gcgctaccaa tacaatgata tctatatgct gcgtgaagtc    1200
atcgaacagt tttacattga cggtttatgt ggcggcgagc tgccgctgac cggcatgcgc    1260
accgcttcca gcattgcgtt caacgtgctg aaaaagatga cctttggtga ggaaaagacg    1320
gaagagggct acatcaacta ttttgaattg gacaagaaaa ccaaattcga gtttctgcgt    1380
aagcgcattg aaatggaatc gtacaccggt ggctatacgc acgcaaatca caagccgtt     1440 ggtaagacta ttaacaagat cggttgctct ttggacatta cagcgcgta cccttcgcag     1500 atggcgtaca aggtctttcc gtatggcaaa ccggttcgta agacctgggg tcgtaaacca    1560
aagaccgaga gaacgaagt ttatctgatt gaagttggct ttgacttcgt ggagccgaaa     1620
cacgaagaat acgcgctgga tatctttaag attggtgcgg tgaactctaa agcgctgagc    1680
ccgatcaccg gcgctgtcag cggtcaagag tatttctgta cgaacattaa agacggcaaa    1740
gcaatcccgg tttacaaaga actgaaggac accaaattga ccactaacta caatgtcgtg    1800
ctgaccagcg tggagtacga gttctggatc aaacacttca attttggtgt gtttaagaaa    1860
gacgagtacg actgtttcga agttgacaat ctggagttta cgggtctgaa gattggttcc    1920
attctgtact acaaggcaga gaaaggcaag tttaaacctt acgtggatca cttcatgaaa    1980
atgaaagtgg agaacaagaa actgggtaat aagccgctga cgaatcagtt taagctgatt    2040
ctgaacggtg cgtacggcaa attcggcacc aaacaaaaca agaagagaa agatttgatc      2100
```

-continued

```
atggataaga acggtttgct gaccttcacg ggtagcgtca cggaatacga gggtaaagaa      2160
ttctatcgtc cgtatgcgag cttcgttact gcctatggtc gcctgcaact gtggaacgcg      2220
attatctacg cggttggtgt ggagaatttt ctgtactgcg acaccgacag catctattgt      2280
aaccgtgaag ttaacagcct cattgaggat atgaacgcca ttggtgaaac catcgataaa      2340
acgattctgg gtaaatggga cgtggagcat gtctttgata agtttaaggt cctgggccag      2400
aagaagtaca tgtatcatga ttgcaaagaa gataaaacgg acctgaagtg ttgcggtctg      2460
ccgagcgatg cccgtaagat tatcattggt caaggtttcg acgagtttta tctgggcaaa      2520
aatgtcgaag taagaagca acgcaaaaaa gtgatcggcg gttgcctgct gctggacacc      2580
ctgtttacga tcaagaaaat catgttctaa                                      2610
```

<210> SEQ ID NO 6
<211> LENGTH: 869
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met His His His His His His His Ser Gly Asp Tyr Asp Ile Pro
1               5                   10                  15

Thr Thr Glu Asn Leu Tyr Phe Gln Gly Ala Met Val Asp Thr Leu Ser
            20                  25                  30

Gly Leu Ser Ser Glu Gln Gly Gln Ser Gly Asp Met Thr Ile Glu Glu
            35                  40                  45

Asp Ser Ala Thr His Ile Lys Phe Ser Lys Arg Asp Glu Asp Gly Lys
        50                  55                  60

Glu Leu Ala Gly Ala Thr Met Glu Leu Arg Asp Ser Ser Gly Lys Thr
65                  70                  75                  80

Ile Ser Thr Trp Ile Ser Asp Gly Gln Val Lys Asp Phe Tyr Leu Tyr
                85                  90                  95

Pro Gly Lys Tyr Thr Phe Val Glu Thr Ala Ala Pro Asp Gly Tyr Glu
            100                 105                 110

Val Ala Thr Ala Ile Thr Phe Thr Val Asn Glu Gln Gly Gln Val Thr
            115                 120                 125

Val Asn Gly Lys Ala Thr Lys Gly Asp Ala His Ile Gly Gly Ser Asp
        130                 135                 140

Lys His Thr Gln Tyr Val Lys Glu His Ser Phe Asn Tyr Asp Glu Tyr
145                 150                 155                 160

Lys Lys Ala Asn Phe Asp Lys Ile Glu Cys Leu Ile Phe Ala Thr Glu
                165                 170                 175

Ser Cys Thr Asn Tyr Glu Asn Asp Asn Thr Gly Ala Arg Val Tyr Gly
            180                 185                 190

Trp Gly Leu Gly Val Thr Arg Asn His Asn Met Ile Tyr Gly Gln Asn
            195                 200                 205

Leu Asn Gln Phe Trp Glu Val Cys Gln Asn Ile Phe Asn Asp Trp Tyr
        210                 215                 220

His Asp Asn Lys His Thr Ile Lys Ile Thr Lys Thr Lys Lys Gly Phe
225                 230                 235                 240

Pro Lys Arg Lys Tyr Ile Lys Phe Pro Ile Ala Val His Asn Leu Gly
                245                 250                 255

Trp Asp Val Glu Phe Leu Lys Tyr Ser Leu Val Glu Asn Gly Phe Asn
            260                 265                 270
```

-continued

```
Tyr Asp Lys Gly Leu Leu Lys Thr Val Phe Ser Lys Gly Ala Pro Tyr
    275             280             285

Gln Thr Val Thr Asp Val Glu Glu Pro Lys Thr Phe His Ile Val Gln
    290             295             300

Asn Asn Asn Ile Val Tyr Gly Cys Asn Val Tyr Met Asp Lys Phe Phe
305             310             315             320

Glu Val Glu Asn Lys Asp Gly Ser Thr Thr Glu Ile Gly Leu Cys Leu
            325             330             335

Asp Phe Phe Asp Ser Tyr Lys Ile Ile Thr Cys Ala Glu Ser Gln Phe
            340             345             350

His Asn Tyr Val His Asp Val Asp Pro Met Phe Tyr Lys Met Gly Glu
    355             360             365

Glu Tyr Asp Tyr Asp Thr Trp Arg Ser Pro Thr His Lys Gln Thr Thr
    370             375             380

Leu Glu Leu Arg Tyr Gln Tyr Asn Asp Ile Tyr Met Leu Arg Glu Val
385             390             395             400

Ile Glu Gln Phe Tyr Ile Asp Gly Leu Cys Gly Gly Glu Leu Pro Leu
            405             410             415

Thr Gly Met Arg Thr Ala Ser Ser Ile Ala Phe Asn Val Leu Lys Lys
            420             425             430

Met Thr Phe Gly Glu Glu Lys Thr Glu Glu Gly Tyr Ile Asn Tyr Phe
            435             440             445

Glu Leu Asp Lys Lys Thr Lys Phe Glu Phe Leu Arg Lys Arg Ile Glu
    450             455             460

Met Glu Ser Tyr Thr Gly Gly Tyr Thr His Ala Asn His Lys Ala Val
465             470             475             480

Gly Lys Thr Ile Asn Lys Ile Gly Cys Ser Leu Asp Ile Asn Ser Ala
            485             490             495

Tyr Pro Ser Gln Met Ala Tyr Lys Val Phe Pro Tyr Gly Lys Pro Val
            500             505             510

Arg Lys Thr Trp Gly Arg Lys Pro Lys Thr Glu Lys Asn Glu Val Tyr
            515             520             525

Leu Ile Glu Val Gly Phe Asp Phe Val Glu Pro Lys His Glu Glu Tyr
    530             535             540

Ala Leu Asp Ile Phe Lys Ile Gly Ala Val Asn Ser Lys Ala Leu Ser
545             550             555             560

Pro Ile Thr Gly Ala Val Ser Gly Gln Glu Tyr Phe Cys Thr Asn Ile
            565             570             575

Lys Asp Gly Lys Ala Ile Pro Val Tyr Lys Glu Leu Lys Asp Thr Lys
            580             585             590

Leu Thr Thr Asn Tyr Asn Val Val Leu Thr Ser Val Glu Tyr Glu Phe
            595             600             605

Trp Ile Lys His Phe Asn Phe Gly Val Phe Lys Lys Asp Glu Tyr Asp
    610             615             620

Cys Phe Glu Val Asp Asn Leu Glu Phe Thr Gly Leu Lys Ile Gly Ser
625             630             635             640

Ile Leu Tyr Tyr Lys Ala Glu Lys Gly Lys Phe Lys Pro Tyr Val Asp
            645             650             655

His Phe Met Lys Met Lys Val Glu Asn Lys Lys Leu Gly Asn Lys Pro
            660             665             670

Leu Thr Asn Gln Phe Lys Leu Ile Leu Asn Gly Ala Tyr Gly Lys Phe
    675             680             685
```

Gly Thr Lys Gln Asn Lys Glu Glu Lys Asp Leu Ile Met Asp Lys Asn
    690                 695                 700

Gly Leu Leu Thr Phe Thr Gly Ser Val Thr Lys Tyr Glu Gly Lys Glu
705                 710                 715                 720

Phe Tyr Arg Pro Tyr Ala Ser Phe Val Thr Ala Tyr Gly Arg Leu Gln
                725                 730                 735

Leu Trp Asn Ala Ile Ile Tyr Ala Val Gly Val Glu Asn Phe Leu Tyr
            740                 745                 750

Cys Asp Thr Asp Ser Ile Tyr Cys Asn Arg Glu Val Asn Ser Leu Ile
            755                 760                 765

Glu Asp Met Asn Ala Ile Gly Glu Thr Ile Asp Lys Thr Ile Leu Gly
    770                 775                 780

Lys Trp Asp Val Glu His Val Phe Asp Lys Phe Lys Val Leu Gly Gln
785                 790                 795                 800

Lys Lys Tyr Met Tyr His Asp Cys Lys Glu Asp Lys Thr Asp Leu Lys
                805                 810                 815

Cys Cys Gly Leu Pro Ser Asp Ala Arg Lys Ile Ile Ile Gly Gln Gly
                820                 825                 830

Phe Asp Glu Phe Tyr Leu Gly Lys Asn Val Glu Gly Lys Lys Gln Arg
            835                 840                 845

Lys Lys Val Ile Gly Gly Cys Leu Leu Leu Asp Thr Leu Phe Thr Ile
    850                 855                 860

Lys Lys Ile Met Phe
865

<210> SEQ ID NO 7
<211> LENGTH: 869
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met His His His His His His His Ser Gly Asp Tyr Asp Ile Pro
1               5                   10                  15

Thr Thr Glu Asn Leu Tyr Phe Gln Gly Ala Met Val Asp Thr Leu Ser
                20                  25                  30

Gly Leu Ser Ser Glu Gln Gly Gln Ser Gly Asp Met Thr Ile Glu Glu
            35                  40                  45

Asp Ser Ala Thr His Ile Lys Phe Ser Lys Arg Asp Glu Asp Gly Lys
    50                  55                  60

Glu Leu Ala Gly Ala Thr Met Glu Leu Arg Asp Ser Ser Gly Lys Thr
65                  70                  75                  80

Ile Ser Thr Trp Ile Ser Asp Gly Gln Val Lys Asp Phe Tyr Leu Tyr
                85                  90                  95

Pro Gly Lys Tyr Thr Phe Val Glu Thr Ala Ala Pro Asp Gly Tyr Glu
            100                 105                 110

Val Ala Thr Ala Ile Thr Phe Thr Val Asn Glu Gln Gly Gln Val Thr
        115                 120                 125

Val Asn Gly Lys Ala Thr Lys Gly Asp Ala His Ile Gly Gly Ser Asp
    130                 135                 140

Lys His Thr Gln Tyr Val Lys Glu His Ser Phe Asn Tyr Asp Glu Tyr
145                 150                 155                 160

Lys Lys Ala Asn Phe Asp Lys Ile Glu Cys Leu Ile Phe Ala Thr Glu
                165                 170                 175

```
Ser Cys Thr Asn Tyr Glu Asn Asp Asn Thr Gly Ala Arg Val Tyr Gly
        180                 185                 190

Trp Gly Leu Gly Val Thr Arg Asn His Asn Met Ile Tyr Gly Gln Asn
        195                 200                 205

Leu Asn Gln Phe Trp Glu Val Cys Gln Asn Ile Phe Asn Asp Trp Tyr
        210                 215                 220

His Asp Asn Lys His Thr Ile Lys Ile Thr Lys Thr Lys Lys Gly Phe
225                 230                 235                 240

Pro Lys Arg Lys Tyr Ile Lys Phe Pro Ile Ala Val His Asn Leu Gly
                245                 250                 255

Trp Asp Val Glu Phe Leu Lys Tyr Ser Leu Val Glu Asn Gly Phe Asn
        260                 265                 270

Tyr Asp Lys Gly Leu Leu Lys Thr Val Phe Ser Lys Gly Ala Pro Tyr
        275                 280                 285

Gln Thr Val Thr Asp Val Glu Glu Pro Lys Thr Phe His Ile Val Gln
        290                 295                 300

Asn Asn Asn Ile Val Tyr Gly Cys Asn Val Tyr Met Asp Lys Phe Phe
305                 310                 315                 320

Glu Val Glu Asn Lys Asp Gly Ser Thr Thr Glu Ile Gly Leu Cys Leu
                325                 330                 335

Asp Phe Phe Asp Ser Tyr Lys Ile Ile Thr Cys Ala Glu Ser Gln Phe
                340                 345                 350

His Asn Tyr Val His Asp Val Asp Pro Met Phe Tyr Lys Met Gly Glu
                355                 360                 365

Glu Tyr Asp Tyr Asp Thr Trp Arg Ser Pro Thr His Lys Gln Thr Thr
        370                 375                 380

Leu Glu Leu Arg Tyr Gln Tyr Asn Asp Ile Tyr Met Leu Arg Glu Val
385                 390                 395                 400

Ile Glu Gln Phe Tyr Ile Asp Gly Leu Cys Gly Gly Glu Leu Pro Leu
                405                 410                 415

Thr Gly Met Arg Thr Ala Ser Ser Ile Ala Phe Asn Val Leu Lys Lys
                420                 425                 430

Met Thr Phe Gly Glu Glu Lys Thr Glu Glu Gly Tyr Ile Asn Tyr Phe
                435                 440                 445

Glu Leu Asp Lys Lys Thr Lys Phe Glu Phe Leu Arg Lys Arg Ile Glu
        450                 455                 460

Met Glu Ser Tyr Thr Gly Gly Tyr Thr His Ala Asn His Lys Ala Val
465                 470                 475                 480

Gly Lys Thr Ile Asn Lys Ile Gly Cys Ser Leu Asp Ile Asn Ser Ala
                485                 490                 495

Tyr Pro Ser Gln Met Ala Tyr Lys Val Phe Pro Tyr Gly Lys Pro Val
                500                 505                 510

Arg Lys Thr Trp Gly Arg Lys Pro Lys Thr Glu Lys Asn Glu Val Tyr
        515                 520                 525

Leu Ile Glu Val Gly Phe Asp Phe Val Glu Pro Lys His Glu Glu Tyr
        530                 535                 540

Ala Leu Asp Ile Phe Lys Ile Gly Ala Val Asn Ser Lys Ala Leu Ser
545                 550                 555                 560

Pro Ile Thr Gly Ala Val Ser Gly Gln Glu Tyr Phe Cys Thr Asn Ile
                565                 570                 575

Lys Asp Gly Lys Ala Ile Pro Val Tyr Lys Glu Leu Lys Asp Thr Lys
                580                 585                 590
```

-continued

```
Leu Thr Thr Asn Tyr Asn Val Val Leu Thr Ser Val Glu Tyr Glu Phe
        595                 600                 605

Trp Ile Lys His Phe Asn Phe Gly Val Phe Lys Lys Asp Glu Tyr Asp
    610                 615                 620

Cys Phe Glu Val Asp Asn Leu Glu Phe Thr Gly Leu Lys Ile Gly Ser
625                 630                 635                 640

Ile Leu Tyr Tyr Lys Ala Glu Lys Gly Lys Phe Lys Pro Tyr Val Asp
                645                 650                 655

His Phe Met Lys Met Lys Val Glu Asn Lys Lys Leu Gly Asn Lys Pro
            660                 665                 670

Leu Thr Asn Gln Phe Lys Leu Ile Leu Asn Gly Ala Tyr Gly Lys Phe
            675                 680                 685

Gly Thr Lys Gln Asn Lys Glu Glu Lys Asp Leu Ile Met Asp Lys Asn
        690                 695                 700

Gly Leu Leu Thr Phe Thr Gly Ser Val Thr Lys Tyr Glu Gly Lys Glu
705                 710                 715                 720

Phe Tyr Arg Pro Tyr Ala Ser Phe Val Thr Ala Tyr Gly Arg Leu Gln
                725                 730                 735

Leu Trp Asn Ala Ile Ile Tyr Ala Val Gly Val Glu Asn Phe Leu Tyr
            740                 745                 750

Cys Asp Thr Asp Ser Ile Tyr Cys Asn Arg Glu Val Asn Ser Leu Ile
            755                 760                 765

Glu Asp Met Asn Ala Ile Gly Glu Thr Ile Asp Lys Thr Ile Leu Gly
        770                 775                 780

Lys Trp Asp Val Glu His Val Phe Asp Lys Phe Lys Val Leu Gly Gln
785                 790                 795                 800

Lys Lys Tyr Met Tyr His Asp Cys Lys Glu Asp Lys Thr Asp Leu Lys
                805                 810                 815

Cys Cys Gly Leu Pro Ser Asp Ala Arg Lys Ile Ile Ile Gly Gln Gly
                820                 825                 830

Phe Asp Glu Phe Tyr Leu Gly Lys Asn Val Glu Gly Lys Lys Gln Arg
            835                 840                 845

Lys Lys Val Ile Gly Gly Cys Leu Leu Leu Asp Thr Lys Phe Thr Ile
    850                 855                 860

Lys Lys Ile Met Phe
865

<210> SEQ ID NO 8
<211> LENGTH: 869
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met His His His His His His His Ser Gly Asp Tyr Asp Ile Pro
1               5                   10                  15

Thr Thr Glu Asn Leu Tyr Phe Gln Gly Ala Met Val Asp Thr Leu Ser
                20                  25                  30

Gly Leu Ser Ser Glu Gln Gly Gln Ser Gly Asp Met Thr Ile Glu Glu
            35                  40                  45

Asp Ser Ala Thr His Ile Lys Phe Ser Lys Arg Asp Glu Asp Gly Lys
        50                  55                  60

Glu Leu Ala Gly Ala Thr Met Glu Leu Arg Asp Ser Ser Gly Lys Thr
65                  70                  75                  80
```

-continued

```
Ile Ser Thr Trp Ile Ser Asp Gly Gln Val Lys Asp Phe Tyr Leu Tyr
            85                  90                  95

Pro Gly Lys Tyr Thr Phe Val Glu Thr Ala Ala Pro Asp Gly Tyr Glu
            100                 105                 110

Val Ala Thr Ala Ile Thr Phe Thr Val Asn Glu Gln Gly Gln Val Thr
            115                 120                 125

Val Asn Gly Lys Ala Thr Lys Gly Asp Ala His Ile Gly Gly Ser Asp
        130                 135                 140

Lys His Thr Gln Tyr Val Lys Glu His Ser Phe Asn Tyr Asp Glu Tyr
145                 150                 155                 160

Lys Lys Ala Asn Phe Asp Lys Ile Glu Cys Leu Ile Phe Ala Thr Glu
                165                 170                 175

Ser Cys Thr Asn Tyr Glu Asn Asp Asn Thr Gly Ala Arg Val Tyr Gly
            180                 185                 190

Trp Gly Leu Gly Val Thr Arg Asn His Asn Met Ile Tyr Gly Gln Asn
            195                 200                 205

Leu Asn Gln Phe Trp Glu Val Cys Gln Asn Ile Phe Asn Asp Trp Tyr
        210                 215                 220

His Asp Asn Lys His Thr Ile Lys Ile Thr Lys Thr Lys Lys Gly Phe
225                 230                 235                 240

Pro Lys Arg Lys Tyr Ile Lys Phe Pro Ile Ala Val His Asn Leu Gly
                245                 250                 255

Trp Asp Val Glu Phe Leu Lys Tyr Ser Leu Val Glu Asn Gly Phe Asn
            260                 265                 270

Tyr Asp Lys Gly Leu Leu Lys Thr Val Phe Ser Lys Gly Ala Pro Tyr
            275                 280                 285

Gln Thr Val Thr Asp Val Glu Glu Pro Lys Thr Phe His Ile Val Gln
        290                 295                 300

Asn Asn Asn Ile Val Tyr Gly Cys Asn Val Tyr Met Asp Lys Phe Phe
305                 310                 315                 320

Glu Val Glu Asn Lys Asp Gly Ser Thr Thr Glu Ile Gly Leu Cys Leu
                325                 330                 335

Asp Phe Phe Asp Ser Tyr Lys Ile Ile Thr Cys Ala Glu Ser Gln Phe
            340                 345                 350

His Asn Tyr Val His Asp Val Asp Pro Met Phe Tyr Lys Met Gly Glu
            355                 360                 365

Glu Tyr Asp Tyr Asp Thr Trp Arg Ser Pro Thr His Lys Gln Thr Thr
        370                 375                 380

Leu Glu Leu Arg Tyr Gln Tyr Asn Asp Ile Tyr Met Leu Arg Glu Val
385                 390                 395                 400

Ile Glu Gln Phe Tyr Ile Asp Gly Leu Cys Gly Gly Glu Leu Pro Leu
                405                 410                 415

Thr Gly Met Arg Thr Ala Ser Ser Ile Ala Phe Asn Val Leu Lys Lys
            420                 425                 430

Met Thr Phe Gly Glu Glu Lys Thr Glu Glu Gly Tyr Ile Asn Tyr Phe
            435                 440                 445

Glu Leu Asp Lys Lys Thr Lys Phe Glu Phe Leu Arg Lys Arg Ile Glu
        450                 455                 460

Met Glu Ser Tyr Thr Gly Gly Tyr Thr His Ala Asn His Lys Ala Val
465                 470                 475                 480

Gly Lys Thr Ile Asn Lys Ile Gly Cys Ser Leu Asp Ile Asn Ser Ala
                485                 490                 495
```

-continued

```
Tyr Pro Ser Gln Met Ala Tyr Lys Val Phe Pro Tyr Gly Lys Pro Val
            500                 505                 510

Arg Lys Thr Trp Gly Arg Lys Pro Lys Thr Glu Lys Asn Glu Val Tyr
            515                 520                 525

Leu Ile Glu Val Gly Phe Asp Phe Val Glu Pro Lys His Glu Glu Tyr
            530                 535                 540

Ala Leu Asp Ile Phe Lys Ile Gly Ala Val Asn Ser Lys Ala Leu Ser
545                 550                 555                 560

Pro Ile Thr Gly Ala Val Ser Gly Gln Glu Tyr Phe Cys Thr Asn Ile
                565                 570                 575

Lys Asp Gly Lys Ala Ile Pro Val Tyr Lys Glu Leu Lys Asp Thr Lys
                580                 585                 590

Leu Thr Thr Asn Tyr Asn Val Val Leu Thr Ser Val Glu Tyr Glu Phe
                595                 600                 605

Trp Ile Lys His Phe Asn Phe Gly Val Phe Lys Lys Asp Glu Tyr Asp
            610                 615                 620

Cys Phe Glu Val Asp Asn Leu Glu Phe Thr Gly Leu Lys Ile Gly Ser
625                 630                 635                 640

Ile Leu Tyr Tyr Lys Ala Glu Lys Gly Lys Phe Lys Pro Tyr Val Asp
                645                 650                 655

His Phe Met Lys Met Lys Val Glu Asn Lys Lys Leu Gly Asn Lys Pro
                660                 665                 670

Leu Thr Asn Gln Phe Lys Leu Ile Leu Asn Gly Ala Tyr Gly Lys Phe
                675                 680                 685

Gly Thr Lys Gln Asn Lys Glu Glu Lys Asp Leu Ile Met Asp Lys Asn
            690                 695                 700

Gly Leu Leu Thr Phe Thr Gly Ser Val Thr Lys Tyr Glu Gly Lys Glu
705                 710                 715                 720

Phe Tyr Arg Pro Tyr Ala Ser Phe Val Thr Ala Tyr Gly Arg Leu Gln
                725                 730                 735

Leu Trp Asn Ala Ile Ile Tyr Ala Val Gly Val Glu Asn Phe Leu Tyr
            740                 745                 750

Cys Asp Thr Asp Ser Ile Tyr Cys Asn Arg Glu Val Asn Ser Leu Ile
            755                 760                 765

Glu Asp Met Asn Ala Ile Gly Glu Thr Ile Asp Lys Thr Ile Leu Gly
    770                 775                 780

Lys Trp Asp Val Glu His Val Phe Asp Lys Phe Lys Val Leu Gly Gln
785                 790                 795                 800

Lys Lys Tyr Met Tyr His Asp Cys Lys Glu Asp Lys Thr Asp Leu Lys
                805                 810                 815

Cys Cys Gly Leu Pro Ser Asp Ala Arg Lys Ile Ile Ile Gly Gln Gly
                820                 825                 830

Phe Asp Glu Phe Tyr Leu Gly Lys Asn Val Glu Gly Lys Lys Gln Arg
            835                 840                 845

Lys Lys Val Ile Gly Gly Cys Leu Leu Leu Asp Thr Leu Phe Thr Ile
    850                 855                 860

Lys Lys Ile Lys Phe
865
```

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 9

His His His His His His
1               5

<210> SEQ ID NO 10
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Gly Asp Tyr Asp Ile Pro Thr Thr Glu Asn Leu Tyr Phe Gln Gly
1               5                   10                  15

Ala Met Val Asp Thr Leu Ser Gly Leu Ser Ser Glu Gln Gly Gln Ser
                20                  25                  30

Gly Asp Met Thr Ile Glu Glu Asp Ser Ala Thr His Ile Lys Phe Ser
            35                  40                  45

Lys Arg Asp Glu Asp Gly Lys Glu Leu Ala Gly Ala Thr Met Glu Leu
        50                  55                  60

Arg Asp Ser Ser Gly Lys Thr Ile Ser Thr Trp Ile Ser Asp Gly Gln
65                  70                  75                  80

Val Lys Asp Phe Tyr Leu Tyr Pro Gly Lys Tyr Thr Phe Val Glu Thr
                85                  90                  95

Ala Ala Pro Asp Gly Tyr Glu Val Ala Thr Ala Ile Thr Phe Thr Val
            100                 105                 110

Asn Glu Gln Gly Gln Val Thr Val Asn Gly Lys Ala Thr Lys Gly Asp
        115                 120                 125

Ala His Ile
    130

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala His Ile Val Met Val Asp Ala Tyr Lys Pro Thr Lys
1               5                   10

<210> SEQ ID NO 12
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
agagtgatag tatgattatg tagatgtagg atttgatatg tgagtagccg aatgaaacct        60
t                                                                        61

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 13
ttttcataat catactatca ctct                                                    24

<210> SEQ ID NO 14
<211> LENGTH: 739
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 14

Met His His His His His His His Ser Gly Gly Ser Asp Lys His
1               5                   10                  15

Thr Gln Tyr Val Lys Glu His Ser Phe Asn Tyr Asp Glu Tyr Lys Lys
            20                  25                  30

Ala Asn Phe Asp Lys Ile Glu Cys Leu Ile Phe Asp Thr Glu Ser Cys
        35                  40                  45

Thr Asn Tyr Glu Asn Asp Asn Thr Gly Ala Arg Val Tyr Gly Trp Gly
    50                  55                  60

Leu Gly Val Thr Arg Asn His Asn Met Ile Tyr Gly Gln Asn Leu Asn
65                  70                  75                  80

Gln Phe Trp Glu Val Cys Gln Asn Ile Phe Asn Asp Trp Tyr His Asp
                85                  90                  95

Asn Lys His Thr Ile Lys Ile Thr Lys Thr Lys Lys Gly Phe Pro Lys
            100                 105                 110

Arg Lys Tyr Ile Lys Phe Pro Ile Ala Val His Asn Leu Gly Trp Asp
        115                 120                 125

Val Glu Phe Leu Lys Tyr Ser Leu Val Glu Asn Gly Phe Asn Tyr Asp
    130                 135                 140

Lys Gly Leu Leu Lys Thr Val Phe Ser Lys Gly Ala Pro Tyr Gln Thr
145                 150                 155                 160

Val Thr Asp Val Glu Glu Pro Lys Thr Phe His Ile Val Gln Asn Asn
                165                 170                 175

Asn Ile Val Tyr Gly Cys Asn Val Tyr Met Asp Lys Phe Phe Glu Val
            180                 185                 190

Glu Asn Lys Asp Gly Ser Thr Thr Glu Ile Gly Leu Cys Leu Asp Phe
        195                 200                 205

Phe Asp Ser Tyr Lys Ile Ile Thr Cys Ala Glu Ser Gln Phe His Asn
    210                 215                 220

Leu Val His Asp Val Asp Pro Met Phe Tyr Lys Met Gly Glu Glu Tyr
225                 230                 235                 240

Asp Ala Asp Thr Trp Arg Ser Pro Thr His Lys Gln Thr Thr Leu Glu
                245                 250                 255

Leu Arg Tyr Gln Tyr Asn Asp Ile Tyr Met Leu Arg Glu Val Ile Glu
            260                 265                 270

Gln Phe Tyr Ile Asp Gly Leu Cys Gly Gly Glu Leu Pro Leu Thr Gly
        275                 280                 285

Met Arg Thr Ala Ser Ser Ile Ala Phe Asn Val Leu Lys Lys Met Thr
    290                 295                 300

Phe Gly Glu Glu Lys Thr Glu Glu Gly Tyr Ile Asn Tyr Phe Glu Leu
305                 310                 315                 320

-continued

```
Asp Lys Lys Thr Lys Phe Glu Phe Leu Arg Lys Arg Ile Glu Met Glu
            325                 330                 335

Ser Tyr Thr Gly Gly Tyr Thr His Ala Asn His Lys Ala Val Gly Lys
            340                 345                 350

Thr Ile Asn Lys Ile Gly Cys Ser Leu Asp Ile Asn Ser Ala Tyr Pro
            355                 360                 365

Ser Gln Met Ala Tyr Lys Val Phe Pro Tyr Gly Lys Pro Val Arg Lys
        370                 375                 380

Thr Trp Gly Arg Lys Pro Lys Thr Glu Lys Asn Glu Val Tyr Leu Ile
385                 390                 395                 400

Glu Val Gly Phe Asp Phe Val Glu Pro Lys His Glu Glu Tyr Ala Leu
                405                 410                 415

Asp Ile Phe Lys Ile Gly Ala Val Asn Ser Lys Ala Leu Ser Pro Ile
            420                 425                 430

Thr Gly Ala Val Ser Gly Gln Glu Tyr Phe Cys Thr Asn Ile Lys Asp
            435                 440                 445

Gly Lys Ala Ile Pro Val Tyr Lys Glu Leu Lys Asp Thr Lys Leu Thr
        450                 455                 460

Thr Asn Tyr Asn Val Val Leu Thr Ser Val Glu Tyr Glu Phe Trp Ile
465                 470                 475                 480

Lys His Phe Asn Phe Gly Val Phe Lys Lys Asp Glu Tyr Asp Cys Phe
                485                 490                 495

Glu Val Asp Asn Leu Glu Phe Thr Gly Leu Lys Ile Gly Ser Ile Leu
            500                 505                 510

Tyr Tyr Lys Ala Glu Lys Gly Lys Phe Lys Pro Tyr Val Asp His Phe
            515                 520                 525

Met Lys Met Lys Val Glu Asn Lys Lys Leu Gly Asn Lys Pro Leu Thr
        530                 535                 540

Leu Gln Phe Lys Leu Ile Leu Asn Gly Ala Tyr Gly Lys Phe Gly Thr
545                 550                 555                 560

Lys Gln Asn Lys Glu Glu Lys Asp Leu Ile Met Asp Lys Asn Gly Leu
                565                 570                 575

Leu Thr Phe Thr Gly Ser Val Thr Glu Tyr Glu Gly Lys Glu Phe Tyr
            580                 585                 590

Arg Pro Tyr Ala Ser Phe Val Thr Ala Tyr Gly Arg Leu Gln Leu Trp
        595                 600                 605

Asn Ala Ile Ile Tyr Ala Val Gly Val Glu Asn Phe Leu Tyr Cys Asp
        610                 615                 620

Thr Asp Ser Ile Tyr Cys Asn Arg Glu Val Asn Ser Leu Ile Glu Asp
625                 630                 635                 640

Met Asn Ala Ile Gly Glu Thr Ile Asp Lys Thr Ile Leu Gly Lys Trp
                645                 650                 655

Arg Val Glu His Val Phe Asp Lys Phe Lys Val Leu Gly Gln Lys Lys
            660                 665                 670

Tyr Met Tyr His Asp Cys Lys Glu Asp Lys Thr Asp Leu Lys Cys Cys
            675                 680                 685

Gly Leu Pro Ser Asp Ala Arg Lys Ile Ile Ile Gly Gln Gly Phe Asp
        690                 695                 700

Glu Phe Tyr Leu Gly Lys Asn Val Glu Gly Lys Lys Gln Arg Lys Lys
705                 710                 715                 720

Val Ile Gly Gly Cys Leu Leu Leu Asp Thr Leu Phe Thr Ile Lys Lys
                725                 730                 735

Ile Met Phe
```

-continued

<210> SEQ ID NO 15
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
actgctgatc tgttcctgaa tcgactacta ctatcatcat accacctcag ctgcacgtt         59

<210> SEQ ID NO 16
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
agagtgatag tatgattatg tatgtgagta gtccactgaa acctttggtt tcagtggac         59

<210> SEQ ID NO 17
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
atctcttcaa ctcgacttat gttctactgc tgatctgttc ctgaatcgac tactactatc         60
atcataccac ctcagctgca cgt                                                  83

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tttgattcag gaacagatca gcagtagaac ataagtcgag ttgaagagat                    50

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 1-3 "Gly Gly Gly
      Gly Ser" repeating units

<400> SEQUENCE: 19

Gly Gly Gly Gly Ser Gly Gly Gly Gly Ser Gly Gly Gly Gly Ser
1               5                   10                  15

<210> SEQ ID NO 20
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 20

Arg Ser Lys Leu Gly
1               5

<210> SEQ ID NO 21
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttggtttcat tcgg                                                   14

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aagtgcagct gaggtgg                                                17
```

POLYMERASE-TEMPLATE COMPLEXES

CROSS-REFERENCE TO RELATED APPLICATIONS

This is a continuation of U.S. Ser. No. 16/505,496, filed on Jul. 8, 2019, which is a continuation of U.S. Ser. No. 15/444,042, filed Feb. 27, 2017, and claims the benefit of U.S. Provisional Patent Application No. 62/406,431 filed Oct. 11, 2016 and the benefit of U.S. Provisional Patent Application No. 62/301,607 filed Feb. 29, 2016, the disclosures of which are each incorporated herein by reference in their entireties.

SEQUENCE LISTING

The instant application contains a Sequence Listing which has been submitted electronically in ASCII format and is hereby incorporated by reference in its entirety. Said ASCII copy, created on Aug. 8, 2019, is named P33453US2_Seq_List_ST25.txt and is 60,671 bytes in size.

TECHNICAL FIELD

The present disclosure relates generally to methods and compositions for improving DNA sequencing processivity, and more particularly to enhancing sequencing yield in a DNA sequencing reaction via adjustment of temperature, nucleotide concentration, and/or polymerase concentration.

BACKGROUND

Nanopores have recently emerged as a label-free platform for interrogating sequence and structure in nucleic acids. Data are typically reported as a time series of ionic current as DNA sequence is determined when an applied electric field is applied across a single pore controlled by a voltage-clamped amplifier. Hundreds to thousands of molecules can be examined at high bandwidth and spatial resolution.

A crucial obstacle to the success of nanopores as a reliable DNA analysis tool is the processivity or average read length. Efficient binding of template by the polymerase, for example, is key to high sequencing yield. This and other desirable properties can be enhanced by modifying polymerases to increase the amount of sequence information obtained from a template-dependent sequencing reaction. Additionally, processivity can also be increased by providing conditions that favor the formation (or stabilize) the polymerase-template complexes. Due to the numerous varying conditions at which the sequencing reaction can be ran, however, the specific variables (conditions) that optimize certain sequencing reactions, such as nanopore based sequencing, have remained largely elusive.

SUMMARY OF THE INVENTION

Provided herein are methods and compositions that can be used to optimize sequencing reactions, such as nanopore-based sequencing. In certain example aspects, provided are methods and compositions that utilize high salt concentration to enhance a sequencing reaction. In one aspect, for example, provided is a method is provided for preparing a polymerase-template complex. The method comprises (a) providing a polymerase; and (b) contacting the polymerase with a polynucleotide template in a solution comprising a high concentration of salt and being essentially free of nucleotides, thereby preparing the polymerase-template complex.

In another aspect, a method is provided for increasing the processivity of a template-polymerase complex, the method comprising forming a template-polymerase complex in a solution comprising a high concentration of salt and being essentially free of nucleotides; wherein the processivity of the template-polymerase complex is greater than the processivity of the same template-polynucleotide complex when formed in a solution comprising an equally high concentration of salt and in the presence of nucleotides. For example, the processivity is increased by a faster rate of association of the template with the polymerase, and/or the processivity is increased by a slower rate of dissociation of the template from the polymerase.

In another aspect, a method is provided for performing template-dependent DNA synthesis, the method comprising: (a) providing a polymerase-template complex in a solution comprising a high concentration of salt and being essentially free of nucleotides; and (b) initiating template-dependent DNA synthesis by adding nucleotides to the solution.

In another aspect, a method is provided for nanopore sequencing at high salt concentration, the method comprising: (a) providing a polymerase-template complex in a solution comprising a high concentration of salt, the solution being essentially free of nucleotides; (b) combining the polymerase-template complex with a nanopore to form a nanopore-sequencing complex; (c) providing tagged nucleotides to the nanopore sequencing complex to initiate template-dependent nanopore sequencing of the template at high concentration of salt; and (d) detecting with the aid of the nanopore, a tag associated with each of the tagged nucleotides during incorporation of each of the nucleotides while each of the nucleotides is associated with the polymerase, thereby determining the sequence of the polynucleotide template.

In each of the various foregoing aspects, the polymerase may be a variant polymerase, such as a polymerase comprising an amino acid sequence having at least 70% sequence identity to the polymerase of SEQ ID NO:2. Further, the nanopore can be a monomeric nanopore, such as an OmpG nanopore, or the nanopore can be an oligomeric nanopore such as an alpha-hemolysin nanopore. Moreover, the high concentration of salt is defined, for example, as a salt concentration of at least 100 mM.

In another aspect, a storage or reaction composition is provided, the storage or reaction composition comprising a polymerase-template complex in a solution of at least 100 mM salt. In some embodiments, the composition is essentially free of nucleotides.

In certain other example aspects, provided are methods and compositions that utilize low nucleotide concentrations and high temperatures to enhance a sequencing reaction. For example, in one aspect provided is a method for preparing a polymerase-template complex. The method includes, for example, providing a polymerase and then contacting the polymerase with a polynucleotide template in a solution, thereby preparing the polymerase-template complex. The solution includes a low concentration of nucleotides and has a high temperature.

In another aspect, provided is a method for increasing processivity of a template-polymerase complex. The method includes forming a polymerase-template complex in a solution—the solution including a low concentration of nucleotides and having a high temperature. In such methods, the processivity of the polymerase-template complex formed in the high-temperature solution is greater than a processivity resulting from a control polymerase-template complex solution at room temperature.

In another aspect, provided is a method for nanopore-based sequencing of a polynucleotide template. The method includes forming a polymerase-template complex in a solution—the solution including a low concentration of nucleotides having a high temperature. The formed polymerase-template complex is combined with a nanopore to form a nanopore-sequencing complex. Tagged nucleotides are provided to the nanopore sequencing complex to initiate template-dependent nanopore sequencing of the template at the high temperature. With the aid of the nanopore, a tag associated with each of the tagged nucleotides is detected during incorporation of each of the tagged nucleotides while each of the tagged nucleotides is associated with the polymerase, thereby determining the sequence of the polynucleotide template. The nanopore may be a monomeric nanopore, such as an OmpG nanopore, or a multimeric nanopore, such as an alpha-hemolysin based nanopore.

In each of the foregoing aspects involving low nucleotide concentrations and high temperatures, the method may further include saturating the solution with the polymerase of the polymerase-template complex. The polymerase, for example, may be a polymerase variant, such as a polymerase having 85%, 90%, 95%, 98% or more sequence identity to the amino acid sequence set forth as SEQ ID NO: 2. In certain aspects, the low concentration of the nucleotides is between is 0.8 μM to 2.2 μM, such as 1.2 μM. In certain aspects, the high temperature is above room temperature, such as 35° C. to 45° C. In certain aspects, the high temperature is 40° C.

Other objects, features, and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIG. 11A is an image of a Native 5% TBE gel showing binding of polymerase concentration at 0, 1×, 2×, 4×, 6×, and 8× to template. As shown, increasing polymerase results in an increase in template binding at 40° C. and in the presence of 1.2 μM nucleotides. FIG. 11B is an image of a Native 5% TBE gel showing extension of the template, following binding shown in FIG. 11A. As evidenced by the shifts in band intensity from the lower band to the upper band with increased concentration of polymerase, increasing the concentration of polymerase results in increased template extension (the extension occurring in the presence of 10 μM nucleotides). FIG. 11C is a graph showing the correlation of template binding (from FIG. 11A) with template extension (FIG. 11B). As shown, the % bound correlates directly with the % extension (slope=1). Reference is made to Example 6.

FIG. 12A shows amplitude curves for the fluorescence signal obtained in a FRET assay, with increasing concentration of polymerase (0, 1×, 2×, 4×, 6×, 8×, and 1×) to template. As shown, increasing polymerase concentration at binding results in increased extension (as evidenced the by increased signal amplitude at increased concentrations compared to controls). FIG. 12B shows the amplitude quantification of the fluorescent signals for the data in FIG. 12A, i.e., the fluorophore-quencher (extension reaction) (□) as compared to the fluorophore alone (▲). FIG. 12C shows the percent extension (♦) of the polymerase at increasing polymerase concentrations, as determined by comparing the fluorescent amplitude of the fluorophore-quencher (extension reaction) to the fluorescent amplitude of the fluorophore alone. FIG. 12D shows template extension comparison between the gel based assay (see above) and the plate reader (FRET) assay. As shown, there is good correlation between % template extension as measured by gel-based or plate-reader based assays. For FIGS. 12A-12D, Reference is made to Example 7.

FIG. 13A shows the amplitude curves for the fluorescence signal obtained in a FRET assay for the binding conditions indicated. FIG. 13B shows the dissociation curves for 1.2 μM dNpCpp (blocking nucleotides)/3 mM Sr$^{+2}$ (♦); 1.2 μM dNpCpp alone (□); 1.2 μM polyphosphate nucleotides (▲) alone; or no nucleotides/Sr (×). As shown, Sr$^{+2}$ does not impact polymerase-template dissociation. A low concentration of polyphosphate nucleotides (▲) provides the lowest level of dissociation. Reference is made to Example 8.

FIG. 14A shows the dissociation curve obtained from a FRET assay at 75 mM KGlu in the presence of nucleotides (□) (final concentration 10 μM) and in the absence of nucleotides (control) (♦). FIG. 14B shows the dissociation curve obtained from a FRET assay at 380 mM KGlu in the presence of nucleotides (□) (final concentration 10 μM) and in the absence of nucleotides (control) (♦). As shown, the amount of template bound at time zero is roughly 2-fold better in the absence of nucleotides. Hence, at both salt concentrations, the presence of high nucleotide concentration (10 uM+during binding) decreases polymerase-template binding. Reference is made to Example 9.

DETAILED DESCRIPTION

Figure 1:
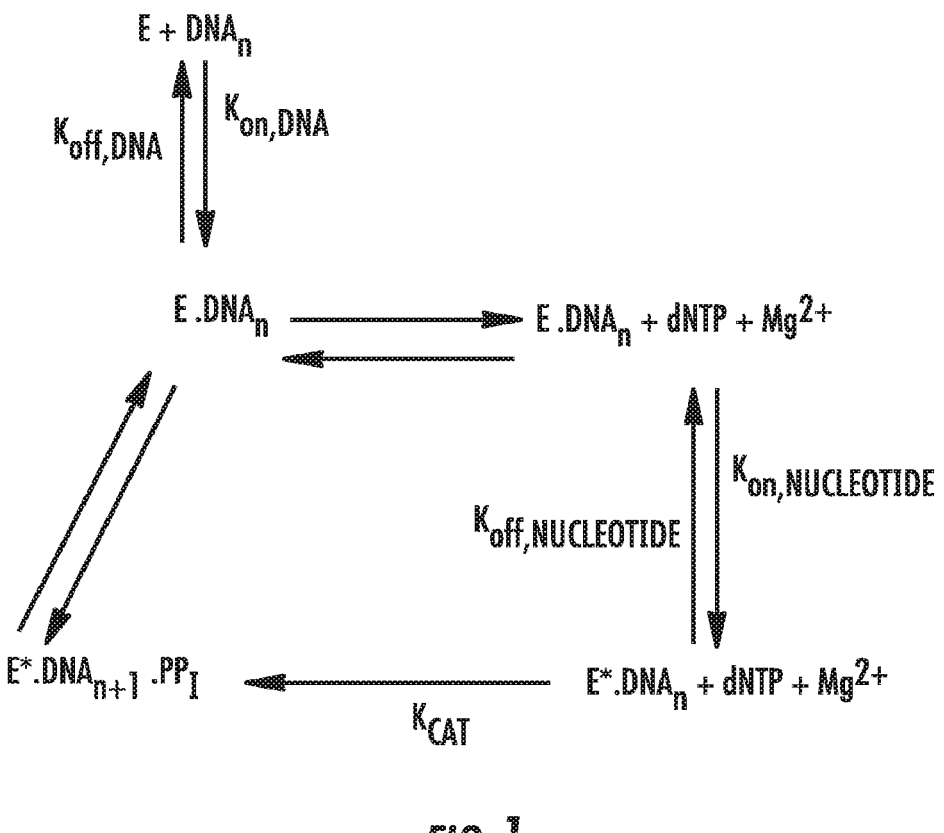
FIG. 1 is an illustration of the minimal catalytic steps required for single-nucleotide incorporation by DNA polymerase. The reaction begins with the binding of free DNA polymerase enzyme (E) to a duplex primer/template DNA complex ($DNA_n$) resulting in a binary enzyme-DNA complex ($E \cdot DNA_n$). $k_{on.DNA}$ denotes the rate of association of the enzyme with the template; and $k_{off.DNA}$ denotes the rate of dissociation of the enzyme from the enzyme-DNA complex. The equilibrium determined by the $k_{on.DNA}$ and $k_{off.DNA}$ rates defines the static processivity of the polymerase-template complex. Thus, the static processivity of the enzyme can be increased by an increase in the rate of association, $k_{on.DNA}$, and/or a decrease in the rate of dissociation, $k_{off.DNA}$ Association of the correct nucleotide (dNTP) in the presence of divalent cations, such as $Mg^{2+}$, promotes the enzyme-DNA-dNTP ternary complex formation ($E \cdot DNA_n \cdot dNTP \cdot Mg^{2+}$). The $k_{on, nucleotide}$ denotes the rate of nucleotide binding of the enzyme. The $k_{off, nucleotide}$ denotes the rate of nucleotide dissociation form the enzyme template complex. The equilibrium determined by the $k_{on, DNA}$ and $k_{off, DNA}$ while the polymerase is extending the template defines the replicative processivity of the polymerase. Thus, the replicative processivity of the polymerase can be increased by an increase in the rate of DNA association, $k_{on, DNA}$, and/or a decrease in the rate of DNA dissociation, $k_{off, DNA}$. The binding of the dNTP induces the first conformational change of the enzyme in the ternary complex. A phosphodiester bond is formed between the a-phosphate of the incoming dNTP and the 3'-OH of the template/primer terminus to produce an added nucleotide base to the primer terminus ($E^* \cdot DNA_{n+1} \cdot PP_i$). The reaction generates a pyrophosphate ($PP_i$) and a proton. A second conformational change allows for the release of the $PP_i$ to complete a cycle of nucleotide incorporation.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range. The term about is used herein to mean plus or minus ten percent (10%) of a value. For example, "about 100" refers to any number between 90 and 110.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention, which can be had by reference to the specification as a whole. Accordingly, the terms defined immediately below are more fully defined by reference to the specification as a whole.

All patents and publications, including all sequences disclosed within such patents and publications, referred to herein are expressly incorporated by reference.

Definitions

The term "processivity" herein refers to the ability of a polymerase to remain attached to the template and perform multiple modification reactions. "Modification reactions" include but are not limited to polymerization, and exonucleolytic cleavage. In some embodiments, "processivity" refers to the ability of a DNA polymerase to perform a sequence of polymerization steps without intervening dissociation of the enzyme from the growing DNA chains. Typically, "processivity" of a DNA polymerase is measured by the number of nucleotides (for example 20 nts, 300 nts, 0.5-1 kb, or more) that are incorporated i.e. polymerized by a polymerase into a growing DNA strand prior to the dissociation of the DNA polymerase from the growing DNA strand. The processivity of DNA synthesis by a DNA polymerase is defined as the number of nucleotides that a polymerase can incorporate into DNA during a single template-binding event, before dissociating from a DNA template. The overall efficiency of DNA synthesis increases when the processivity of a polymerase increases. "Processivity" can depend on the nature of the polymerase, the sequence of a DNA template, and reaction conditions, for example, salt concentration, temperature or the presence of specific proteins. As used herein, the term "high processivity" refers to a processivity higher than 20 nts (e.g., higher than 40 nts, 60 nts, 80 nts, 100 nts, 120 nts, 140 nts, 160 nts, 180 nts, 200 nts, 220 nts, 240 nts, 260 nts, 280 nts, 300 nts, 320 nts, 340 nts, 360 nts, 380 nts, 400 nts, or higher) per association/dissociation with the template. The higher the processivity of a polymerase, that greater the number of nucleotides that can be incorporated prior to dissociation of the polymerase from the template, and therefore, the longer the sequence (read length) that can be obtained. Processivity can be measured according the methods defined herein and in WO 01/92501 A1 (MJ Bioworks, Inc., Improved Nucleic Acid Modifying Enzymes, published 6 Dec. 2001). Processivity encompasses static processivity and replicative processivity.

The term "static processivity" herein refers to the permanence of a polymerase-template complex in the absence of nucleotide incorporation i.e. in the absence of polynucleotide synthesis, as determined by the rate of association of polymerase with template, $k_{on,DNA}$, and the rate of dissociation of polymerase from the polymerase-template complex $k_{off,DNA}$. Static processivity is defined in the absence of polynucleotide synthesis.

The term "replicative processivity" herein refers to the permanence of a polymerase-template complex in the during nucleotide incorporation i.e. in the presence of polynucleotide synthesis, as determined by the rate of association of polymerase with template, $k_{on, nucleotide}$, and the rate of dissociation of polymerase from the polymerase-template complex $k_{off, nucleotide}$.

As used herein, the term "association rate," when used in reference to a given polymerase, herein refers to the rate at which a polymerase associates with a template. The association rate can be interpreted as a time constant for association ("$k_{on, DNA}$") of a polymerase with a nucleic acid template under a defined set of reaction conditions. Some exemplary assays for measuring the dissociation time constant of a polymerase are described further below. In some embodiments, the dissociation time constant can be measured in units of inverse time, e.g., $^{sec-1}$ or $min^{-1}$.

The term "dissociation rate," when used in reference to a given polymerase, herein refers to the rate at which a polymerase dissociates from the template of the polymerase-template complex. The dissociation rate can be interpreted as a time constant for dissociation ("$k_{off, DNA}$") of a polymerase from a nucleic acid template under a defined set of reaction conditions. Some exemplary assays for measuring the dissociation time constant of a polymerase are described further below. In some embodiments, the dissociation time constant can be measured in units of inverse time, e.g., $^{sec-1}$ or $min^{-1}$.

The term "stability" when used in reference to a polymerase-template complex, herein refers to the permanence of a polymerase-template complex, as determined by the rates of association and dissociation of the template to and from the polymerase.

The term "read length" herein refers to the number of nucleotides that a polymerase incorporates into a nucleic acid strand in a template-dependent manner prior to dissociation from the template.

The term "high concentration of salt" herein refers to a concentration of salt, i.e., monovalent salt that is at least 100 mM and up to 1 M salt.

The term "salt-tolerant" is used herein in reference to a polymerase enzyme that retains polymerase activity in a solution comprising a high salt concentration e.g. greater than 100 mM salt.

The term "essentially free of nucleotides" herein refers to a solution that is at least 99.9% free of nucleotides.

The terms "polynucleotide" and "nucleic acid" are herein used interchangeably to refer to a polymer molecule composed of nucleotide monomers covalently bonded in a chain. Single stranded DNA (ss deoxyribonucleic acid; ssDNA), double stranded DNA (dsDNA) and RNA (ribonucleic acid) are examples of polynucleotides.

The term "amino acid" in its broadest sense, herein refers to any compound and/or substance that can be incorporated into a polypeptide chain. In some embodiments, an amino acid has the general structure $H_2N—C(H)(R)—COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical without adversely affecting their activity. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide. It should be noted that all amino acid residue sequences are represented herein by formulae whose left and right orientation is in the conventional direction of amino-terminus to carboxy-terminus.

The term "nanopore sequencing complex" or "nanopore complex" herein refers to a nanopore linked to an enzyme, e.g., a polymerase, which in turn is associated with a polymer, e.g., a polynucleotide or a protein. The nanopore sequencing complex is positioned in a membrane, e.g., a lipid bilayer, where it functions to identify polymer components, e.g., nucleotides or amino acids.

The term "polymerase-template complex" herein refers to a polymerase that is associated/coupled with a polymer, e.g., polynucleotide template.

The term "complexed polymerase" herein refers to a polymerase that is associated with a polynucleotide template in a polymerase-template complex.

The term "nucleotide" herein refers to a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence," and is represented herein by a formula whose left to right orientation is in the conventional direction of 5'-terminus to 3'-terminus.

The term "nucleotide analog" herein refers to analogs of nucleoside triphosphates, e.g., (S)-Glycerol nucleoside triphosphates (gNTPs) of the common nucleobases: adenine, cytosine, guanine, uracil, and thymidine (Horhota et al. Organic Letters, 8:5345-5347 [2006]).

The term "tag" herein refers to a detectable moiety that may be atoms or molecules, or a collection of atoms or molecules. A tag may provide an optical, electrochemical, magnetic, or electrostatic (e.g., inductive, capacitive) signature, which may be detected with the aid of a nanopore.

The term "tagged nucleotide" herein refers to a nucleotide having a tag attached at its terminal phosphate.

The term "blocked nucleotide" herein refers to a modified non-incorporable nucleotide that blocks primer extension. dNpCpp is an example of a "blocked nucleotide."

The term "polymerase" herein refers to an enzyme that catalyzes the polymerization of nucleotide (i.e., the polymerase activity). The term polymerase encompasses DNA polymerases, RNA polymerases, and reverse transcriptases.—A "DNA polymerase" catalyzes the polymerization of deoxynucleotides. An "RNA polymerase" catalyzes the polymerization of ribonucleotides. A "reverse transcriptase" catalyzes the polymerization of deoxynucleotides that are complementary to an RNA template. As used herein, the term "polymerase" and its variants comprise any enzyme that can catalyze the polymerization of nucleotides (including analogs thereof) into a nucleic acid strand. Typically but not necessarily such nucleotide polymerization can occur in a template-dependent fashion.

The terms "template DNA molecule" and "template strand" are used interchangeably herein to refer to a strand of a nucleic acid from which a complementary nucleic acid strand is synthesized by a DNA polymerase, for example, in a primer extension reaction.

The term "sample polynucleotide" herein refers to a polynucleotide obtained from a sample, e.g., a biological sample.

The term "template-dependent synthesis" refers to a process that involves the synthesis of a new DNA strand (e.g., DNA synthesis by DNA polymerase) that is complementary to a template strand of interest. The term "template-dependent synthesis" typically refers to polynucleotide synthesis of RNA or DNA wherein the sequence of the newly synthesized strand of polynucleotide is dictated by complementary base pairing (see, for example, Watson, J. D. et al., In: Molecular Biology of the Gene, 4th Ed., W. A. Benjamin, Inc., Menlo Park, Calif. (1987)).

The term "nanopore" herein refers to a channel or passage formed or otherwise provided in a membrane. A membrane may be an organic membrane, such as a lipid bilayer, or a synthetic membrane, such as a membrane formed of a polymeric material. The nanopore may be disposed adjacent or in proximity to a sensing circuit or an electrode coupled to a sensing circuit, such as, for example, a complementary metal oxide semiconductor (CMOS) or field effect transistor (FET) circuit. In some examples, a nanopore has a characteristic width or diameter on the order of 0.1 Nm to about 1000 nm. Some nanopores are proteins. OmpG and alpha-hemolysin are examples of a protein nanopore.

The terms "alpha-hemolysin," "α-hemolysin," "aHL," "αHL," "a-HL" and "α-HL" are used interchangeably and herein refer to a protein that self-assembles into a heptameric water-filled transmembrane nanopore channel.

The term "OmpG" herein refers to an Outer Membrane Protein G monomeric nanopore.

The term "nanopore sequencing" herein refers to a method that determines the sequence of a polynucleotide with the aid of a nanopore. In some embodiments, the sequence of the polynucleotide is determined in a template-dependent manner.

The term "monomeric nanopore" herein refers to a nanopore protein that consists of a single subunit. OmpG is an example of a monomeric nanopore.

The term "oligomeric nanopore" herein refers to nanopores that can be composed of multiple identical subunits, multiple distinct subunits, or a mixture of identical and distinct subunits. Nanopores with identical subunits are termed "homo-oligomeric nanopores". Nanopores containing two or more distinct polypeptide subunits are termed "hetero-oligomeric nanopores". Alpha-hemolysin is an example of an oligomeric nanopore.

The term "wild-type" herein refers to a gene or gene product (e.g., a protein) that has the characteristics of that gene or gene product when isolated from a naturally occurring source.

The term "parental" or "parent" herein refers to a protein, e.g., a nanopore or enzyme, to which modifications, e.g., substitution(s), insertion(s), deletion(s), and/or truncation(s), are made to produce variants thereof. This term also refers to the polypeptide with which a variant is compared and aligned. The parent may be a naturally occurring (wild type) polypeptide, or it may be a variant thereof, prepared by any suitable means.

The term "mutation" herein refers to a change introduced into a parental sequence, including, but not limited to, substitutions, insertions, deletions (including truncations). The consequences of a mutation include, but are not limited to, the creation of a new character, property, function, phenotype or trait not found in the parental sequence.

The term "variant" herein refers to a modified protein e.g. a variant Pol6 polymerase, which displays altered characteristics when compared to the parental protein, e.g., altered processivity.

The term "purified" herein refers to a polypeptide that is present in a sample at a concentration of at least 95% by weight, or at least 98% by weight of the sample in which it is contained.

Nomenclature

In the present description and claims, the conventional one-letter and three-letter codes for amino acid residues are used.

For ease of reference, polymerase variants of the application are described by use of the following nomenclature: Original amino acid(s): position(s): substituted amino acid(s). According to this nomenclature, for instance the substitution of serine by an alanine in position 242 is shown as:

Glu585Lys or E585K.

Multiple mutations are separated by plus signs, i.e.:

Glu585Lys+Leu731Lys or E585K+L731K representing mutations in positions 585 and 731 substituting glutamic acid and Leucine acid for Lysine and Leucine for Lysine, respectively.

When one or more alternative amino acid residues may be inserted in a given position it is indicated as: E585K/R or E585K or E585R.

EXAMPLE EMBODIMENTS

In certain example embodiments, the present disclosure provides methods and compositions for enhancing the processivity of the polymerase during template-dependent polynucleotide synthesis in the presence of a high concentration of salt. In other example embodiments, the present disclosure provides methods and compositions for enhancing the processivity of the polymerase during template-dependent polynucleotide synthesis in the presence of low nucleotide concentrations and high temperatures. The methods and compositions provided are applicable to methods of template-dependent DNA synthesis, including DNA amplification and sequencing. Sequencing methods include sequencing-by-synthesis of single polynucleotide molecules, such as nanopore sequencing of single DNA molecules.

As illustrated in FIG. 1, the processivity of a polymerase, such as a DNA polymerase, is directly related to the formation of the polymerase-template complex and the incorporation of dNTP by the enzyme. Under these parameters, the overall processivity of the polymerase is dependent on the static and replicative processivity. The greater the static and/or the replicative processivity of the polymerase, the greater the overall processivity of the polymerase. As shown in FIG. 1, the static processivity is determined by the rate of association ($k_{on,\ DNA}$) and dissociation ($k_{off,\ DNA}$) of the polymerase with the template. Static processivity is determined in the absence of polynucleotide synthesis. Thus, the greater (or faster) the rate of association of polymerase with template, and/or the lesser (or slower) the rate of dissociation of polymerase from template, the greater the static processivity of the polymerase.

Replicative processivity is determined in the presence of nucleotides and based on the rate of association and dissociation of nucleotide with the polymerase of the polymerase-template complex. Thus, the greater (or faster) the rate of association of nucleotide with the complexed polymerase, and/or the lesser (or slower) the rate of dissociation of nucleotide from the complexed polymerase, the greater the replicative processivity of the polymerase. The replicative processivity is determined by the rate of association ($k_{on,\ nucleotide}$) and rate of dissociation ($k_{off,\ nucleotide}$) of nucleotide from the polymerase-template complex under conditions of polymerization, such as in the presence of nucleotides and divalent cation such as $Mg^{2+}$. The static processivity of a polymerase can be increased by an increase in the association of polymerase with template to form the polymerase-template complex, and/or a decrease in the dissociation of polymerase from the polymerase-template complex.

Figure 2:
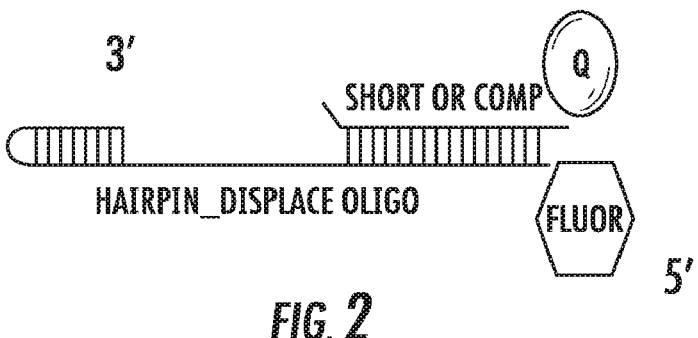
FIG. 2 is an illustration showing an exemplary template used in a FRET displacement assay.

In exemplary assays, as described in the Examples herein, the association and dissociation rate of a given polymerase with and from a template can be measured by incubating the polymerase with a labeled oligonucleotide including a fluorescent label (FIG. 2) under defined conditions. When the oligonucleotide is not bound by polymerase, the fluorescence of the fluorescent label on the oligonucleotide is quenched; binding of the polymerase to the oligonucleotide results in de-quenching of the oligonucleotide label and a resulting increase in fluorescence. Blocking is initiated by adding an unlabeled competitor oligonucleotide to the reaction mixture; as polymerase dissociates from the fluorescently labeled oligonucleotide, the competitor oligonucleotide hybridizes to oligonucleotide and prevents further binding of the polymerase. Fluorescence of the reaction mixture is measured at various time points following addition of the competitor oligonucleotide. The observed fluorescence (in RFU or relative fluorescence units) is graphed (Y axis) against time (X axis). To compare association and dissociation rates of a polymerase under different conditions, the enzyme can be employed in a parallel and separate reactions in which the fluorescence of each reaction mixture is measured at various time points, following which the dissociation rates for each enzyme can be calculated using any suitable method, and compared.

Published methods describe that binding of template to polymerase to form the polymerase-template complex is carried out in the presence of nucleotides as nucleotides have been utilized to stabilize the polymerase-template complex. For example, US20150167072 provides methods for the purification of polymerase-template complexes, which include nucleotides and nucleotide analogs in the purification process to stabilize the polymerase-template complex. Similarly, US20150368626 provides methods for performing nucleic acid sequencing that includes contacting a polymerase with a nucleic acid template in the presence of one or more nucleotides.

Surprisingly, Applicant has determined that, at high concentrations of salt, nucleotides affect the formation of the polymerase-template complex by interfering with the binding of template to the polymerase (Example 4). Additionally, Applicant has determined that binding of template to polymerase in the presence of nucleotides (at other than very low concentrations) increase the dissociation rate of template from the polymerase (Example 5 and 10). The effect of nucleotides on the static processivity of the polymerase-template complex is not alleviated by divalent cations such as Ca2+, which is typically included as a stabilizer of polymerase-template complexes.

The destabilizing effect of high levels of nucleotides on the static processivity of the polymerase-template complex is notable for template-dependent synthesis of polynucleotides under conditions that require synthesis to occur at high concentration of salt e.g. nanopore sequencing. In nanopore sequencing, high salt concentrations boost the signal to noise ratio for ionic-current-based nanopore measurements. However, the high salt concentrations destabilize the polymerase-DNA template complex, resulting in high polymerase turnover rates and diminished detection of sequential nucleotide additions i.e. processivity or length of sequence reads, during polymerization reactions is diminished.

Thus, in some embodiments, a method is provided for preparing a polymerase-template complex that comprises providing a polymerase, and contacting the polymerase with a polynucleotide template in a solution comprising a high concentration of salt and being essentially free of nucleotides. The polymerase of the polymerase-template complex can be a wild-type or a variant polymerase that retains polymerase activity at high concentration of salt. Examples of polymerases that find use in the compositions and methods described herein include the salt-tolerant polymerases described elsewhere herein. In some embodiments, the polymerase of the polymerase-template complex is a Pol6 polymerase that has an amino acid sequence that is at least 70% identical to SEQ ID NO:2.

While higher levels of nucleotides adversely affect polymerase-template binding, the Applicant has also surprisingly found that low levels of nucleotides at the time of binding, along with initiating the binding at high temperature, results in improved polymerase-template binding and resultant processivity. For example, the melting temperature of Pol6 is approximately 40° C., and with template bound, the melting temperature is approximately 43° C. By binding polymerase to template at 40° C., the methods and compositions provided herein promote specific binding of polymerase to 3' end and denaturation of polymerase that is unbound or that is bound to non-specific sites on the template. Applicant has also determined that the improved binding is associated with improved extension of the template (Examples 6-10).

Thus, in certain example embodiments, a method is provided for preparing a polymerase-template complex in the presence of low levels of nucleotides and at a high temperature. Additionally, the reaction solution can be saturated with polymerase. The polymerase of the polymerase-template complex can be a wild-type or a variant polymerase that retains polymerase activity at low nucleotide concentrations and at high temperature. In certain example embodiments, the polymerase may also be salt resistant. In some embodiments, the polymerase of the polymerase-template complex is a Pol6 polymerase that has an amino acid sequence that is at least 70% identical to SEQ ID NO:2. Polymerases that are useful in the methods and compositions described herein, as well as other features, uses, and aspects of the invention are described below.

Polymerases of Polymerase-Template Complexes

In certain example embodiments, the polymerase of the polymerase-template complexes described herein can be a DNA polymerase and may include bacterial DNA polymerases, eukaryotic DNA polymerases, archaeal DNA polymerases, viral DNA polymerases, and phage DNA polymerases.

In certain example embodiments, the polymerase of the polymerase-template complex can be a naturally occurring polymerase and any subunit and truncation thereof, mutant polymerase, variant polymerase, recombinant, fusion or otherwise engineered polymerase, chemically modified polymerase, synthetic molecule, and any analogs, homologs, derivatives or fragments thereof that retain the ability to perform template-dependent polynucleotide synthesis. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases.

In some embodiments, the polymerase used to prepare the polymerase-template complex is a salt-tolerant polymerase capable of catalyzing template-dependent DNA synthesis in a solution comprising a high salt concentration and being essentially free of nucleotides. The high salt concentration at which the polymerase-template complex can be formed is defined as a salt concentration of at least 100 mM salt e.g. 100 mM potassium glutamate (K-glu).

Salt-tolerant polymerases can be wild-type or variants of polymerases that are naturally salt-tolerant. In some embodiments, salt-tolerant polymerases are type B DNA polymerases that include members of the extreme halophiles, and variants thereof as described, for example, in US Patent Publication US2014/0113291, entitled "Salt-tolerant DNA polymerases," which is incorporated herein by reference in its entirety.

In other embodiments, salt-tolerant polymerases can be polymerases that are not naturally salt-tolerant, but that have been modified to become salt-tolerant.

In certain example embodiments, and in addition to a slow $k_{off, DNA}$, fast $k_{on, DNA}$, the polymerases of the polymerase-template complex can carry out DNA polymerization at high concentrations of salt, and can have one or more desired characteristic that find use in sequencing DNA, such as slow $k_{off, nucleotide}$, fast $k_{on, nucleotide}$, high fidelity, low exonuclease activity, DNA strand displacement, $k_{chem}$, increased stability, increased processivity, salt tolerance, and compatibility with attachment to nanopore. In certain example embodiments, the polymerases have the ability to incorporate a polyphosphates having 4, 5, 6, 7 or 8 phosphates, such as quadraphosphate, pentaphosphate, polyphosphate, heptaphosphate or octophosphate nucleotide, sequencing accuracy, and long read lengths, i.e., long continuous reads.

In certain example embodiments, the polymerase may be a polymerase that functions at temperatures above room temperature, such as a polymerase that functions above about 30° C. In other example embodiments, the polymerase may function at temperatures of 40° C. or above. Such polymerase may include any of the polymerases described herein that function at such temperatures.

In certain example embodiments, the polymerase of the polymerase-template complex is a polymerase that has been engineered to have increase processivity. Such example polymerases may further include additional modifications that impart or enhance one or more of the desired characteristics of a polymerase for sequencing polynucleotides (e.g. DNA).

In certain example embodiments, the engineered polymerase can be a variant Pol6 polymerase that displays increased processivity when compared to the parental Pol6 from which it is derived. For example, the parental polypeptide is a wild-type Pol6 polypeptide. The variant Pol6 polypeptide of the polymerase-template complex can be derived from a wild-type parental *Clostridium* phage phiCPV4 wild type sequence (SEQ ID NO:1) nucleic acid coding region plus a His-tag; SEQ ID NO:1, protein coding region) and available elsewhere (National Center for Bioinformatics or GenBank Accession Numbers AFH27113). A wild-type parental Pol6 polymerase can be a homolog of the parent Pol6 from *Clostridium* that can be used as a starting point for providing variant polymerases having increased processivity.

As those skilled in the art will appreciate, other polymerases having a high degree of homology to the *Clostrium* phage sp. strain phiCPV4 may serve as a parental Pol6 without defeating the scope of the compositions and methods provided herein. Homologs of the parental Pol6 from *Clostridium* phage can share sequence identity with the Pol6 from *Clostridium* phage (SEQ ID NO:1) of at least 70%, at least 80%, at least 85%, at least 90%, at least 95%, at least 98%, or at least 99%. For example, a variant Pol6 can be derived from a homolog of the *Clostridium* phage that is at least 70% identical to the parental Pol6 from *Clostridium* phage.

In other example embodiments, the variant Pol6 polymerase of the polymerase-template complex is a variant Pol6 polypeptide that can be derived from a variant parental Pol6. In some example embodiments, the variant parental Pol6 polymerase is the Pol6 polymerase of SEQ ID NO:2. In other embodiments, the variant parental Pol6 polymerase comprises modifications that remove/decrease the exonuclease activity of the polymerase (e.g., U.S. Provisional Patent Application 62/301,475, titled "Exonuclease Deficient Polymerases," filed on Feb. 29, 2016, which is expressly incorporated herein by reference). In yet other embodiments, the polymerase can be mutated to reduce the rate at which the polymerase incorporates a nucleotide into a nucleic acid strand (e.g., a growing nucleic acid strand). In some cases, the rate at which a nucleotide is incorporated into a nucleic acid strand can be reduced by functionalizing the nucleotide and/or template strand to provide steric hindrance, such as, for example, through methylation of the template nucleic acid strand. In some instances, the rate is reduced by incorporating methylated nucleotides. In other embodiments, the parental polypeptide is a Pol6 variant to which additional mutations have been introduced to improve the desired characteristics of a polymerase used in nanopore sequencing. In certain example embodiments, the variant Pol6 can share sequence identity with the parental Pol6 of SEQ ID NO:2 of at least 70%, at least 80%, at least 85%, at least 90%, at least 95%, at least 98%, or at least 99%.

In certain example embodiments, the modification of one or more amino acids at the DNA binding site can be one or more of a substitution, a deletion or an insertion, which modification(s) retain the polymerase activity of the variant polymerase, and decrease the rate of dissociation of poly-nucleotide from the Pol-DNA complex relative to that of the parent Pol6. The amino acid modification(s) can be made at one or more of amino acid residues corresponding to amino acid residues V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, E585, T529M, S366A, A547F, N545L, Y225L, and D657R of SEQ ID NO:2.

In some example embodiments, the variant Pol6 enzyme having polymerase activity, comprises an amino acid sequence at least 70% identical to that of the full-length parental Pol6 of SEQ ID NO:2, and has a modification at one or more of amino acids corresponding to amino acid residues V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, E585, T529M, S366A, A547F, N545L, Y225L, and D657R of SEQ ID NO:2.

In some example embodiments, the mutation of one or more amino acids of the DNA binding site is a substitution to a positively charged amino acid. For example, any one or more of amino acids corresponding to amino acid residues V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, and E585 of SEQ ID NO:2 can be mutated to a K, R, H, Y, F, W, and/or T.

In some example embodiments, the mutation of the one or more amino acids of the DNA binding site is a substitution to K. For example, the variant Pol6 polymerase can com-prise amino one or more of amino acid substitutions G438K, E565K, E585K, L731K, and M738K. In some example embodiments the variant Pol6 polymerase comprises sub-stitution E585K. In other example embodiments, the Pol6 polymerase comprises substitutions E585K+L731K. In yet other embodiments, the Pol6 polymerase comprises substitutions E585K+M738K. In other embodiments, at least two, at least three, at least four, at least five, at least six amino acids or more of the DNA binding site are mutated.

In certain example embodiments, the mutation of the one or more amino acids of the DNA binding site is a substitu-tion including one or more of T529M, S366A, A547F, N545L, Y225L, or D657R. For example, the variant poly-merase may include the following substitutions: T529M, S366A, A547F, N545L, Y225L, and D657R. In certain example embodiments, the variant polymerase is an amino acid sequence that is about 70%, 80%, 90%, 95%, 98% or more identical to the amino acid sequence set forth as SEQ ID NO: 14, while retaining one or more of the substitutions identified in SEQ ID NO: 14 (such as retaining all the substitutions identified therein).

In certain example embodiments, the resulting variant Pol6 enzymes retain polymerase activity, and display a decreased rate of dissociation of polynucleotide form the Pol-DNA complex relative to the rate of dissociation dis-played in the parent polymerase that lacks the same muta-tions. In some example embodiments, the modification of the parent Pol6 produces a variant Pol6 polymerase having a rate of dissociation from the template that is at least 2-fold less that of the parent Pol6. Modifications of the parent Pol6 can produce variant Pol6 polymerases having a rate of dissociation from the template that is at least 3-fold less that of the parent Pol6, at least 4-fold less that of the parent Pol6, at least 5-fold less that of the parent Pol6, at least 6-fold less that of the parent Pol6, at least 7-fold less that of the parent Pol6, at least 8-fold less that of the parent Pol6, at least 9-fold less that of the parent Pol6, at least 10-fold less that of the parent Pol6.

DNA sequences encoding a wild-type parent Pol6 may be isolated from any cell or microorganism producing the Pol6 in question, using various methods well known in the art. Examples of DNA sequences that encode wild-type *Clostridium* phage phiCPV4 (i.e. wild-type Pol6), are pro-vided herein as nucleotides 28-2220 of SEQ ID NO:3, and as nucleotides 421 to 2610 of SEQ ID NO:5. In addition to the wild-type Pol6, SEQ ID NO:3 comprises at its 5' end nucleotides that encode a histidine tag (His$_6$; HHHHHH; SEQ ID NO:9). SEQ ID NO:5 comprises at its 5' end nucleotides that encode histidine tag (His$_6$ (SEQ ID NO: 9)) and a SpyCatcher peptide SGDYDIPTTEN-LYFQGAMVDTLSGLSSEQGQSGDMTIEED-SATHIKFSKRDEDGKELA GAT-MELRDSSGKTISTWISDGQVKDFYLYPGKYTFVETAAP-DGYEVATAITFTVNEQG QVTVNGKATKGDAHI (SEQ ID NO:10). In certain example embodiments, any of the polymerase identified herein, including any of the variant polymerases, may be linked directly or indirectly to the SpyCatcher peptide (SEQ ID NO:10).

The DNA sequence may be of genomic origin, mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. (1988).

Formation of Polymerase-Template Complex at High Salt Concentration

In certain example embodiments, the polymerase-tem-plate complex can be formed in the presence of high concentration of salt of at least 100 mM and up to 1 M salt e.g. KCl, K-glu or other monovalent salt. The high concentration of salt can be about 10, 20, 30, 40, 50, 60, 70, 80, 90, 100, 150, 200, 250, 300, 350, 400, 450, 500, 550, 600, 650, 700, 750, 800 mM, 900 mM or greater. Typical salts include salts of metal elements. The high salt solutions can include one or more of a potassium salt, sodium salt, cesium salt, calcium salt, cobalt, nickel, aluminum, manganese, zinc, and lithium. Salts can also include the bicarbonate, sulfate, chloride, carbonate, nitrate, nitrite, bromide, citrate, acetate, cyanide, oxide or phosphate salt of a metal element known to those of skill in the art. In some embodiments, the salt is potassium glutamate (K-glu), potassium chloride (KCl), potassium sulfate ($K_2SO_4$), potassium nitrate ($KNO_3$), cesium chloride (CsCl), or cesium nitrate ($CsNO_3$). In some embodiments, the high salt solution includes K-Glu (potassium glutamate) or other monovalent salt. In addition, a salt useful in the invention can include a mixture or blend of salts. Blends of mineral salts that can be used in the invention include K-Glu and KCl, K-Glu and $K_2SO_4$, K-Glu and $KNO_3$, K-Glu and CsCl, K-Glu and $CsNO_3$, K-Glu and $KNO_3$, K-Glu and CsCl, K-Glu and $CsNO_3$, K-Glu and CsCl, K-Glu and $CsNO_3$, KCl and $K_2SO_4$, KCl and $KNO_3$, KCl and CsCl, KCl and $CsNO_3$, $K_2SO_4$ and $KNO_3$, $K_2SO_4$ and CsCl, $K_2SO_4$ and $CsNO_3$, $KNO_3$ and CsCl, $KNO_3$ and $CsNO_3$, and CsCl and $CsNO_3$. The foregoing salts may be used in the sequencing polymerization reactions at a concentration in the range of 50 to 1M, in the range of 100 to 800 mM, in the range of 200 to 700 mM, in the range of 300 to 600 mM, in the range of 400 to 500 mM. In some embodiments, the high salt concentration can be of at least 150 mM and up to 500 mM. In some embodiments, the high concentration of salt is at least 500 mM salt.

The rate of polymerization of the complexed polymerase e.g. variant Pol6 polymerase, at high salt concentrations is at least 1 base/second, at least 5 bases/second, at least 10 bases/second, at least 20 bases/second, at least 30 bases/second, at least 40 bases/second, at least 50 bases/second, or more. In some embodiments, the rate of polymerization of the complexed polymerase e.g. variant Pol6 polymerase is at least 1 base/second at 100 mM salt, 1 base/second at 200 mM salt, at least 1 base/second at 300 mM salt, at least 1 base/second at 400 mM salt, at least 1 base/second at 500 mM salt, at least 1 base/second at 600 mM salt, at least 1 base/second at 700 mM s alt, at least 1 base/second at 800 mM salt, at least 1 base/second at 800 mM salt, at least 1 base/second at 900 mM salt, at least 1 base/second at 1M salt. In some embodiments, the rate of polymerization of the complexed polymerase e.g. variant Pol6 polymerase is between 1 and 10 bases/second at 100 mM salt, between 1 and 10 bases/second at 200 mM salt, between 1 and 10 bases/second at 300 mM salt, between 1 and 10 bases/second at 400 mM salt, between 1 and 10 bases 600 mM salt, between 1 and 10 bases at 700 mM salt, between 1 and 10 bases/second at 800 mM salt, between 1 and 10 bases/second at 800 mM salt, between 1 and 10 bases/second at 900 mM salt, or between 1 and 10 bases/second at 1M salt.

In some embodiments, the solution for preparing a polymerase-template complex comprising a high concentration of salt further comprises a polymerase-template complex stabilizer. Examples of polymerase-template complex stabilizers include without limitation $Ca^{2+}$. Thus, in some embodiments, the solution that is provided for preparing a polymerase-template complex comprises, for example, a high concentration of salt of between 100 mM and 500 mM K-glu. Solutions for preparing polymerase-template complexes are essentially free of nucleotides.

Formation of a polymerase-template complex can be assayed according to various methods known in the art. For example, formation of the polymerase-template complex can be determined according to the method described in Example 3.

Thus, in some embodiments, a method is provided for preparing a polymerase-template complex that comprises providing a polymerase, and contacting the polymerase with a polynucleotide template in a solution comprising a high concentration of salt and being essentially free of nucleotides. The polymerase of the polymerase-template complex can be a wild-type or a variant polymerase that retains polymerase activity at high concentration of salt. Examples of polymerases that find use in the compositions and methods described herein include the salt-tolerant polymerases described elsewhere herein. In some embodiments, the polymerase of the polymerase-template complex is a Pol6 polymerase that has an amino acid sequence that is at least 70% identical to SEQ ID NO:2.

Formation of Polymerase-Template Complexes at High Temperature and Low Nucleotide Concentration In certain example embodiments, the polymerase-template complex can be formed in the presence of high temperature, along with low concentrations of nucleotides. For example, in certain example embodiments provided is a method for preparing a polymerase-template complex, the method including (a) providing a polymerase and (b) contacting the polymerase with a polynucleotide template in a solution that includes a low concentration of nucleotides and that is at a high temperature, thereby preparing the polymerase-template complex.

With regard to temperature, for example, the temperature of the solution for forming the polymerase-template complex can be above room temperature, i.e, above about 20° C. For example, the high temperature may be about 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., or more. In certain example embodiments, the high temperature is 38° C., 39° C., 40° C., 41° C., or 42° C. In certain example embodiments, the high temperature is at or near the melting temperature of the polymerase or the polymerase-template complex.

While in certain example embodiments described herein the reaction solution in which the polymerase-template complex is formed includes high salt and is essentially free of nucleotides, in other example embodiments the solution includes a low concentration of nucleotides. For example, the low nucleotide concentration may range from 0.5 µM to 2.5 µM. In other example embodiments, the nucleotide concentration is 0.8 µM to 2.2 µM, such as about 0.8 µM, 0.9 µM, 1.0 µM, 1.1 µM, 1.2 µM, 1.3 µM, 1.4 µM, 1.5 µM, 1.6 µM, 1.7 µM, 1.8 µM, 1.9 µM, 2.0 µM, 2.1 µM, or 2.2 µM. In addition to the low concentration of nucleotides, the solution can include the high temperature as described herein. As an example, the reaction solution in which the polymerase-template is formed may include the template, nucleotides at a concentration of about 0.8 µM to 2.2 µM, with the solution being about 38° C. to 42° C.

To facilitate binding of the polymerase to the template, the polymerase may, in certain example embodiments, be equal to the template concentration or be in molar excess of the template concentration. For example, the polymerase may be 1×, 2×, 3×, 4×, 5×, 6×, 7×, 8×, 9×, 10× or more of the template concentration. In other words, in certain example embodiments, the reaction solution can be saturated with polymerase.

Examples of polymerases of the polymerase-complex that find use in the compositions and methods described herein include the various polymerases described herein. These include, for example, any of the high-temperature-suitable polymerases described herein, as well as the variant polymerases described herein. In certain example embodiments, such as those described in the Examples 10-14, the polymerase includes the sequence set forth as SEQ ID NO: 14. In other example embodiments, the polymerase of the complex has at least 70% or more identity to the amino acid sequence set forth as SEQ ID NO: 2. In certain example embodiments, the polymerase, or variant polymerase, can be linked directly or indirectly to the SpyCatcher peptide (SEQ ID NO:10) to form a fusion peptide. As an example, the sequence set forth as SEQ ID NO: 14, or a sequence having 70% or more identity thereto, may be joined, directly or indirectly, to the sequence set forth as SEQ ID NO:10. The polymerase and SpyCatcher peptide may be joined, for example, by any linker peptide known in the art.

To form the polymerase complex, for example, the polymerase, template, and nucleotides are brought in contact with each other in a reaction solution at the desired temperature. The complexes are then allowed to form in the solution. For example, the reaction solution may be incubated for about 10, 15, 20, 25, 30 minutes or more before sequencing is initiated. Once the polymerase-template complexes are formed and sequencing is initiated, for example, additional nucleotides may be added to the solution, thereby raising the concentration of the nucleotides in the solution. That is, once sequencing is initiated, it is not necessary to maintain the low concentration of nucleotides to achieve the several benefits described herein, e.g., increased polymerase-template complex formation and enhanced processivity. For example, the concentration of the nucleotides may be raised to about 5 μM, 6 μM, 7 μM, 8 μM, 9 μM, 10 μM, 11 μM, 12 μM, 13 μM, 14 μM, or 15 μM. In certain example embodiments, the reaction solution may also include a high salt solution as described herein.

Like the evaluation of polymerase-template complex formation with increased salt, the formation of the polymerase-template complex can be assayed according to various methods known in the art. For example, formation of the polymerase-template complex can be determined according to the method described in Example 3 (i.e., using a FRET assay). Using the methods and compositions described herein, for example, formation of the polymerase-template complex may be increased by about 10%, 15%, 20%, 20%, 25%, 30%, 35%, 40%, 45%, 50% or more compared to a control that lacks low nucleotides and/or that is ran at or below room temperature.

In certain example embodiments, provided herein is a method for increasing processivity of a template-polymerase complex, the method comprising forming a polymerase-template complex in a solution comprising a low concentration of nucleotides as described herein and having a high temperature as described herein. The solution can also be saturated with polymerase. The processivity of the polymerase-template complex formed in the high-temperature solution and low nucleotide solution is greater than a processivity resulting from a control polymerase-template complex solution at room temperature. For example, using the methods and compositions described herein, processivity may be increased by about 10%, 15%, 20%, 20%, 25%, 30%, 35%, 40%, 45%, 50% or more compared to a control that lacks low nucleotides and/or that is ran at or below room temperature.

Template Polynucleotides

The methods and compositions provided herein are applicable to various different kinds of nucleic acid templates, nascent strands, and double-stranded products, including single-stranded DNA; double-stranded DNA; single-stranded RNA; double-stranded RNA; DNA-RNA hybrids; nucleic acids comprising modified, missing, unnatural, synthetic, and/or rare nucleosides; and derivatives, mimetics, and/or combinations thereof.

The template nucleic acids of the invention can comprise any suitable polynucleotide, including double-stranded DNA, single-stranded DNA, single-stranded DNA hairpins, DNA/RNA hybrids, RNAs with a recognition site for binding of the polymerizing agent, and RNA hairpins. Further, target polynucleotides may be a specific portion of a genome of a cell, such as an intron, regulatory region, allele, variant or mutation; the whole genome; or any portion thereof. In other embodiments, the target polynucleotides may be, or be derived from mRNA, tRNA, rRNA, ribozymes, antisense RNA or RNAi.

The template nucleic acids of the invention can include unnatural nucleic acids such as PNAs, modified oligonucleotides (e.g., oligonucleotides comprising nucleotides that are not typical to biological RNA or DNA, such as 240-O-methylated oligonucleotides), modified phosphate backbones and the like. A nucleic acid can be e.g., single-stranded or double-stranded.

The nucleic acids used to produce the template nucleic acids in the methods herein (the target nucleic acids) may be essentially any type of nucleic acid amendable to the methods presented herein. In some cases, the target nucleic acid itself comprises the fragments that can be used directly as the template nucleic acid. Typically, the target nucleic acid will be fragmented and further treated (e.g. ligated with adaptors and or circularized) for use as templates. For example, a target nucleic acid may be DNA (e.g., genomic DNA, mtDNA, etc.), RNA (e.g., mRNA, siRNA, etc.), cDNA, peptide nucleic acid (PNA), amplified nucleic acid (e.g., via PCR, LCR, or whole genome amplification (WGA)), nucleic acid subjected to fragmentation and/or ligation modifications, whole genomic DNA or RNA, or derivatives thereof (e.g., chemically modified, labeled, recoded, protein-bound or otherwise altered).

The template nucleic acid may be linear, circular (including templates for circular redundant sequencing (CRS)), single- or double-stranded, and/or double-stranded with single-stranded regions (e.g., stem- and loop-structures). The template nucleic acid may be purified or isolated from an environmental sample (e.g., ocean water, ice core, soil sample, etc.), a cultured sample (e.g., a primary cell culture or cell line), samples infected with a pathogen (e.g., a virus or bacterium), a tissue or biopsy sample, a forensic sample, a blood sample, or another sample from an organism, e.g., animal, plant, bacteria, fungus, virus, etc. Such samples may contain a variety of other components, such as proteins, lipids, and non-target nucleic acids. In certain embodiments, the template nucleic acid is a complete genomic sample from an organism. In other embodiments, the template nucleic acid is total RNA extracted from a biological sample or a cDNA library.

In addition to increasing the processivity of the polymerase-template complex at concentrations of high salt, it is contemplated that the methods and compositions provided herein can be used to offset the negative effects on the formation of polymerase-template complex resulting from sub-optimal concentrations of cofactors, sub-optimal pH levels and/or temperatures, or that include the presence of chemical or biological inhibitors other than the requisite nucleotides required for polynucleotide synthesis. For example, the polymerase-template complex can be formed at a suboptimal pH and/or temperature in the absence of nucleotides.

The polymerase-template complex prepared according to the methods provided herein can be utilized in template-dependent DNA synthesis methods including DNA amplification, and template-dependent DNA sequencing.

In some embodiments, a method is provided for performing template-dependent DNA synthesis comprising (a) providing a polymerase-template complex in a solution comprising a high concentration of salt and being essentially free of nucleotides; and (b) initiating the template-dependent DNA synthesis by adding nucleotides to the solution. In other example embodiments, a method is provided for performing template-dependent DNA synthesis that includes (a) providing a polymerase-template complex in a solution comprising a low nucleotide concentration, the solution being at a high temperature, and (b) thereafter initiating the template-dependent DNA synthesis by adding nucleotides to the solution.

The polymerase of the polymerase-template complex can be a wild-type or a variant polymerase that retains polymerase activity at high concentration of salt and/or high temperature. Examples of polymerases that find use in the compositions and methods described herein include the salt-tolerant and temperature-tolerant polymerases described elsewhere herein. In some embodiments, the polymerase of the polymerase-template complex is a Pol6 polymerase that has an amino acid sequence that is at least 70% identical to SEQ ID NO:2. In some embodiments, the high concentration of salt is greater than 100 mM e.g. greater than 100 mM K-glu.

As described in reference to FIG. 1, processivity of the polymerase can be increased by increasing the static processivity of the complexed polymerase and/or increasing the replicative processivity of the complexed polymerase. In some embodiments, a method is provided for increasing the static processivity of a polymerase-template complex by forming a polymerase-template complex in a solution comprising a high concentration of salt and being essentially free of nucleotides. The increase in processivity of the polymerase-template complex when prepared in the presence of a high concentration of salt in the absence of nucleotides is greater than the processivity of the polymerase-template complex when prepared in the same high concentration of salt and in the presence of nucleotides. In some embodiments, the processivity is increased by a faster rate of association of polymerase with template, and/or by a slower rate of dissociation of the polymerase from the template. The high concentration of salt can be greater than 100 mM e.g. greater than 100 mM K-glu.

In some embodiments, a method is provided for increasing the static processivity of a polymerase-template complex by forming a polymerase-template complex in a solution comprising a low concentration of nucleotides and a high temperature. Additionally, the solution may be saturated with polymerase as described herein. The increase in processivity of the polymerase-template complex when prepared in such a solution is greater than the processivity of the polymerase-template complex when prepared in a solution at room temperature and containing high concentrations of nucleotides.

Nanopore Sequencing Complexes—Attachment of Polymerase to Nanopore

Nanopore sequencing with the aid of a polymerase is accomplished by nanopore sequencing complexes, which are formed by linking the polymerase-template complex to a nanopore. In some embodiments, the polymerase-template complex is subsequently linked to a nanopore to form the nanopore sequencing complex, which is subsequently inserted into a lipid bilayer. In other embodiments, the nanopore is first inserted into a lipid bilayer, and the polymerase-template complex is subsequently attached to the nanopore. Methods for assembling nanopore sequencing complexes are described in U.S. Provisional Application No. 62/281,719 filed on Jan. 21, 2016, titled "Nanopore Sequencing Complexes," which is incorporated herein by reference in its entirety.

Measurements of ionic current flow through a nanopore are made across a nanopore that has been reconstituted into a lipid membrane. In some instances, the nanopore is inserted in the membrane (e.g., by electroporation, by diffusion). The nanopore can be inserted by a stimulus signal such as electrical stimulus, pressure stimulus, liquid flow stimulus, gas bubble stimulus, sonication, sound, vibration, or any combination thereof. In some cases, the membrane is formed with aid of a bubble and the nanopore is inserted in the membrane with aid of an electrical stimulus. In other embodiments, the nanopore inserts itself into the membrane. Methods for assembling a lipid bilayer, forming a nanopore in a lipid bilayer, and sequencing nucleic acid molecules can be found in PCT Patent Publication Nos. WO2011/097028 and WO2015/061510, which are incorporated herein by reference in their entirety.

The polymerase-template complex can be attached to the nanopore before the nanopore being inserted into the lipid membrane or following the insertion of the nanopore into the lipid membrane. In certain example embodiments, the polymerase is attached to the nanopore, such as to one or more of monomers of alpha-hemolysin, and the template is added thereafter to form the polymerase-template complex.

The nanopores of the nanopore sequencing complex include without limitation biological nanopores, solid state nanopores, and hybrid biological-solid state nanopores. Biological nanopores of the Pol6 nanopore sequencing complexes include OmpG from *E. coli*, sp., *Salmonella* sp., *Shigella* sp., and *Pseudomonas* sp., and alpha hemolysin from *S. aureus* sp., MspA from *M. smegmatis* sp. The nanopores may be wild-type nanopores, variant nanopores, or modified variant nanopores.

Variant nanopores can be engineered to possess characteristics that are altered relative to those of the parental enzyme. See, for example, U.S. patent application Ser. No. 14/924,861 filed Oct. 28, 2015, entitled "alpha-Hemolysin Variants with Altered Characteristics," which is incorporated herein by reference in its entirety.

Other variant nanopores are described, for example, in U.S. Provisional Patent Application No. 62/357,230, filed on Jun. 30, 2016, titled "Long Lifetime Alpha-Hemolysin Nanopores," which is incorporated herein by reference in its entirety. In other example embodiments, the alpha-hemolysins of an alpha-hemolysin nanopore may be modified as described in U.S. Provisional Patent Application No. 62/316,236, filed on Mar. 31, 2016, titled "Nanopore Protein Conjugates and Uses Thereof," which is incorporated herein by reference in its entirety.

In some example embodiments, the characteristics are altered relative to the wild-type enzyme. In some embodiments, the variant nanopore of the nanopore sequencing complex is engineered to reduce the ionic current noise of the parental nanopore from which it is derived. An example of a variant nanopore having an altered characteristic is the OmpG nanopore having one or more mutations at the constriction site (U.S. Provisional Patent Application No. 62/222,197, entitled "OmpG Variants", filed on Sep. 22, 2015, which is incorporated by reference herein in its entirety), which decrease the ionic noise level relative to that of the parent OmpG. The reduced ionic current noise provides for the use of these OmpG nanopore variants in single molecule sensing of polynucleotides and proteins. In other embodiments, the variant OmpG polypeptide can be further mutated to bind molecular adapters, which while resident in the pore slow the movement of analytes, e.g., nucleotide bases, through the pore and consequently improve the accuracy of the identification of the analyte (Astier et al., J Am Chem Soc 10.1021/ja057123+, published online on Dec. 30, 2005).

Modified variant nanopores are typically multimeric nanopores whose subunits have been engineered to affect intersubunit interaction (U.S. Provisional Patent Application Nos. 62/232,175 and 62/244,852, entitled "Alpha-Hemolysin Variants", filed on Sep. 24, 2015 and Oct. 22, 2015, respectively, which are incorporated by reference herein in their entirety). Altered subunit interactions can be exploited to specify the sequence and order with which monomers oligomerize to form the multimeric nanopore in a lipid bilayer. This technique provides control of the stoichiometry of the subunits that form the nanopore. An example of a multimeric nanopore whose subunits can be modified to determine the sequence of interaction of subunits during oligomerization is an aHL nanopore.

In some example embodiments, a single polymerase is attached to each nanopore. In other embodiments, two or more polymerases are attached to a monomeric nanopore or to a subunit of an oligomeric nanopore.

Means of Attaching

The polymerase-template complex, such as the Pol6-DNA template complex, can be attached to the nanopore in any suitable way. Attaching polymerase-polymer complexes to nanopores may be achieved using the SpyTag/SpyCatcher peptide system (Zakeri et al. PNAS 109:E690-E697 [2012]) native chemical ligation (Thapa et al., Molecules 19:14461-14483 [2014]), sortase system_(Wu and Guo, J Carbohydr Chem 31:48-66 [2012]; Heck et al., Appl Microbiol Biotechnol 97:461-475 [2013]), transglutaminase systems (Dennler et al., Bioconjug Chem 25:569-578 [2014]), formylglycine linkage (Rashidian et al., Bioconjug Chem 24:1277-1294 [2013]), or other chemical ligation techniques known in the art.

The polymerase-template complex can be attached to the nanopore by linking the polymerase portion of the complex to the nanopore. In some instances, the polymerase e.g. variant Pol6 polymerase, is linked to the nanopore using Solulink™ chemistry. Solulink™ can be a reaction between HyNic (6-hydrazino-nicotinic acid, an aromatic hydrazine) and 4FB (4-formylbenzoate, an aromatic aldehyde). In some instances, the polymerase is linked to the nanopore using Click chemistry (available from LifeTechnologies, for example).

In some cases, zinc finger mutations are introduced into the nanopore molecule and then a molecule is used (e.g., a DNA intermediate molecule) to link the Pol6 polymerase to the zinc finger sites on the nanopore e.g. α-hemolysin.

Additionally, polymerase-template complex e.g. Pol6-DNA template complex can be attached to a nanopore, e.g., aHL, OmpG, by means of a linker molecule that is attached to a nanopore at an attachment site. In some cases, polymerase-template complex e.g. Pol6-DNA template complex, is attached to the nanopore with molecular staples. In some instances, molecular staples comprise three amino acid sequences (denoted linkers A, B and C). Linker A can extend from a nanopore monomer, Linker B can extend from the polymerase alone or from the polymerase of the polymerase-DNA complex, and Linker C then can bind Linkers A and B (e.g., by wrapping around both Linkers A and B) and thus linking the polymerase-template complex e.g. Pol6-DNA template complex, to the nanopore. Linker C can also be constructed to be part of Linker A or Linker B, thus reducing the number of linker molecules.

Other linkers that may find use in attaching the variant Pol6 polymerase to a nanopore are direct genetic linkage (e.g., (GGGGS)$_{1-3}$ amino acid linker (SEQ ID NO: 19)), transglutaminase mediated linking (e.g., RSKLG (SEQ ID NO: 20)), sortase mediated linking, and chemical linking through cysteine modifications. Specific linkers contemplated as useful herein are (GGGGS)$_{1-3}$ (SEQ ID NO: 19), K-tag (RSKLG (SEQ ID NO: 20)) on N-terminus, ΔTEV site (12-25), ΔTEV site+N-terminus of SpyCatcher (12-49).

An exemplary method for attaching a polymerase-template complex e.g. Pol6-DNA template complex, to a nanopore in a membrane involves attaching a linker molecule to a nanopore or mutating a nanopore to have an attachment site and then attaching a polymerase-polynucleotide complex to the attachment site or attachment linker. The polymerase-polynucleotide complex is attached to the attachment site or attachment linker after the nanopore is inserted in the membrane. In some cases, a polymerase-polynucleotide complex is attached to each of a plurality of nanopores that are inserted into a membrane and disposed over wells and/or electrodes of a biochip.

In some embodiments, the polymerase of the polymerase-template complex is expressed as a fusion protein that comprises a linker peptide. The polymerase of the polymerase-template complex can be expressed as a fusion protein that comprises a SpyCatcher polypeptide, which can be covalently bound to a nanopore that comprises a SpyTag peptide (Zakeri et al. PNAS 109:E690-E697 [2012]).

A polymerase-template complex e.g. Pol6-DNA template complex, may be attached to a nanopore using methods described, for example, in PCT/US2013/068967 (published as WO2014/074727; Genia Technologies, Inc.), PCT/US2005/009702 (published as WO2006/028508; President and Fellows of Harvard College), and PCT/US2011/065640 (published as WO2012/083249; Columbia University).

Biochips

Nanopores each comprising one or more polymerase-template complex prepared as described herein may be inserted in a membrane, e.g. a lipid bilayer, and disposed adjacent or in proximity to a sensing electrode of a sensing circuit, such as an integrated circuit of a nanopore based sensor, e.g., a biochip. The nanopore may be inserted in a membrane and disposed of a well and/or sensing electrodes in the biochip. Multiple nanopore sensors may be provided as arrays. Biochips and methods for making biochips are described in PCT/US2014/061854 (published as WO2015/061511, Genia Technologies, Inc.), which is herein incorporated by reference in its entirety.

The biochip can comprise nanopores each having a polymerase having increased processivity relative to the parental Pol6. The variant Pol6 can include any of the modifications/substitutions described herein. For example, the variant polymerase may include a modification at one or more amino acid residues corresponding to amino acid residues V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, E585, T529M, S366A, A547F, N545L, Y225L, and D657R of SEQ ID NO:2.

In some example embodiments, the modification is a substitution to amino acid K, R, H, Y, F, W, and/or T. In some embodiments, the substitution is a substitution to K. In some embodiments, the variant Pol6 comprises the substitution E585K. In other embodiments, the variant Pol6 comprises the substitution of two amino acids E585K+L731K. In yet other embodiments, the variant Pol6 comprises the substitution of two amino acids E585K+L731K. In other example embodiments, the variant Pol6 may include one or more substitutions at T529M, S366A, A547F, N545L, Y225L, and/or D657R or combinations thereof. For example, the polymerase variant may include each of the T529M+ S366A+A547F+N545L+Y225L+D657R substitutions. In certain example embodiments, the amino acid substitutions can be made in a parental Pol6 polymerase that comprises a His6 tag (SEQ ID NO: 9) and a SpyCatcher peptide as given in the polymerase of SEQ ID NO:4.

In certain example embodiments, the resulting variant Pol6 polymerases have increased processivity relative to their parental Pol6 polymerase. In some embodiments, the variant Pol6 polymerases have increased processivity at a high salt concentration. In some embodiments, the increased processivity is retained at a high salt concentration of 10, 20, 30, 40, 50, 60, 70, 80, 90, 100, 150, 200, 250, 300, 350, 400, 450, 500, 550, 600, 650, 700, 750, 800 mM or grater. In some embodiments, the increase in processivity is displayed at a high slat concentration of greater than 100 mM. The increase in processivity comprises a decrease in the rate of template dissociation that is at least 2-fold less that of the parent Pol6. Modifications of the parent Pol6 can produce variant Pol6 polymerases having a rate of dissociation from the template that is at least 3-fold less that of the parent Pol6, at least 4-fold less that of the parent Pol6, at least 5-fold less that of the parent Pol6, at least 6-fold less that of the parent Pol6, at least 7-fold less that of the parent Pol6, at least 8-fold less that of the parent Pol6, at least 9-fold less that of the parent Pol6, at least 10-fold less that of the parent Pol6. In some embodiments, the variant Pol6 polymerases have increased processivity at low nucleotide concentrations and at high temperatures. In certain example embodiments, the polymerase has increased processivity at high temperatures, such as above room temperature as described herein.

For embodiments that include an array of nanopores in a membrane, e.g., lipid bilayer, the density of sequencing nanopore complexes can be high. High density arrays are characterized as having a membrane surface that has a density of Pol6 nanopore sequencing complexes greater or equal to about to about 500 nanopore sequencing complexes per 1 mm². In some embodiments, the surface has a density of discrete nanopore sequencing complexes of about 100, about 200, about 300, about 400, about 500, about 600, about 700, about 800, about 900, about 1000, about 2000, about 3000, about 4000, about 5000, about 6000, about 7000, about 8000, about 9000, about 10000, about 20000, about 40000, about 60000, about 80000, about 100000, or about 500000 nanopore sequencing complexes per 1 mm². In some embodiments, the surface has a density of discrete nanopore sequencing complexes of at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 20000, at least about 40000, at least about 60000, at least about 80000, at least about 100000, or at least about 500000 nanopore sequencing complexes per 1 mm².

The nanopore sequencing methods provided herein involve the measuring of a current passing through the pore during interaction with the nucleotide. In some embodiments, sequencing a nucleic acid molecule can require applying a direct current (e.g., so that the direction at which the molecule moves through the nanopore is not reversed). However, operating a nanopore sensor for long periods of time using a direct current can change the composition of the electrode, unbalance the ion concentrations across the nanopore and have other undesirable effects. Applying an alternating current (AC) waveform can avoid these undesirable effects and have certain advantages as described below. The nucleic acid sequencing methods described herein that utilized tagged nucleotides are fully compatible with AC applied voltages and can therefore be used to achieve said advantages.

Suitable conditions for measuring ionic currents through transmembrane protein pores are known in the art and examples are provided herein in the Experimental section. The method is carried out with a voltage applied across the membrane and pore. The voltage used is typically from −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 160 mV to 240 mV. It is possible to increase discrimination between different nucleotides by a pore of the invention by using an increased applied potential. Sequencing nucleic acids using AC waveforms and tagged nucleotides is described in US Patent Publication US2014/0134616 entitled "Nucleic Acid Sequencing Using Tags", filed on Nov. 6, 2013, which is herein incorporated by reference in its entirety. In addition to the tagged nucleotides described in US2014/0134616, sequencing can be performed using nucleotide analogs that lack a sugar or acyclic moiety e.g. (S)-Glycerol nucleoside triphosphates (gNTPs) of the four common nucleobases: adenine, cytosine, guanine, and thymidine (Horhota et al. Organic Letters, 8:5345-5347 [2006]).

Methods for Sequencing Polynucleotides

As described elsewhere herein, the molecules being characterized using the variant Pol6 polymerases of the Pol6 nanopore sequencing complexes described herein can be of various types, including charged or polar molecules such as charged or polar polymeric molecules. Specific examples include ribonucleic acid (RNA) and deoxyribonucleic acid (DNA) molecules. The DNA can be a single-strand DNA (ssDNA) or a double-strand DNA (dsDNA) molecule. Ribonucleic acid can be reversed transcribed then sequenced.

In certain example embodiments, provided are methods for sequencing nucleic acids at high concentrations of salt using the polymerase-template complexes prepared according to the methods provided herein i.e. at high concentrations of salt and in the absence of nucleotides. The polymerase-template complexes are subsequently attached to a nanopore to form a nanopore sequencing complex, which detects polynucleotide sequences. In other example embodiments, provided are methods for sequencing nucleic acids using the polymerase-template complexes prepared according to the methods provided herein, such as forming the polymerase-template complexes using low nucleotide concentrations, at high temperatures, and in the presence of excess polymerase. The polymerase-template complexes are subsequently attached to a nanopore to form a nanopore sequencing complex, which detects polynucleotide sequences.

The nanopore sequencing complexes comprising polymerase-template complexes prepared according to the compositions and methods provided herein, can be used for determining the sequence of nucleic acids at high concentrations of salt using other nanopore sequencing platforms known in the art that utilize enzymes in the sequencing of polynucleotides. Likewise, the nanopore sequencing complexes comprising polymerase-template complexes prepared according to the compositions and methods provided, can be used for determining the sequence of nucleic acids at, for example, high temperatures using other nanopore sequencing platforms known in the art that utilize enzymes in the sequencing of polynucleotides. For example, nanopore sequencing complexes comprising the polymerase-template complexes prepared according to the methods described herein can be used for sequencing nucleic acids according to the helicase and exonuclease-based methods of Oxford Nanopore (Oxford, UK), Illumina (San Diego, CA), and the nanopore sequencing-by-expansion of Stratos Genomics (Seattle, WA).

In some example embodiments, sequencing of nucleic acids comprises preparing nanopore sequencing complexes comprising polymerase-template complexes prepared according to the methods described herein, and determining polynucleotide sequences at high concentrations of salt using tagged nucleotides as is described in PCT/US2013/068967 (entitled "Nucleic Acid Sequencing Using Tags" filed on Nov. 7, 2013, which is herein incorporated by reference in its entirety). For example, a nanopore sequencing complex that is situated in a membrane (e.g., a lipid bilayer) adjacent to or in sensing proximity to one or more sensing electrodes, can detect the incorporation of a tagged nucleotide by a polymerase at a high concentration of salt as the nucleotide base is incorporated into a strand that is complementary to that of the polynucleotide associated with the polymerase, and the tag of the nucleotide is detected by the nanopore. The polymerase-template complex can be associated with the nanopore as provided herein.

Tags of the tagged nucleotides can include chemical groups or molecules that are capable of being detected by a nanopore. Examples of tags used to provide tagged nucleotides are described at least at paragraphs [0414] to [0452] of PCT/US2013/068967. Nucleotides may be incorporated from a mixture of different nucleotides, e.g., a mixture of tagged dNTPs where N is adenosine (A), cytidine (C), thymidine (T), guanosine (G) or uracil (U). Alternatively, nucleotides can be incorporated from alternating solutions of individual tagged dNTPs, i.e., tagged dATP followed by tagged dCTP, followed by tagged dGTP, etc. Determination of a polynucleotide sequence can occur as the nanopore detects the tags as they flow through or are adjacent to the nanopore, as the tags reside in the nanopore and/or as the tags are presented to the nanopore. The tag of each tagged nucleotide can be coupled to the nucleotide base at any position including, but not limited to a phosphate (e.g., gamma phosphate), sugar or nitrogenous base moiety of the nucleotide. In some cases, tags are detected while tags are associated with a polymerase during the incorporation of nucleotide tags. The tag may continue to be detected until the tag translocates through the nanopore after nucleotide incorporation and subsequent cleavage and/or release of the tag. In some cases, nucleotide incorporation events release tags from the tagged nucleotides, and the tags pass through a nanopore and are detected. The tag can be released by the polymerase, or cleaved/released in any suitable manner including without limitation cleavage by an enzyme located near the polymerase. In this way, the incorporated base may be identified (i.e., A, C, G, T or U) because a unique tag is released from each type of nucleotide (i.e., adenine, cytosine, guanine, thymine or uracil). In some situations, nucleotide incorporation events do not release tags. In such a case, a tag coupled to an incorporated nucleotide is detected with the aid of a nanopore. In some examples, the tag can move through or in proximity to the nanopore and be detected with the aid of the nanopore.

Thus, in one aspect, a method is provided for sequencing a polynucleotide from a sample, e.g. a biological sample, with the aid of a nanopore sequencing complex at a high concentration of salt. The sample polynucleotide is combined with the polymerase in a solution comprising a high concentration of salt and being essentially free of nucleotides to provide the polymerase-template complex portion of the nanopore sequencing complex. In one embodiment, the sample polynucleotide is a sample ssDNA strand, which is combined with a DNA polymerase to provide a polymerase-DNA complex e.g. a Pol6-DNA complex.

In some embodiments, nanopore sequencing of a polynucleotide sample is performed by providing a polymerase-template complex e.g. Pol6-template or variant Pol6-template complex in a solution comprising a high concentration of salt e.g. greater than 100 mM, and being essentially free of nucleotides; attaching the polymerase-template complex to a nanopore to form a nanopore-sequencing complex; and providing nucleotides to initiate template-dependent strand synthesis. The nanopore portion of the sequencing complex is positioned in the membrane adjacent to or in proximity of a sensing electrode, as described elsewhere herein. The resulting nanopore sequencing complex is capable of determining the sequence of nucleotide bases of the sample DNA at a high concentration of salt as described elsewhere herein. In other embodiments, the nanopore sequencing complex determines the sequence of double stranded DNA. In other embodiments, the nanopore sequencing complex determines the sequence of single stranded DNA. In yet other embodiments, nanopore sequencing complex determines the sequence of RNA by sequencing the reverse transcribed product.

In some embodiments, a method is provided for nanopore sequencing at a high salt concentration. The method comprises (a) providing a polymerase-template complex in a solution comprising a high concentration of salt e.g. at least 100 mM, and being free of nucleotides; (b) combining the polymerase-template complex with a nanopore to form a nanopore-sequencing complex; (c) providing tagged nucleotides to the nanopore sequencing complex to initiate template-dependent nanopore sequencing in a high salt concentration of at least 100 mM salt; and (d) detecting with the aid of the nanopore, a tag associated with each of the tagged nucleotides during incorporation of each of the nucleotides to determine that sequence of the template. The polymerase of the polymerase-template complex can be a wild-type or a variant polymerase that retains polymerase activity at high concentration of salt. Examples of polymerases that find use in the compositions and methods described herein include the salt-tolerant polymerases described elsewhere herein. In some embodiments, the polymerase of the polymerase-template complex is a Pol6 polymerase that has an amino acid sequence that is at least 70% identical to SEQ ID NO:2.

In some embodiments, a method for nanopore sequencing a nucleic acid sample is provided. The method comprises using nanopore sequencing complexes comprising the variant Pol6 polymerases provided herein. In one embodiment, the method comprises providing tagged nucleotides to a Pol6 nanopore sequencing complex, and under high salt conditions, carrying out a polymerization reaction to incorporate the nucleotides in a template-dependent manner, and detecting the tag of each of the incorporated nucleotides to determine the sequence of the template DNA.

In one embodiment, tagged nucleotides are provided to a Pol6 nanopore sequencing complex comprising a variant Pol6 polymerase provided herein, and under conditions of high salt, carrying out a polymerization reaction with the aid of the variant Pol6 enzyme of said nanopore sequencing complex, to incorporate tagged nucleotides into a growing strand complementary to a single stranded nucleic acid molecule from the nucleic acid sample; and detecting, with the aid of nanopore, a tag associated with said individual tagged nucleotide during incorporation of the individual tagged nucleotide, wherein the tag is detected with the aid of said nanopore while the nucleotide is associated with the variant Pol6 polymerase.

In one aspect, a method is provided for sequencing a polynucleotide from a sample, e.g. a biological sample, with the aid of a nanopore sequencing complex at a high temperature and at a low concentration of nucleotides. For example, the sample polynucleotide is combined with the polymerase in a solution having a high temperature and having a low concentration of nucleotides. In one embodiment, the sample polynucleotide is a sample ssDNA strand, which is combined with a DNA polymerase to provide a polymerase-DNA complex e.g. a Pol6-DNA complex. The temperature may be above room temperature, such as at about 40° C., as described herein. The nucleotide concentration, for example, may be about 1.2 μM, as described herein. Further, the solution may include a high concentration of the polymerase, such as being saturated with the polymerase. The polymerase can be a variant polymerase as described herein.

In certain example aspects, a method is provided for nanopore-based sequencing of a polynucleotide template. The method includes forming a polymerase-template complex, as described herein, in a solution including a low concentration of nucleotides, the solution having a high temperature, such as above room temperature. For example, the temperature may be about 40° C., as described herein. The method includes combining the formed polymerase-template complex with a nanopore to form a nanopore-sequencing complex. Tagged nucleotides can then be provided to the nanopore sequencing complex to initiate template-dependent nanopore sequencing of the template at the high temperature. With the aid of the nanopore, a tag associated with each of the tagged nucleotides during incorporation of each of the tagged nucleotides while each of the tagged nucleotides is associated with the polymerase is detected, thereby determining the sequence of the polynucleotide template. In certain examples, forming the polymerase-template complex includes saturating the solution with the polymerase of the polymerase-template complex. The nucleotide concentration can be 0.8 μM to 2.2 μM, such as about 1.2 μM. The temperature, for example, can be about 35° C. to 45° C., such as about 40° C.

Other embodiments of the sequencing method that comprise the use of tagged nucleotides with the present nanopore sequencing complexes for sequencing polynucleotides are provided in WO2014/074727, which is incorporated herein by reference in its entirety.

Sequencing nucleic acids using AC waveforms and tagged nucleotides is described in US Patent Publication US2014/0134616 entitled "Nucleic Acid Sequencing Using Tags", filed on Nov. 6, 2013, which is herein incorporated by reference in its entirety. In addition to the tagged nucleotides described in US2014/0134616, sequencing can be performed using nucleotide analogs that lack a sugar or acyclic moiety, e.g., (S)-Glycerol nucleoside triphosphates (gNTPs) of the five common nucleobases: adenine, cytosine, guanine, uracil, and thymidine (Horhota et al. Organic Letters, 8:5345-5347 [2006]).

Reagents, Storage Solutions, and Kits

Sequencing reagents for DNA sequencing or amplification e.g. nanopore sequencing are also provided, the reagent(s) comprising a polymerase-template complex in a solution comprising a high concentration of salt and being essentially free of nucleotides. In certain example embodiments, the reagent(s) include a polymerase and template in a solution with low levels of nucleotides, where the solution can be warmed to a high temperature as described herein to initiate and/or enhance formation of the polymerase-template complex. In such embodiments, the solution can be saturated with polymerase. In some embodiments, the polymerase of the polymerase-template complex comprises a polymerase that is a wild-type or a variant polymerase that retains polymerase activity at high concentration of salt e.g. Pol6 of any one of SEQ ID NOs: 1, 2, 4, 6, 7, 8 and 14. Examples of polymerases that find use in the compositions and methods described herein include the salt-tolerant and/or high-temperature tolerant polymerases described elsewhere herein. In some embodiments, the polymerase of the polymerase-template complex is a Pol6 polymerase that has an amino acid sequence that is at least 70% identical to SEQ ID NO:2.

In some embodiments, the polymerase of the polymerase-template complex is a Pol6 polymerase that has an amino acid sequence having at least 70% identity to full-length parent polypeptide of SEQ ID NO:2 and comprises one or more amino acid substitutions of amino acid residues corresponding to amino acids V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E565, E566, D568, L569, I570, M571, D572, N574, G575, L576, L577, T578, F579, T580, G581, S582, V583, T584, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, and E585, T529M, S366A, A547F, N545L, Y225L, and D657R of SEQ ID NO:2. In some embodiments, the amino acids substitution(s) is to K, R, Y, F, W, and/or T. In some embodiments, the sequencing reagent comprises the variant Pol6 polymerase of SEQ ID NO:6, SEQ ID NO:7, SEQ ID NO:8, and/or SEQ ID NO: 14. In some embodiments, the sequencing reagent comprises a polynucleotide encoding any one of the variant salt tolerant or heat-tolerant Pol6 polymerases provided herein.

In another example embodiment, a storage solution is provided. The storage solution comprises a polymerase-template complex in a solution comprising a high concentration of salt. In some embodiments, the high concentration of salt is greater than 100 mM salt e.g. greater than 100 mM K-glu. In another example embodiment, the storage solution includes a polymerase and template in a solution with low levels of nucleotides, where the solution can be warmed to a high temperature as described herein to initiate and/or enhance formation of the polymerase-template complex. The storage solution, for example, can be saturated with polymerase.

In another aspect, a kit including a sequencing reagent for DNA sequencing is provided. In some embodiments, the kit comprises a polymerase-template complex in a solution comprising a high concentration of salt and being free of nucleotides. In some embodiments, the kit further comprises a buffer and/or nucleotides. I certain example embodiments, the kit includes a polymerase and template in a solution with low levels of nucleotides, where the solution can be warmed to a high temperature as described herein to initiate and/or enhance formation of the polymerase-template complex. In such embodiments, the solution can be saturated with polymerase. The solution of the kit may also include a buffer. The polymerase of the kits can, for example, be a wild type polymerase or a variant polymerase, such any of the variant polymerases described herein.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds).

EXAMPLES

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1: Directed Mutagenesis

Pol6 Mutants

DNA of SEQ ID NO: 3 encoding the WT-Pol6 (SEQ ID NO: 2) was purchased from a commercial source (DNA 2.0, Menlo Park, California). The sequence was verified by sequencing.

Site directed mutagenesis was performed to mutate one or more amino acids of the putative nucleotide/DNA binding site of parental variant Pol6-44-X1 (SEQ ID NO:4). Pol6-44-X1 was derived from wild-type Pol6 to comprise the following substitutions: S366A T529M A547F D44A (SEQ ID NO:4). Pol6-67-X2 was derived from wild-type Pol6 to comprise the following mutations: S366A T529M A547F N545L Y225L D657R Y242A (see SEQ ID NO: 14).

The Pol6 variants like 44-X1 were expressed as a fusion protein having an N-terminal His-tag (see underlined sequence in SEQ ID NO:4) and SpyCatcher domain (bolded italic sequence in SEQ ID NO:4).

Mutagenesis Protocol

The primers for each mutagenesis reaction were designed using the NEB base changer protocol and ordered in 96-well plate format from IDT.

The forward and reverse primers were 5' phosphorylated in high throughput (HTP) format using the T4 polynucleotide kinase (PNK) purchased from NEB. A typical 25-μl reaction contained 15 μl of primer at 10 μM, 5 μl of 5× reaction buffer (from NEB), 1.25 μl PNK enzyme, 3.75 μl water. The reaction was performed at 37° C. for 30 min and the enzyme heat inactivated at 65° C. for 20 min.

PCR mutagenesis was performed using Q5 DNA polymerase from NEB. A typical 25 μl reaction contained 5 μl of Q5 buffer, 5 μl of GC enhancer, 0.5 ul of 10 mM dNTPs, 1.25 μl of 10 μM phosphorylated mutagenesis primers forward and reverse, 0.25 μl Q5 polymerase and 1 μl of 5 ng/ml wild type Pol6 template, i.e., His-Pol6, and 10.75 μl H$_2$O.

Once PCR was completed, 0.5 μl of Dpn1 was added to 25 μl PCR mix and incubated at 37° C. for 1 hr. Then, 2.5 μl of Blunt/TA ligase master mix were added to 2.5 μl of Dpn1 treated PCR product, and the reaction mixture was incubated at room temperature for 1 hr. Thereafter, 1 μl of ligation mix was added to 20 ul of 96-well BL21DE3 cells (EMD Millipore) and incubated on ice for 5 min.

The cells were heat shocked at 42° C. for exactly 30 sec using the PCR thermocycler and placed on ice for 2 min. Thereafter, 80 μl of SOC were added to the cells, which were then incubated at 37° C. for 1 hr without shaking. A 100p aliquot of SOC or ultra-pure water were added to the cells, which were then plated on 48-well LB-agar plates comprising 50-100 μg/ml kanamycin. Cells were grown overnight at 37 C.

Example 2: Expression and Purification

Variants of the parental polymerase Pol6-44-X1 (SEQ ID NO:4), and the Pol6-67-X2 (SEQ ID NO: 14) were expressed and purified using a high throughput method as follows.

DNA encoding variants in expression plasmid pD441 vector were transformed into competent *E. coli*, and glycerol stocks of the transformed cells were made. Starting from a tiny pick of the glycerol stock, grow 1 ml starter culture in LB with 0.2% Glucose and 100 μg/ml Kanamycin for approximately 8 hrs. Transfer 25 μl of log phase starter culture into 1 ml of expression media (Terrific Broth (TB) autoinduction media supplemented with 0.2% glucose, 50 mM Potassium Phosphate, 5 mM MgCl2 and 100 μg/ml Kanamycin) in 96-deep well plates. The plates were incubated with shaking at 250-300 rpm for 36-40 hrs at 28° C.

Cells were then harvested via centrifugation at 3200×g for 30 minutes at 4° C. The media was decanted off and the cell pellet resuspended in 200 μl pre-chilled lysis buffer (20 mM Potassium Phosphate pH 7.5, 100 mM NaCl, 0.5% Tween20, 5 mM TCEP, 10 mM Imidazole, 1 mM PMSF, 1× Bug Buster, 100 μg/ml Lysozyme and protease inhibitors) and incubated at room temperature for 20 min with mild agitation. Then, 20 μl was added from a 10× stock to a final concentration of 100 μg/ml DNase, 5 mM MgCl2, 100 μg/ml RNase I and incubated in on ice for 5-10 min to produce a lysate. The lysate was supplemented with 200 μl of 1M Potassium Phosphate, pH 7.5 (Final concentration will be about 0.5M Potassium phosphate in 400 μl lysate) and filtered through Pall filter plates (Part #5053, 3 micron filters) via centrifugation at approximately 1500 rpm at 4 C for 10 minutes. The clarified lysates were then applied to equilibrated 96-well His-Pur Cobalt plates (Pierce Part #90095) and bind for 15-30 min.

The flow through (FT) was collected by centrifugation at 500×G for 3 min. The FT was then washed 3 times with 400 ul of wash buffer 1 (0.5M Potassium Phosphate pH 7.5, 1M NaCl 5 mM TCEP, 20 mM Imidazole+0.5% Tween20). The FT was then washed twice in 400 ul wash buffer 2 (50 mM Tris pH 7.4, 200 mM KCl, 5 mM TCEP, 0.5% Tween20, 20 mM Imidazole).

The Pol6 was eluted using 200 μl elution buffer (50 mM Tris Ph7.4, 200 mM KCl, 5 mM TCEP, 0.5% Tween20, 300 mM Imidazole, 25% Glycerol) and collected after 1-2 min incubation. Reapply eluate to the same His-Pur plate 2-3 times to get concentrated Pol6 in elute. The purified polymerase is >95% pure as evaluated by SDS-PAGE. The protein concentration is ~3 uM (0.35 mg/ml) with a 260/280 ratio of 0.6 as evaluated by Nanodrop.

Example 3: Template Association Experiments

The association of polymerase-template complex was assayed using the ShortCy5Template (/5Cy5/AGA GTG ATA GTA TGA TTA TGT AGA TGT AGG ATT TGA TAT GTG AGT AGC CGA ATG AAA CCT T/iSpC3/TT GGT TTC ATT CGG) (SEQ ID NOS 12 and 21) and the ShortBHQ2Primer (TTT TCA TAA TCA TAC TAT CAC TCT/BHQ2/-3) (SED ID NO: 13).

The association of polymerase-template complex was assayed under the following conditions: (A) 2× Pol6-44X1 polymerase (SEQ ID NO:4) was pre-incubated with 50 nM ShortCy5Template (SEQ ID NOS 12 and 21) in the presence of $Mg^{2+}$ alone for 32, 55, and 85 minutes at which times polynucleotide synthesis was initiated by adding polyphosphate nucleotides; (B) 2× Pol6-44X1 polymerase (SEQ ID NO:4) was pre-incubated with 50 nM ShortCy5Template (SEQ ID NOS 12 and 21) in the presence of polyphosphate nucleotides alone for 32, 55, and 85 minutes at which times polynucleotide synthesis was initiated by adding MgCl2; or (C) 2× Pol6-44X1 polymerase (SEQ ID NO:4) was pre-incubated with 50 nM ShortCy5Template (SEQ ID NOS 12 and 21) in the absence of MgCl2 and polyphosphate nucleotides alone for 32, 55, and 85 minutes at which times polynucleotide synthesis was initiated by adding MgCl2 and polyphosphate nucleotides.

The level of polymerase-template complex formation was measured for each of the three assay conditions at increasing concentration of K-glu: 75 mM K-glu, 150 mM K-glu, and 300 mM K-glu.

The fluorescence in each case was measured after the reactions were initiated using excitation at 648 nm (590-50) nm and emission at 668 nm (675-50) and were measured every 0.1 s for 1 min.

Figure 3:
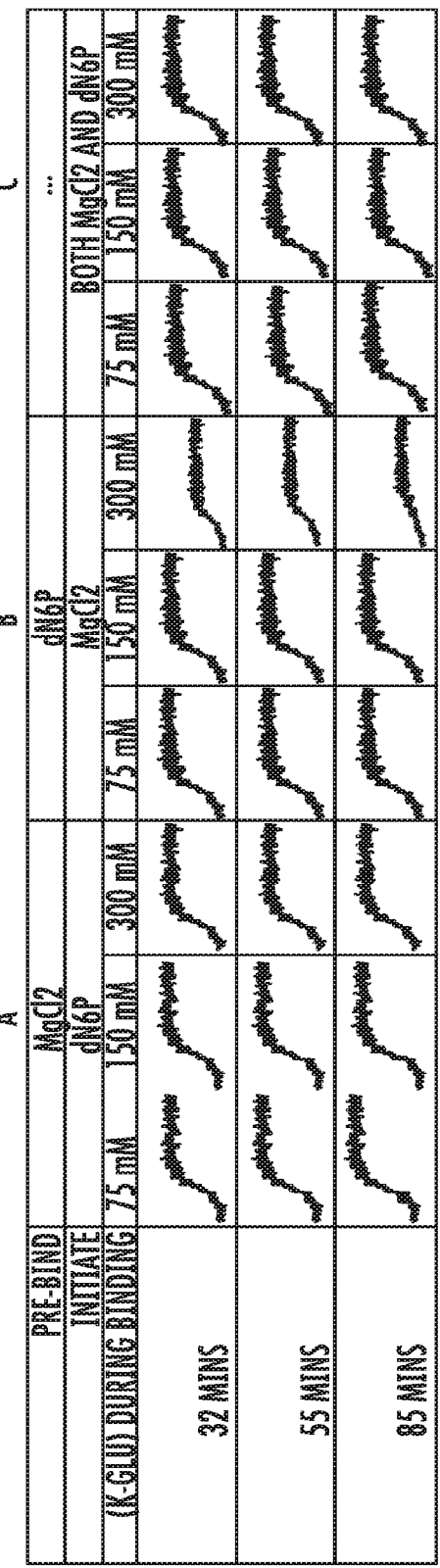
FIG. 3 is a graph showing exemplary results of the effect of forming polymerase-template complex in the presence of polyphosphate nucleotides on the rate of association of template with polymerase at various concentrations of salt. Reference is made to Example 3.
Figure 4A:
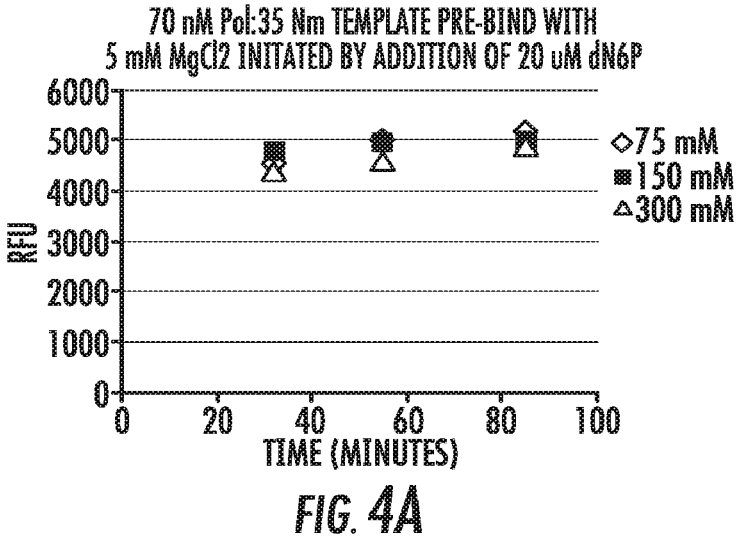
FIGS. 4A-4C is a series of graphs showing association curves for the fluorescence signals shown in FIG. 3. Reference is made to Example 3.
Figure 4B:
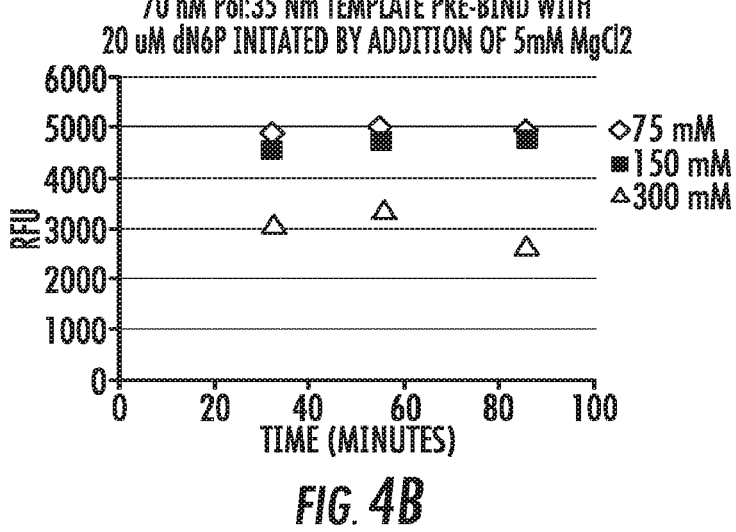
Figure 4C:
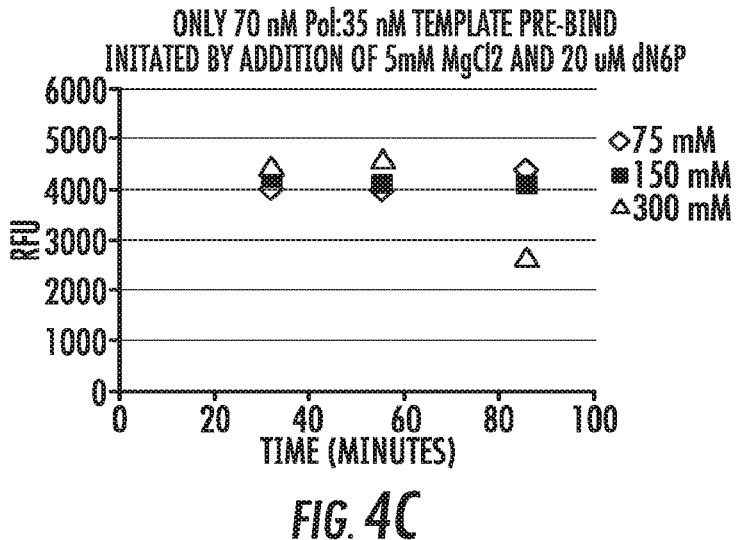

The results are shown in FIG. 3 (A-C) and corresponding FIGS. 4A, 4B, and 4C. More particularly, FIG. 3 shows the fluorescence signal obtained at 32 minutes, 55 minutes and 85 minutes for each of the assay conditions described above. The amplitude of the signal (in RFU) represents the level of DNA-Pol6 complex. Numerical values for the signals' amplitude were calculated and represented in corresponding FIGS. 4A, 4B, and 4C, where FIGS. 4A, 4B, and 4C show the amplitude of fluorescence signal obtained under assay condition A, B, and C, respectively. Diamonds (□) represent signal amplitude measured at 75 mM K-glu, (□) represent signal amplitude measured at 150 mM K-glu, and triangles (Δ) represent signal amplitude measured at 300 mM K-glu.

The data shown in FIGS. 3, 4A, 4B, and 4C demonstrate that the level of polymerase-template complex formed at 75 mM and 150 mM K-glu is independent of the incubation conditions i.e. pre-incubation of DNA with Pol6 in the presence of $Mg_2^+$, alone or when in combination with nucleotides did not affect template binding to Pol6. However, at a high salt concentration of 300 mM K-glu, the binding of DNA to Pol6 was diminished when the complex was allowed to form in the presence of nucleotides alone. The same effect was also seen at a salt concentration of 500 mM K-glu (data not shown).

These data indicate that at high salt concentrations, nucleotides interfere with the binding of DNA template to polymerase, and thereby decrease the level of polymerase-template complex.

Example 4: Template Dissociation Experiments

This example (4.1-4.5) demonstrates the effect of nucleotides on the dissociation of template from the template-polymerase complex.

The effect of divalent metal ions i.e. $Mg_2^+$, and/or nucleotides was determined on the rate of dissociation of template from a polymerase-template complex (koff) at high salt concentration e.g. 500 mM K-glu as follows. Polymerase-template complex was allowed to form in the presence of 75 mM K-glu. At time=0, the concentration of salt was raised to 500 mM, and the subsequent dissociation of the complex was determined at 15, 30, 45, 60, 75, 90, 120, 150, 180, 210, and 240 minutes by initializing polynucleotide synthesis under the following five assay conditions according to the FRET assay described in Example 3.

4.1. Blocked Nucleotides Inhibit Formation of Polymerase-Template Complex

2× concentration of Pol6-44X1 (SEQ ID NO:4) was pre-incubated with ShortCy5Template (SEQ ID NOS 12 and 21) in the presence of 5 mM MgCl2 (A(i)) or in the presence of 5 mM MgCl2+0.1 μM dnpCpp (blocked nucleotide) (A(ii)) at a salt concentration of 75 mM K-glu to allow for the formation of template-DNA complex. At time=0 minutes, salt was added to a final concentration of 500 mM KGlu. Dissociation of template from the template-DNA complex was determined following addition of polyphosphates at various time intervals.

Figures 5A, 5B:
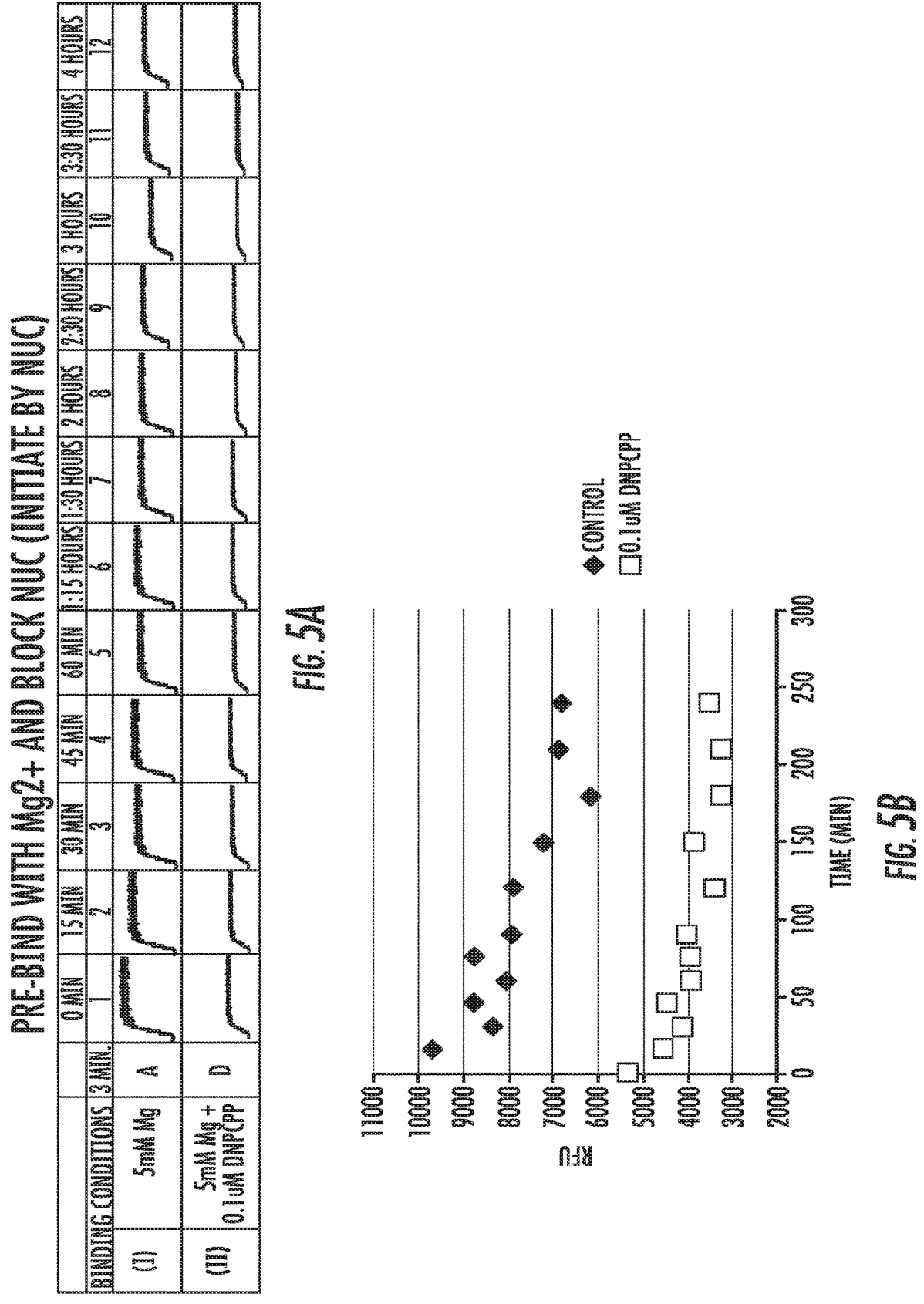
FIGS. 5A-5B is a series of graphs showing results of the effect of blocked nucleotides on inhibiting the formation of polymerase-template complex. Fluorescence signal obtained in a FRET assay are shown in (A), and dissociation curves are shown in (B). Reference is made to Example 4.1.

FIG. 5A shows the fluorescence signal corresponding to the level of polymerase-template complex detected under conditions given in A(i) and A(ii).

FIG. 5B shows a plot of the dissociation of polymerase from the polymerase-template complex when the complex was allowed to form in the presence of $Mg^{2+}$ (♦), or in the presence of 5 mM $Mg^{2+}$+0.1 μM dnpCpp (□). The calculated amplitude of the fluorescence signal shown in 5A (i) and (ii) is plotted in RFU as a function of time.

The data show that blocked nucleotides inhibit binding of template to polymerase.

4.2. Formation of Polymerase-Template Complex in the Presence of Nucleotides Increases the Rate of Template Dissociation from Polymerase Over Time.

2× concentration of Pol6-44X1 (SEQ ID NO:4) was pre-incubated with ShortCy5Template (SEQ ID NOS 12 and 21). Binding was allowed to proceed in the presence of 5 mM $MgCl_2$, followed by addition of 20 μM polyphosphate nucleotides nucleotides (FIG. 6A(i)) to initiate the reaction; or binding occurred in the presence of 50 uM polyphosphate nucleotides polyphosphates, followed by addition of $Mg^{2+}$ (FIG. 6A(ii)) to initiate the reaction (note the final concentration of polyphosphates is 20 uM in both cases). At time=0 minutes, salt was added to a final concentration of 500 mM KGlu. Dissociation of template from the template-DNA complex was determined following addition of polyphosphates (6A(i)) or MgCl2 (6A(ii)) at various time intervals.

Figures 6A, 6B:
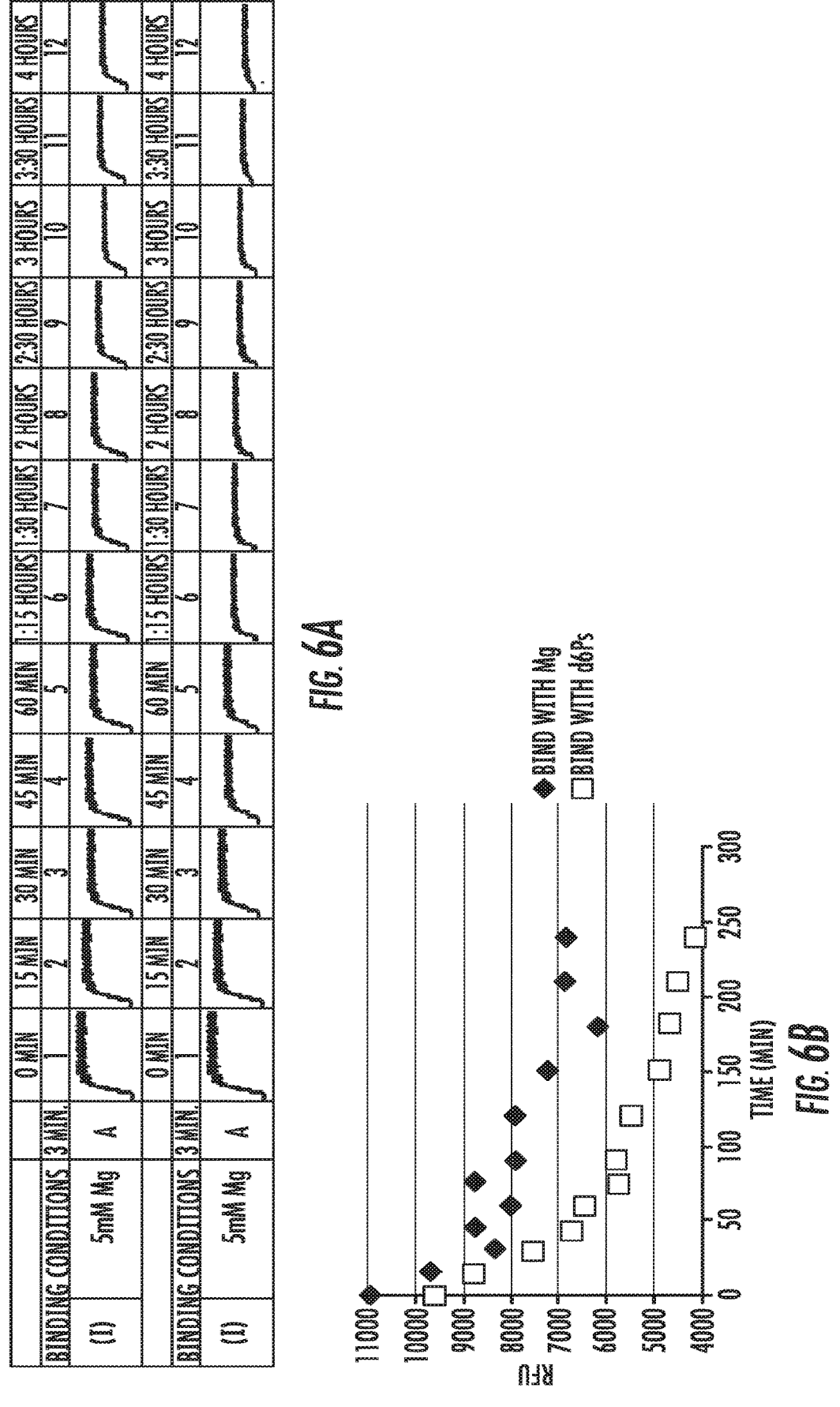
FIGS. 6A-6B is a series of graphs showing exemplary results of the effect of nucleotides on the formation of polymerase-template complex and rate of dissociation of template from polymerase-template complex formed in the presence Mg2+ (♦) or 20 uM d6Ps (polyphosphate nucleotides; □). Fluorescence signal obtained in a FRET assay are shown in (A), and dissociation curves are shown in (B). Reference is made to Example 4.2.

The data are shown in FIG. 6A (i) and (ii), and FIG. 6B. More particularly, FIG. 6A shows the fluorescence signal corresponding to the level of polymerase-template complex detected under conditions given in 6A(i) and 6A(ii). FIG. 6B shows a plot of the dissociation of polymerase from the polymerase-template complex when the complex was allowed to form in the presence of $Mg^{2+}$ alone (♦), or in the presence of polyphosphate nucleotides (□). The calculated amplitude of the fluorescence signal shown in 6A (i) and (ii) is plotted as a function of time.

These data show that forming the polymerase-template complex in the presence of 50 uM polyphosphates results in a greater rate of polymerase dissociation from template than when polymerase-template complex is formed in the presence of Mg2+ and the absence of polyphosphates.

4.3. Ca2+ does not Improve the Nucleotide-Dependent Destabilization i.e. Dissociation, of Polymerase-Template Complex.

2× concentration of Pol6-44X1 (SEQ ID NO:4) was pre-incubated with ShortCy5Template (SEQ ID NOS 12 and 21). Binding was allowed to proceed in the presence of 50 µM polyphosphates, followed by addition of 5 mM MgCl2 (FIG. 7A(i)) to initiate the reaction; or binding occurred in the presence of 50 µM polyphosphates+0.5 mM Ca2+, followed by addition of 5 mM Mg2+ (FIG. 7A(ii)) to initiate the reaction. At time=0 minutes, salt was added to a final concentration of 500 mM KGlu. Dissociation of template from the template-DNA complex was determined following addition of MgCl2 (7A) at various time intervals.

Figures 7A, 7B:
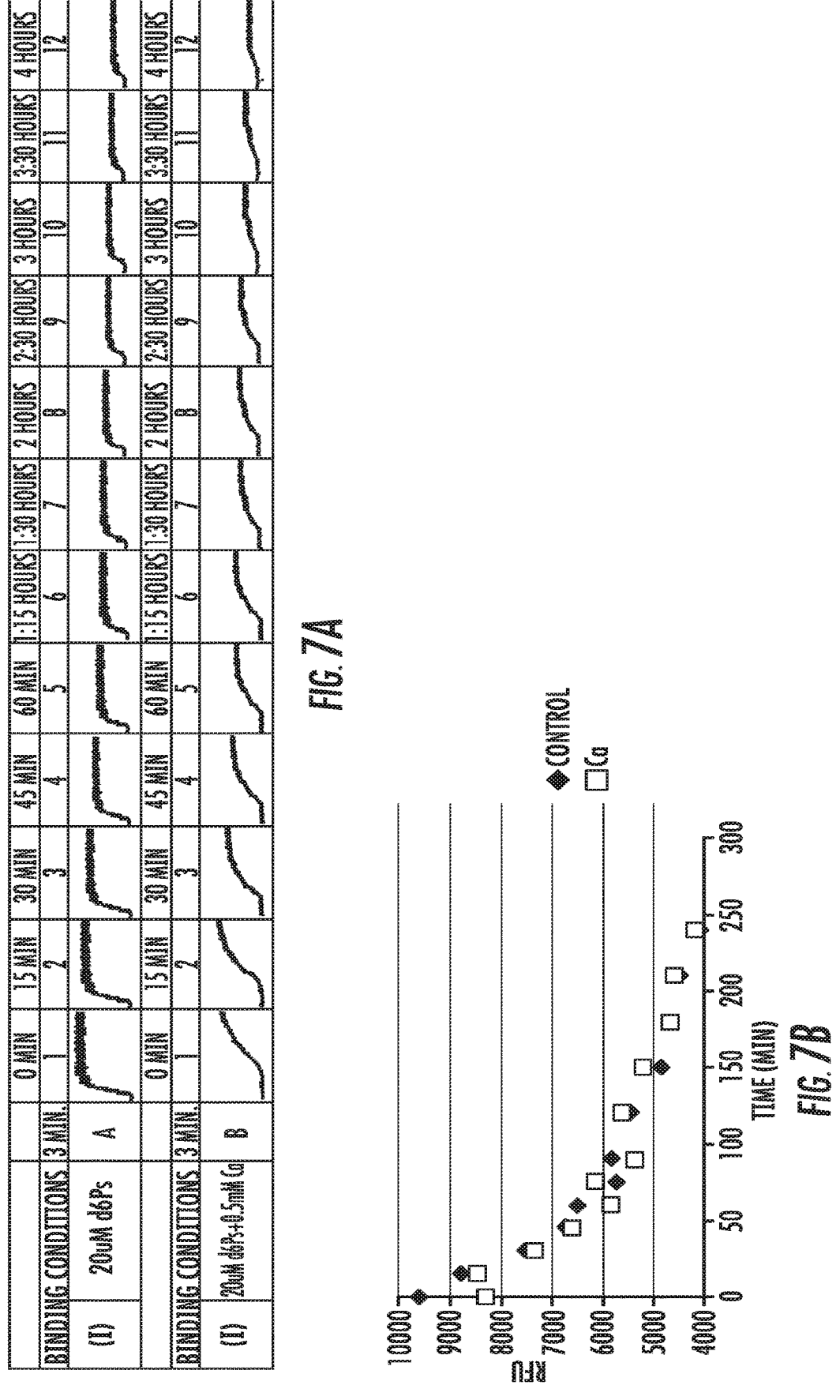
FIGS. 7A-7B is a series of graphs showing exemplary results of the effect of nucleotides (d6Ps) on the formation of polymerase-template complex and rate of dissociation of template from polymerase-template complex formed in the absence (♦) or presence (□) of Ca2+. Fluorescence signal obtained in a FRET assay are shown in (A), and dissociation curves are shown in (B). Reference is made to Example 4.3.

The data are shown in FIG. 7A (i) and (ii), and FIG. 7B. More particularly, FIG. 7A shows the fluorescence signal corresponding to the level of polymerase-template complex detected under conditions given in 7A(i) and 7A(ii). FIG. 7B shows a plot of the dissociation of polymerase from the polymerase-template complex when the complex was allowed to form in the presence of polyphosphates (♦) or in the presence of polyphosphates+$Ca^{2+}$ (□). The calculated amplitude of the fluorescence signal shown in 7A (i) and (ii) is plotted as a function of time.

As shown in FIG. 7B, the effect of $Ca^{2+}$ does not affect complex dissociation. FIG. 7B also shows that the rapid rate of complex dissociation following template binding in the presence of nucleotides is similar whether occurring in the absence or presence of $Ca^2+$.

4.4. Mg2+ does not Improve the Nucleotide-Dependent Destabilization i.e. Dissociation, of Polymerase-Template Complex During Polynucleotide Synthesis.

2× Pol6-44X1 polymerase (SEQ ID NO:4) was pre-incubated with ShortCy5Template (SEQ ID NOS 12 and 21). Binding was allowed to proceed in the absence of Mg2+ and polyphosphates, followed by addition of Mg2+ and polyphosphates to initiate the reaction (FIG. 8A(i)); in the presence of Mg2+ followed by addition of polyphosphates to initiate the reaction (FIG. 8A(ii)); or in the presence of polyphosphates, followed by addition of Mg2+ (FIG. 8A(iii)). At time=0 minutes, salt was added to a final concentration of 500 mM KGlu. Dissociation of template from the template-polymerase complex was determined following the addition of Mg2+ and polyphosphates, only polyphosphates, or only Mg2+ at different time intervals.

Figures 8A, 8B:
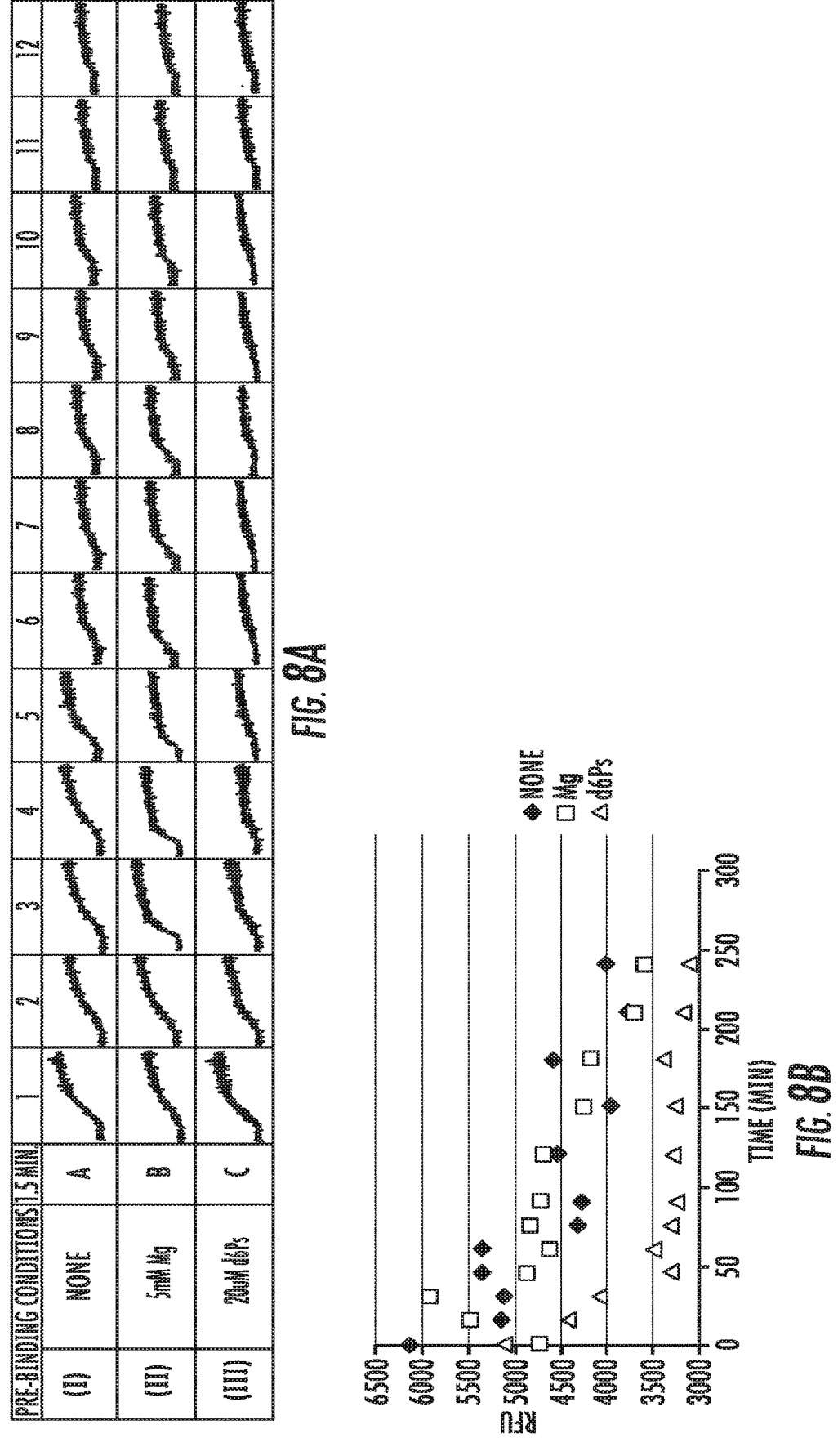
FIGS. 8A-8B is a series of graphs showing exemplary results of the rate of dissociation of template from polymerase-template complex when complex was formed in the presence of Mg2+ (□), 20 uM polyphosphate nucleotides (Δ), or in the absence of both Mg2+ and 20 uM polyphosphate nucleotides (♦). Fluorescence signal obtained in a FRET assay are shown in (A), and dissociation curves are shown in (B). Reference is made to Example 4.4.

The data are shown in FIG. 8A(i), 8A(ii), 8A(iii), and FIG. 8B. More particularly, FIG. 8A (i)-(iii) shows the fluorescence signal corresponding to the level of polymerase-template complex detected under conditions given in 8.4 A(i), 8.4 A(ii) and 8.4 A(iii), respectively. FIG. 8B shows a plot of the dissociation of polymerase from the polymerase-template complex. The calculated amplitude of the fluorescence signal shown in 8A (i), (ii), and (iii) is plotted as a function of time. The data in FIG. 8A(i) and (ii) show that polymerase-template complex formation is similar whether it occurred in the presence of Mg2+ (ii), or in the absence of both Mg2+ and nucleotides. The data shown in FIG. 8A(iii) show that nucleotides inhibit template binding. FIG. 8B shows that the rate of dissociation of complex when formed in the presence of Mg2+ (□), or in the absence of Mg2+ and nucleotides (♦) is similar. FIG. 8B (Δ) also shows that formation of complex in the presence of polyphosphates increases the rate of complex dissociation, .i.e. nucleotides destabilize polymerase-template complexes over time.

4.5. Nucleotide Triphosphates Increase the Rate of Template-Polymerase Dissociation when Compared to Polyphosphates.

2× concentration Pol6-44X1 polymerase (SEQ ID NO:4) was pre-incubated with DNA template, i.e., ShortCy5Template (SEQ ID NOS 12 and 21). Binding was allowed to proceed in the presence of polyphosphates, followed by addition of $Mg^{2+}$ to initiate the reaction (FIG. 9A(i)); or in the presence of triphosphate nucleotides followed by addition of $Mg^{2+}$ to initiate polynucleotide synthesis (condition 9A(ii)). At time=0 minutes, salt was added to a final concentration of 500 mM KGlu. Dissociation of template from the template-DNA complex was determined following addition of Mg2+ (9A) at various time intervals.

Figures 9A, 9B:
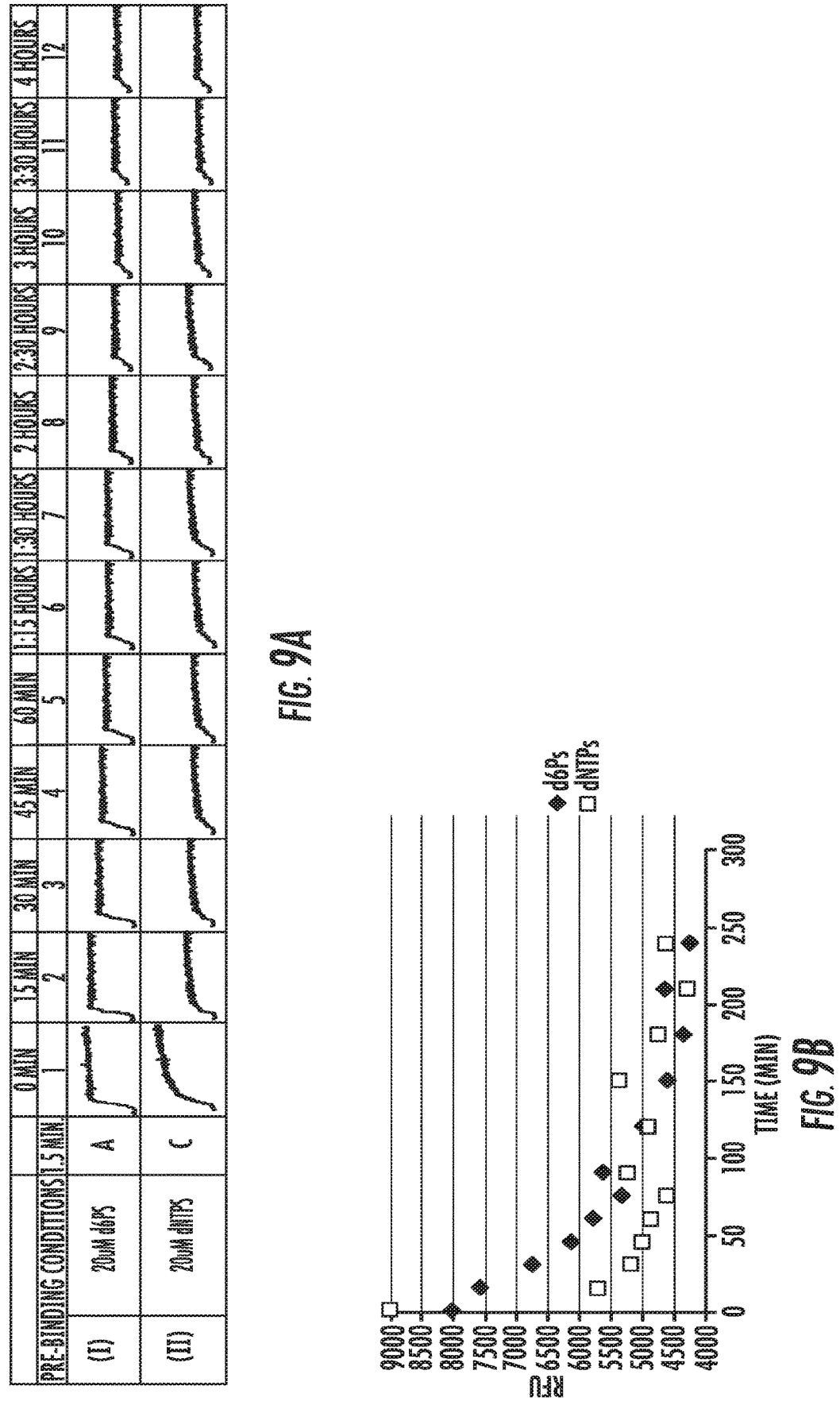
FIGS. 9A-9B is a series of graphs showing exemplary results of the rate of dissociation of template from polymerase-template complex when complex was formed in the presence of dNTPs (□), or d6Ps (♦). Fluorescence signal obtained in a FRET assay are shown in FIG. 9A, and dissociation curves are shown in FIG. 9B. Reference is made to Example 4.5.

The data are shown in FIG. 9A(i) and 9A(ii), and FIG. 9B. More particularly, FIG. 9A (i)-(ii) shows the fluorescence signal corresponding to the level of polymerase-template complex detected under conditions given in 5.5 A(i) and 5.5 A(ii), respectively. FIG. 9B shows a plot of the dissociation of polymerase from the polymerase-template complex. The calculated amplitude of the fluorescence signal shown in 9A (i) and (ii) is plotted as a function of time.

The data in FIG. 9A(i) and (ii) show that polymerase-template complex formation is similar whether it occurred in the presence of dNTP or polyphosphate nucleotides. FIG. 9B shows that the rate of dissociation of complex when formed in the presence of dNTP nucleotides (□) is greater than when in the presence of polyphosphate nucleotides nucleotides (♦).

In sum, the data show that formation of template-polymerase complex in the presence of triphosphate nucleotides results in a higher rate of template dissociation when compared to polyphosphates. This effect is expected to result in lower processivity and diminished sequencing longevity during template-dependent DNA polymerization.

Example 5: Effect of Temperature and Nucleotides on Binding of Polymerase to Template This example demonstrates the effect of temperature on the association of template from the template-polymerase complex, with and without low concentration of nucleotides.

Varying dilutions (0×, 1×, 4×, 8×) of Pol6-67 X2 (SEQ ID NO: 14) were pre-incubated with 100 nM Fluorescent Hairpin DNA template (SEQ ID NOS 15 and 22) either in the presence of 1.2 uM polyphosphate nucleotides nucleotides at 40° C. or in the absence of 1.2 uM polyphosphate nucleotides at room temperature for 30 minutes. 12 µL of pre-bound template-Pol complex was loaded onto 5% Native-TBE gel and run at 100V for 60 minutes at 4° C. Imaging was performed using Biorad's ChemiDoc XRS+ imaging system using SYBR-Green filter.

Figure 10A:
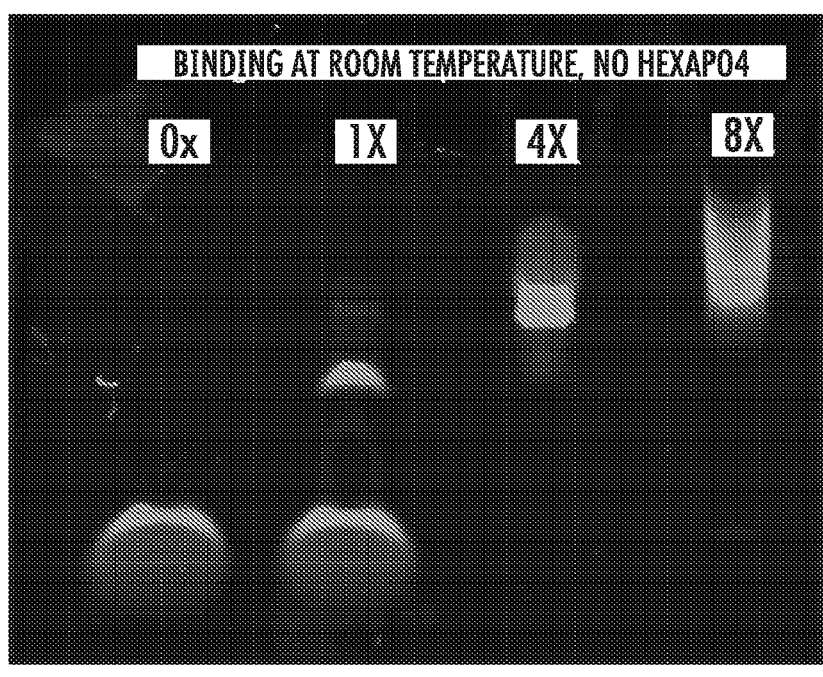
FIG. 10A is an image of a Native 5% TBE gel showing static binding of polymerase to template at room temperature. The polymerase concentration is increased (0, 1×, 4×, and 8×) relative to template concentration, in the absence of nucleotides. At 4× and 8× polymerase concentrations, the band shifts indicate non-specific binding of multiple polymerases to multiple locations on the template. Reference is made to Example 5.
Figure 10B:
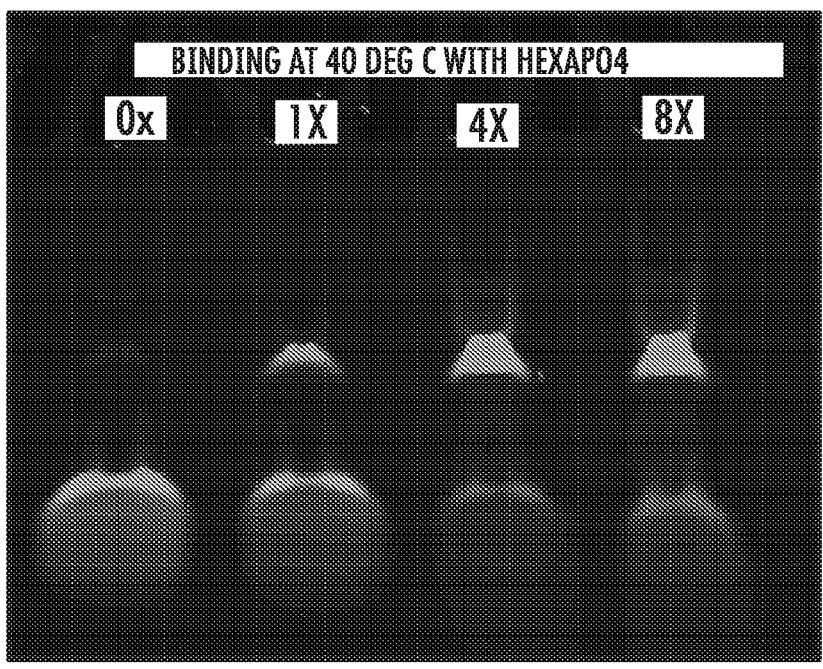
FIG. 10B is an image of a Native 5% TBE gel showing static binding of polymerase to template at 40° C. Like FIG. 10A, the polymerase concentration is increased (0, 1×, 4×, and 8×) relative to template concentration, but in the presence of 1.2 μM nucleotides (polyphosphate). The lack of band shifts at 4× and 8× concentrations indicates specific binding of the polymerase to the 3' end of the template DNA at 40° C. Reference is made to Example 5.

As shown in FIG. 10A, at 20° C., the 4× and 8× polymerase concentrations result in band shifts, thus indicating non-specific binding of multiple polymerases to multiple locations on the template. In contrast, increasing the temperature to 40° C. and adding 1.2 μM polyphosphate nucleotides did not result in the band shift (see FIG. 10B), thus indicating specific binding of the polymerase to the 3' end of the template. Hence, the addition of 1.2 μM polyphosphate and elevated temperate have a positive effect on polymerase-template binding.

Example 6: Effect of Temperature and Nucleotides on Template Extension (Extension Gel Assay)

This example demonstrates the correlation between the percent of polymerase bound to the template (at high temperature and low nucleotide levels) and extension of the template (at high temperature and high concentration of nucleotides).

Varying dilutions of Pol6-67 X2 (0×, 1×, 2×, 4×, 8×) were pre-incubated with 300 mM Fluorescent Hairpin DNA template (SEQ ID NOS 15 and 22) in the presence of 1.2 uM polyphosphate nucleotides nucleotides at 40° C. for 30 minutes. The binding buffer was a Hepes buffer having 75 mM K-Glu, 20 mM Hepes (pH 7.5), 5 mM TCEP, and 8% Trehalose.

For the binding gel, 12 μL of pre-bound template-Pol complex was loaded onto 5% Native-TBE gel and run at 100V for 60 minutes at 4° C. Imaging was performed using Biorad's ChemiDoc XRS+ imaging system using SYBR-Green filter.

For the extension reaction, 10 uM of polyphosphate nucleotides, 5 mM MgCl2 (Final each) and 20× Chase template (SEQ ID NO: 16) was added to the pre-bound Polymerase-template complex to initiate the reaction. The reactions were ran for 5 mins at 30° C. After 5 minutes, the reactions were quenched using Formamide+50 mM EDTA, and heated at 95° C. for 5 minutes. 12 μL of the samples were then loaded on to 15% TB-Urea Gel at 180V for 180 minutes and imaged using Biorad's ChemiDoc XRS+ imaging system using SYBR-Green filter.

Figure 11A:
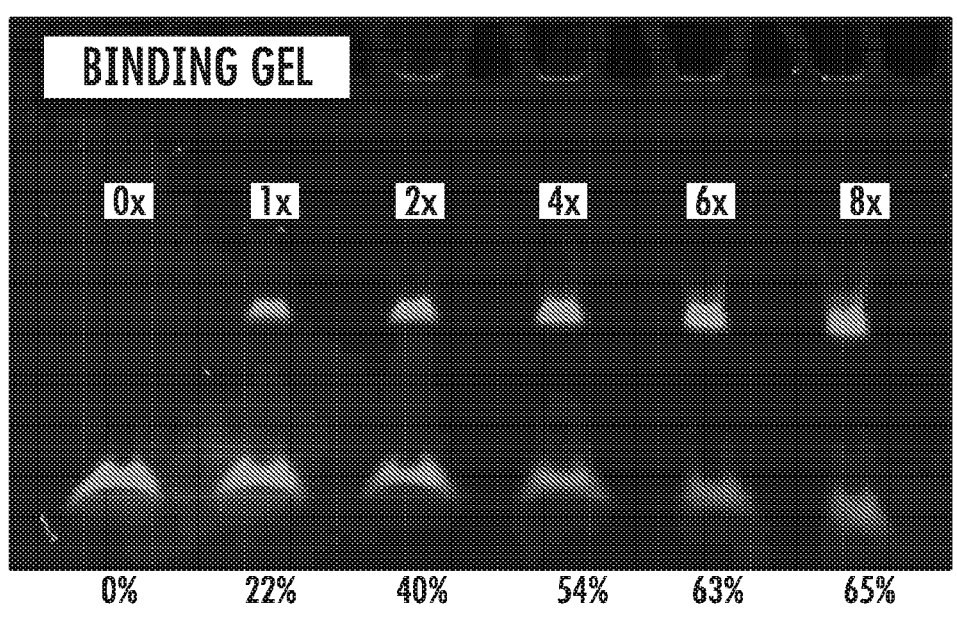
FIGS. 11A-11C illustrate the correlation between polymerase-template binding and extension of the template at 40° C. More particularly.
Figure 11B:
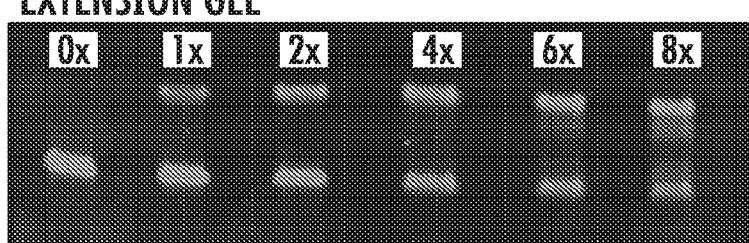
Figure 11C:
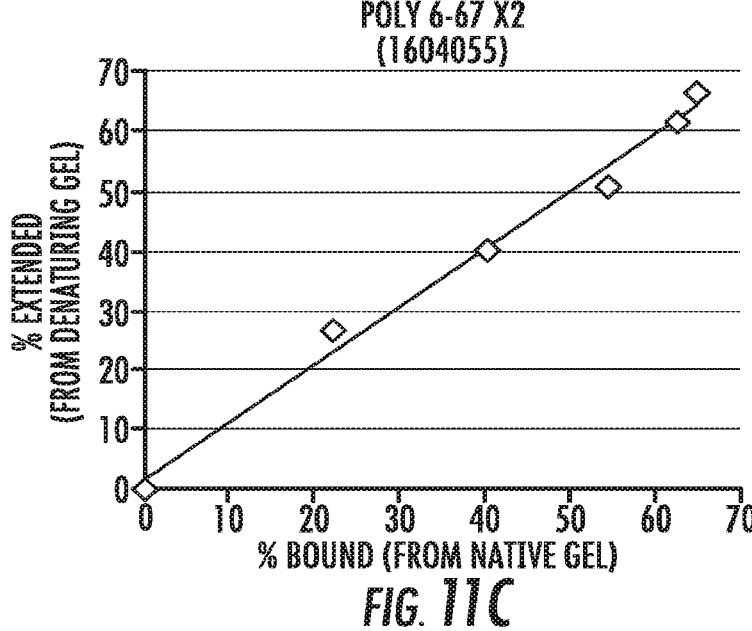

As shown in FIG. 11A, increasing polymerase concentration results in an increase in template binding at 40° C. in the presence of low (1.2 μM) polyphosphate nucleotides. As evidenced by the shifts in band intensity from the lower band to the upper band with increased concentration of polymerase in FIG. 11B, increasing the concentration of polymerase results in increased template extension, with the concentration of nucleotides adjusted to 10 μM during the extension reaction. At 1× polymerase, the active fraction shows 26% extension, whereas at 8× polymerase the active fraction shows 66% extension at 40° C. (FIG. 11B). When percent binding is compared with percent extension, a direct correlation exists (see FIG. 11C; slope=1). Hence, the active fraction is largely dependent on polymerase binding to the template before extension.

Example 7: Effect of Temperature and Nucleotides on Template Extension (Fret Assay)

This example demonstrates formation and extension of the polymerase-template complex and template extension at 40° C. using a FRET assay (as described in Example 3).

Equi-molar quantities of LongHP-Cy5-ExoR template (SEQ ID NOS 17 and 22) were annealed with Quencher Primer (SEQ ID NO: 18) using the cool-down annealing protocol. A control was made in which only LongHP-Cy5-

ExoR template (SEQ ID NOS 17 and 22) (at the same final concentration) was diluted in 1×TE and was also passed through the cool-down annealing protocol.

Varying dilutions of Pol6-67 X2 (0×, 1×, 2×, 4×, 6×, 8×) were pre-incubated with either 50 mM annealed Template-Primer pair or with just the Template control in the presence of 1.2 uM polyphosphate nucleotides nucleotides at 40° C. for 30 minutes. The binding buffer was a Hepes buffer having 75 mM K-Glu, 20 mM Hepes (pH 7.5), 5 mM TCEP, and 8% Trehalose.

The above reactions were carried out in a 96 well half area black plates. The plate reader (BMG FLUOstar Omega) injected Reagent B, that contained 75 mM K-Glu, 20 mM Hepes, 5 mM TCEP, 5 mM MgCl2, 10 uM Nucs, 20× Chase (final concentrations), which initiated the reaction and the fluorescence was measured every 1 s for 10 minutes. The excitation filter used is 590-50 nm and the emission filter used is 675-50.

Figure 12A:
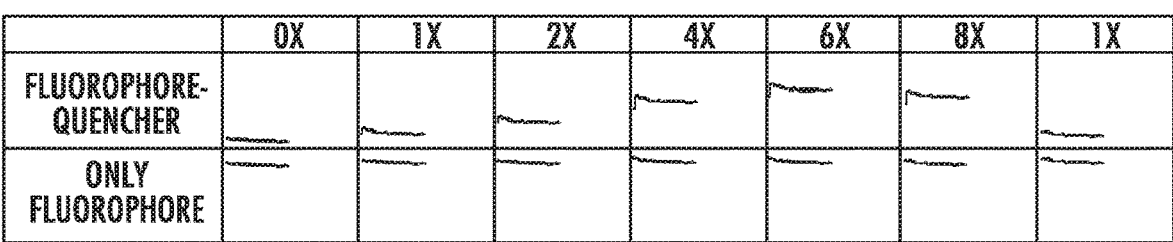
FIGS. 12A-12D are a series of graphs illustrating template extension following the formation of the polymerase-template complex at 40° C. and in the presence of low levels of nucleotides (1.2 μM).
Figure 12B:
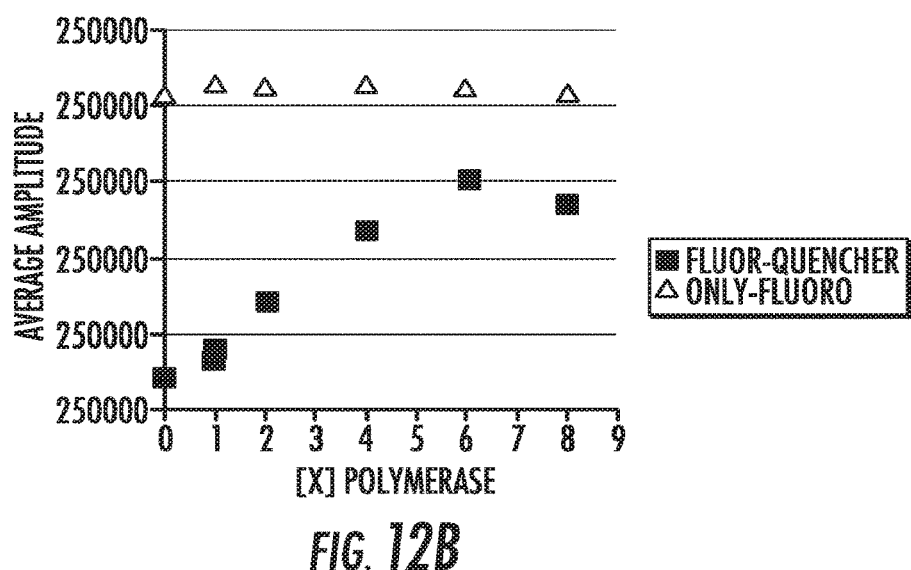
Figure 12C:
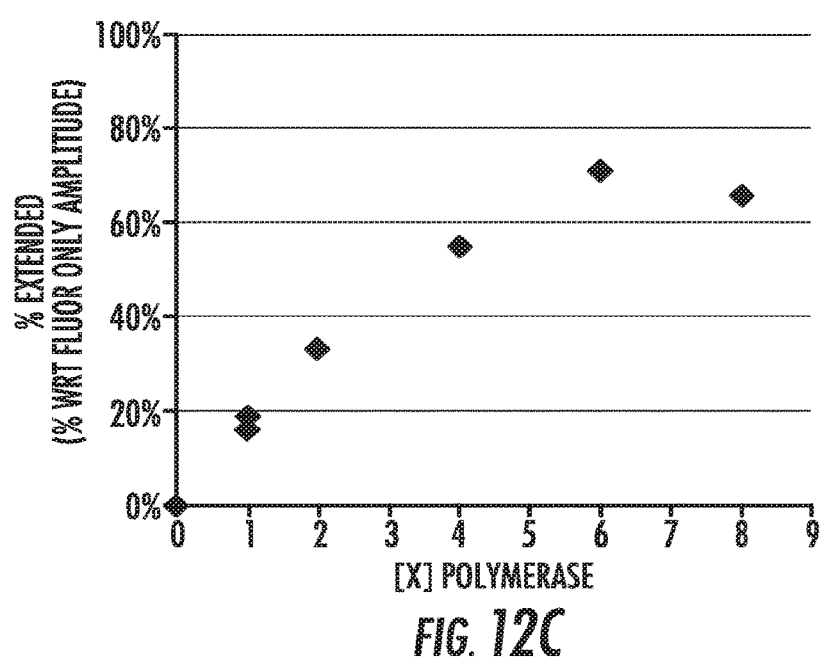

FIGS. 12A-12C show template extension following polymerase-template formation at 40° C. and in the presence of low levels of nucleotides (1.2 μM). As shown in FIG. 12A and FIG. 12B, following polymerase-template formation, increasing polymerase concentration results in increased extension, as evidenced the by increased signal amplitude of the fluorophore quencher at increased polymerase concentrations. At 0× polymerase, for example, no binding of the template to the polymerase can occur and the fluorescent signal is thus completely quenched. Increasing the polymerase concentration during polymerase-template formation, however, results in less of the signal being quenched (which corresponds to an increase in fluoresce amplitude) (FIGS. 12A and 12B). The control fluorophore alone remains maximally fluorescent (i.e., 100% saturation) across the various polymerase concentrations (FIGS. 12A and 12B). As shown in FIG. 12C, the percent extension—as determined as a percentage of the 100% saturation of the fluorophore alone—also illustrates that increased polymerase concentration during polymerase-template formation results in increased extension during the extension reaction when the complex is formed at high temperature and in the presence of low levels of nucleotides.

Figure 12D:
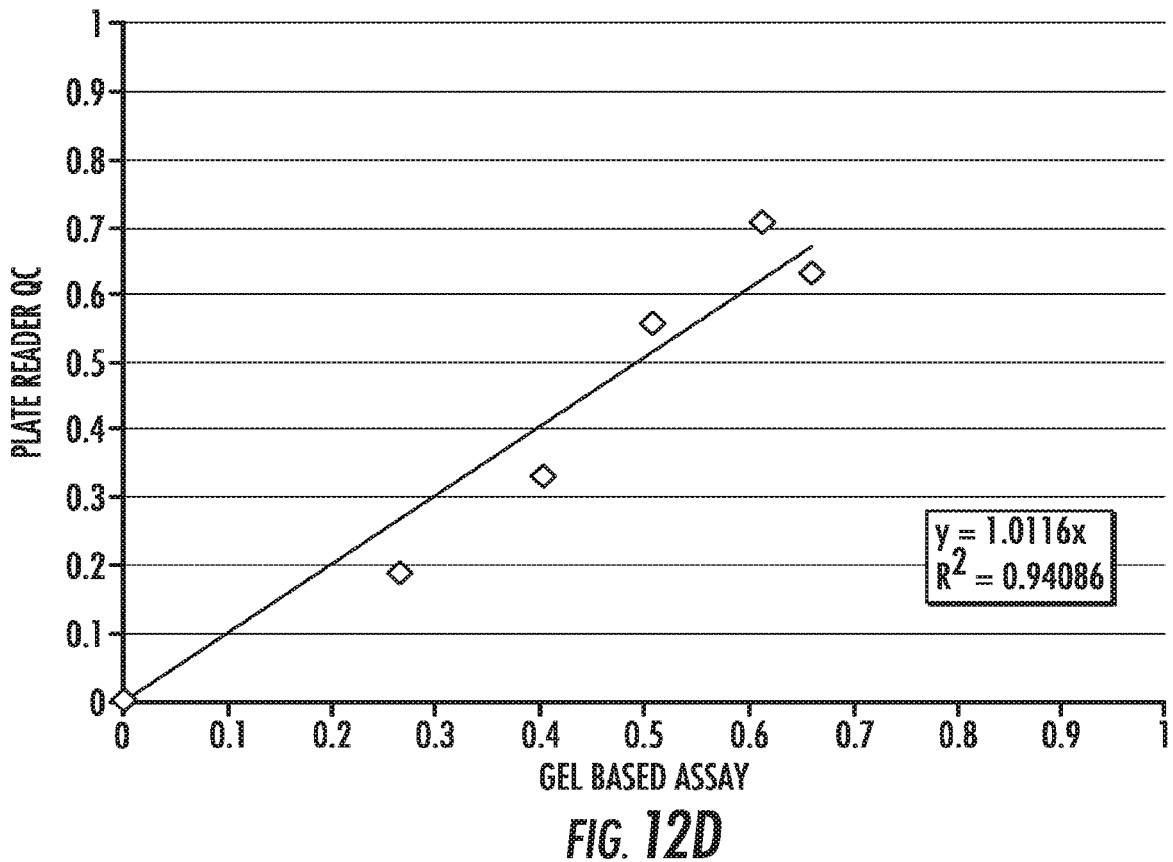

In FIG. 12D, the amount of template extension obtained from two independent experiments, one being gel based assay and the other being plate reader assay (FRET assay), is compared. The figure shows that the slope of the line is close to 1, thus evidencing that there is good correlation between % template extension as measured by gel-based and plate-reader based assays.

Example 8: Effect of Binding Conditions on Polymerase-Template Dissociation

This example demonstrates the effect of $Sr^{+2}$ and/or nucleotides on dissociation of the polymerase-template complex using a FRET assay (as described in Example 3).

6× concentration of Pol6-67X2 (SEQ ID NO:14) was pre-incubated with Long-HP-Cy5-ExoR template (SEQ ID NOS 17 and 22). Binding was allowed to proceed for 30 minutes at 40 C in the presence of either (13A(i)) 1.2 uM dNpCpp, 3 mM SrCl2 or (13A(ii)) 1.2 uM dNpCpp or (13A(iii)) 1.2 uM polyphosphates or (13A(iv)) absence of SrCl2, nucleotides. At time=0 minutes, salt was added to a final concentration of 300 mM KGlu, and chase to a final concentration of 20×. Dissociation of template from the template-DNA complex was determined following addition of polyphosphates and MgCl2 at various time intervals.

Figures 13A, 13B:
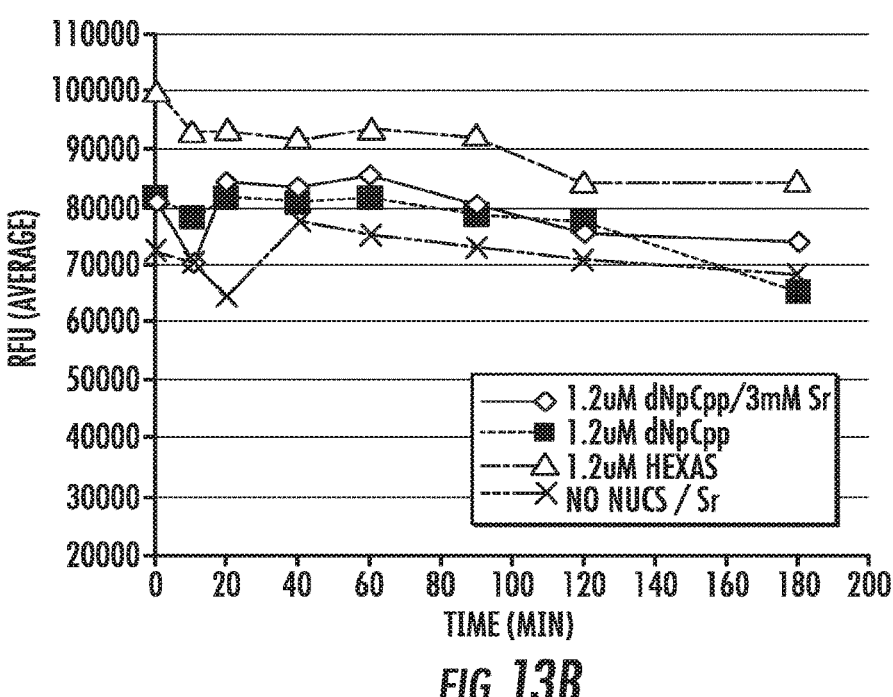
FIGS. 13A-13B are a series of graphs illustrating polymerase template binding and dissociation at varying binding conditions at 40° C.

As shown in FIGS. 13A and 13B, Sr$^{+2}$ has minimal effect on the dissociation of the polymerase from the template. Further, the low concentration of polyphosphate nucleotides is the best binding condition. Other data (not shown) illustrate that Sr$^{+2}$ does not have any significant effect on polymerase-template binding.

Example 9: Effect of Nucleotides and Salt Spike

This example demonstrates the effect of high nucleotide concentration on polymerase-template binding in the presence of elevated salt concentration.

6× concentration of Pol6-67X2 (SEQ ID NO:14) was pre-incubated with Long-HP-Cy5-ExoR template (SEQ ID NOS 17 and 22). Binding was allowed to proceed for 30 minutes at 40 C in the presence or absence of 36 uM polyphosphates. At time=0 minutes, salt was added to a final concentration of either 75 mM (FIG. 14A) or 380 mM KGlu (FIG. 14B) along with 2 mM Biotin, 20× Chase Template, and 1 mM SrCl2. Dissociation of template from the template-DNA complex was determined following addition of only Mg2+ or 36 uM polyphosphates and Mg2+ respectively at various time intervals.

Figure 14A:
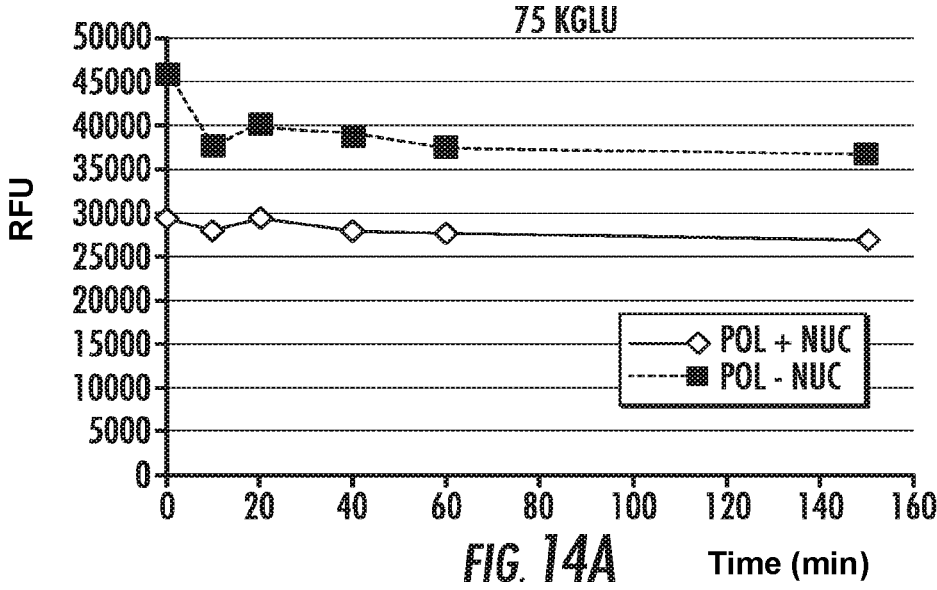
FIGS. 14A-14B are graphs illustrating the effects of salt concentration on polymerase-complex formation at 40° C. and dissociation at 30° C. in the presence and absence of high nucleotide concentration (36 uM).
Figure 14B:
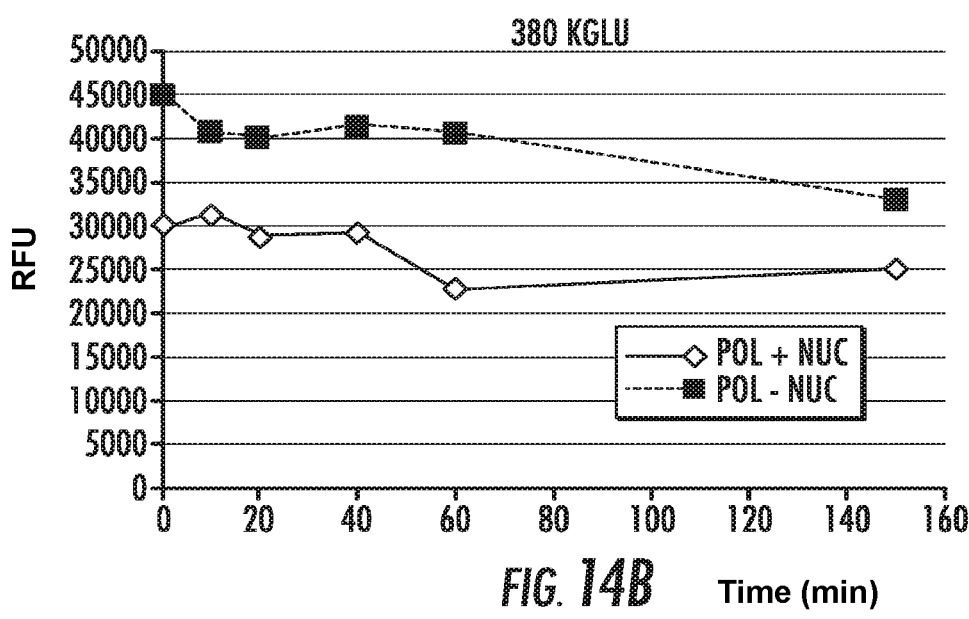

As shown in FIG. 14A and FIG. 14B, both salt concentrations of 75KGlu and 380KGlu, in the presence of high levels of nucleotides (36 μM during binding) resulted in 33% reduction in initial template binding. For Pol6-67X2 there does not seem to be a significant difference in template-polymerase dissociation rate in presence or absence of polyphosphates.

Example 10: Attachment of Polymerase to Nanopore

This example provides methods of attaching a variant polymerase to a nanopore, e.g., α-hemolysin, OmpG.

The Pol6 variant with SpyCatcher HisTag (SEQ ID NO:4) was expressed according to Example 2 and purified using a cobalt affinity column. The polymerase-template complex was formed, purified, and attached to a nanopore to form nanopore sequencing complex. Methods for forming nanopore sequencing complexes and for purifying nanopore sequencing complexes are described in U.S. Provisional Application "Nanopore Sequencing Complexes" 62/281, 719 filed on Jan. 21, 2016, and U.S. Provisional application "Purification of Polymerase Complexes" 62/260,194 filed on Nov. 25, 2015, which are herein incorporated by reference in their entirety. Nanopore sequencing complexes can be formed by sequential binding of variant polymerase to nanopore to form an enzyme-nanopore complex, followed by association of template to form the nanopore sequencing complex. Alternatively, nanopore sequencing complexes can be formed by first associating the template with the variant polymerase to form a template-enzyme complex, and subsequently attaching the template-enzyme complex to the nanopore.

A polymerase can be coupled to the nanopore by any suitable means. See, for example, PCT/US2013/068967 (published as WO2014/074727; Genia Technologies, Inc.), PCT/US2005/009702 (published as WO2006/028508; President and Fellows of Harvard College), and PCT/US2011/065640 (published as WO2012/083249; Columbia University).

A variant pol6 DNA polymerase, is coupled to a protein nanopore (e.g. alpha-hemolysin, OmpG), through a linker molecule. Specifically, the SpyTag and SpyCatcher system that spontaneously forms covalent isopeptide linkages under physiological conditions is used. See, for example, Li et al, J Mol Biol. 2014 Jan. 23; 426(2):309-17.

Example 11: Nanopore Sequencing

The ability of a nanopore-bound variant Pol6 polymerase to bind tagged nucleotides and thereby allow for the detection of blocked channel currents at the nanopore to which the polymerase is attached, was determined. Increased processivity of the variant Pol6 polymerases was compared to that of the parent Pol6 lacking the modifications of the variant enzyme.

The variant Pol6 polymerase is contacted with DNA template to form variant Pol6-DNA complex, which is subsequently attached to a nanopore embedded in a lipid bilayer over a well on a semiconductor sensor chip, also called a biochip. The lipid bilayer is formed and the nanopore with attached variant Pol6 polymerase-DNA complex i.e. the variant Pol6 nanopore sequencing complex, is inserted as described in PCT/US2014/061853 (entitled "Methods for Forming Lipid Bilayers on Biochips" and filed 22 Oct. 2014).

Alternatively, the nanopore is embedded into the lipid bilayer, and the variant Pol6-DNA complex is attached in situ.

A mixture of tagged nucleotides, where the tag is a polymer of 30 thymine nucleotides (T30) consisting of 3 uM T-T30, 3 uM C-T30, 3 uM G-T30, and 3 uM A-T30, in static conditions (500 mM KGlu, 3 mM CaCl$_2$, 20 mM HEPES, pH8.0), is flowed over the nanopores at a rate of 0.834 ul/second.

An alternating current of 210 mV peak to peak is applied at 25 Hz, and capture of nucleotide tags is assessed as nucleotide bases are incorporated into the copied DNA strand by the nanopore-bound polymerase.

Processivity of the variant Pol6 is compared to that of the unmodified parental Pol6 to determine an increase in read-length, and/or speed of polynucleotide synthesis, and/or a decrease in sequencing error.

SEQUENCE LISTING FREE TEXT

```
SEQ ID NO: 1 - Wild-type Pol6 (DNA polymerase [Clostridium phage
phiCPV4]; GenBank: AFH27113.1)

001 mdkhtqyvke hsfnydeykk anfdkiecli fdtesctnye ndntgarvyg wglgvtrnhn 061 miygqnlnqf wevcqnifnd wyhdnkhtik itktkkgfpk rkyikfpiav hnlgwdvefl 121 kyslvengfn ydkgllktvf skgapyqtvt dveepktfhi vqnnnivygc nvymdkffev 181 enkdgsttei glcldffdsy kiitcaesqf hnyvhdvdpm fykmgeeydy dtwrspthkq 241 ttlelryqyn diymlrevie qfyidglcgg elpltgmrta ssiafnvlkk mtfgeektee
```

-continued

```
301 gyinyfeldk ktkfeflrkr iemesytggy thanhkavgk tinkigcsld inssypsqma 361 ykvfpygkpv rktwgrkpkt eknevyliev gfdfvepkhe eyaldifkig avnskalspi 421 tgavsgqeyf ctnikdgkai pvykelkdtk lttnynvvlt sveyefwikh fnfgvfkkde 481 ydcfevdnle ftglkigsil yykaekgkfk pyvdhftkmk venkklgnkp ltnqakliln 541 gaygkfgtkq nkeekdlimd knglltftgs vteyegkefy rpyasfvtay grlqlwnaii 601 yavgvenfly cdtdsiycnr evnsliedmn aigetidkti lgkwdvehvf dkfkvlgqkk 661 ymyhdckedk tdlkccglps darkiiigqg fdefylgknv egkkqrkkvi ggcllldtlf 721 tikkimf*
```

SEQ ID NO: 2 - Pol6 (with His tag)
```
MHHHHHHHHS GGSDKHTQYV KEHSFNYDEY KKANFDKIEC LIFDTESCTN           50

YENDNTGARV YGWGLGVTRN HNMIYGQNLN QFWEVCQNIF NDWYHDNKHT          100

IKITKTKKGF PKRKYIKFPI AVHNLGWDVE FLKYSLVENG FNYDKGLLKT          150

VFSKGAPYQT VTDVEEPKTF HIVQNNNIVY GCNVYMDKFF EVENKDGSTT          200

EIGLCLDFFD SYKIITCAES QFHNYVHDVD PMFYKMGEEY DYDTWRSPTH          250

KQTTLELRYQ YNDIYMLREV IEQFYIDGLC GGELPLTGMR TASSIAFNVL          300

KKMTFGEEKT EEGYINYFEL DKKTKFEFLR KRIEMESYTG GYTHANHKAV          350

GKTINKIGCS LDINSSYPSQ MAYKVFPYGK PVRKTWGRKP KTEKNEVYLI          400

EVGFDFVEPK HEEYALDIFK IGAVNSKALS PITGAVSGQE YFCTNIKDGK          450

AIPVYKELKD TKLTTNYNVV LTSVEYEFWI KHFNFGVFKK DEYDCFEVDN          500

LEFTGLKIGS ILYYKAEKGK FKPYVDHFTK MKVENKKLGN KPLTNQAKLI          550

LNGAYGKFGT KQNKEEKDLI MDKNGLLTFT GSVTEYEGKE FYRPYASFVT          600

AYGRLQLWNA IIYAVGVENF LYCDTDSIYC NREVNSLIED MNAIGETIDK          650

TILGKWDVEH VFDKFKVLGQ KKYMYHDCKE DKTDLKCCGL PSDARKIIIG          700

QGFDEFYLGK NVEGKKQRKK VIGGCLLLDT LFTIKKIMF*                     739
```

SEQ ID NO: 3 - Pol6 with His-tag (DNA sequence)
```
ATGCATCACC ATCATCATCA CCACCACAGC GGCGGTTCCG ACAAACACAC           50

GCAGTACGTC AAAGAGCATA GCTTCAATTA TGACGAGTAT AAGAAAGCGA          100

ATTTCGACAA GATCGAGTGC CTGATCTTTG ACACCGAGAG CTGCACGAAT          150

TATGAGAACG ATAATACCGG TGCACGTGTT TACGGTTGGG GTCTTGGCGT          200

CACCCGCAAC CACAATATGA TCTACGGCCA AAATCTGAAT CAGTTTTGGG          250

AAGTATGCCA GAACATTTTC AATGATTGGT ATCACGACAA CAAACATACC          300

ATTAAGATTA CCAAGACCAA GAAAGGCTTC CCGAAACGTA AGTACATTAA          350

GTTTCCGATT GCAGTTCACA ATTTGGGCTG GGATGTTGAA TTCCTGAAGT          400

ATAGCCTGGT GGAGAATGGT TTCAATTACG ACAAGGGTCT GCTGAAAACT          450

GTTTTTAGCA AGGGTGCGCC GTACCAAACC GTGACCGATG TTGAGGAACC          500

GAAAACGTTC CATATCGTCC AGAATAACAA CATCGTTTAT GGTTGTAACG          550

TGTATATGGA CAAATTCTTT GAGGTCGAGA CAAAGACGG CTCTACCACC          600

GAGATTGGCC TGTGCTTGGA TTTCTTCGAT AGCTATAAGA TCATCACGTG          650

TGCTGAGAGC CAGTTCCACA ATTACGTTCA TGATGTGGAT CCAATGTTCT          700

ACAAAATGGG TGAAGAGTAT GATTACGATA CTTGGCGTAG CCCGACGCAC          750

AAGCAGACCA CCCTGGAGCT GCGCTACCAA TACAATGATA TCTATATGCT          800
```

-continued

```
GCGTGAAGTC ATCGAACAGT TTTACATTGA CGGTTTATGT GGCGGCGAGC          850

TGCCGCTGAC CGGCATGCGC ACCGCTTCCA GCATTGCGTT CAACGTGCTG          900

AAAAAGATGA CCTTTGGTGA GGAAAAGACG GAAGAGGGCT ACATCAACTA          950

TTTTGAATTG GACAAGAAAA CCAAATTCGA GTTTCTGCGT AAGCGCATTG         1000

AAATGGAATC GTACACCGGT GGCTATACGC ACGCAAATCA CAAAGCCGTT         1050

GGTAAGACTA TTAACAAGAT CGGTTGCTCT TTGGACATTA ACAGCTCATA         1100

CCCTTCGCAG ATGGCGTACA AGGTCTTTCC GTATGGCAAA CCGGTTCGTA         1150

AGACCTGGGG TCGTAAACCA AAGACCGAGA AGAACGAAGT TTATCTGATT         1200

GAAGTTGGCT TTGACTTCGT GGAGCCGAAA CACGAAGAAT ACGCGCTGGA         1250

TATCTTTAAG ATTGGTGCGG TGAACTCTAA AGCGCTGAGC CCGATCACCG         1300

GCGCTGTCAG CGGTCAAGAG TATTTCTGTA CGAACATTAA AGACGGCAAA         1350

GCAATCCCGG TTTACAAAGA ACTGAAGGAC ACCAAATTGA CCACTAACTA         1400

CAATGTCGTG CTGACCAGCG TGGAGTACGA GTTCTGGATC AAACACTTCA         1450

ATTTTGGTGT GTTTAAGAAA GACGAGTACG ACTGTTTCGA AGTTGACAAT         1500

CTGGAGTTTA CGGGTCTGAA GATTGGTTCC ATTCTGTACT ACAAGGCAGA         1550

GAAAGGCAAG TTTAAACCTT ACGTGGATCA CTTCACGAAA ATGAAAGTGG         1600

AGAACAAGAA ACTGGGTAAT AAGCCGCTGA CGAATCAGGC AAAGCTGATT         1650

CTGAACGGTG CGTACGGCAA ATTCGGCACC AAACAAAACA AAGAAGAGAA         1700

AGATTTGATC ATGGATAAGA ACGGTTTGCT GACCTTCACG GGTAGCGTCA         1750

CGGAATACGA GGGTAAAGAA TTCTATCGTC CGTATGCGAG CTTCGTTACT         1800

GCCTATGGTC GCCTGCAACT GTGGAACGCG ATTATCTACG CGGTTGGTGT         1850

GGAGAATTTT CTGTACTGCG ACACCGACAG CATCTATTGT AACCGTGAAG         1900

TTAACAGCCT CATTGAGGAT ATGAACGCCA TTGGTGAAAC CATCGATAAA         1950

ACGATTCTGG GTAAATGGGA CGTGGAGCAT GTCTTTGATA AGTTTAAGGT         2000

CCTGGGCCAG AAGAAGTACA TGTATCATGA TTGCAAAGAA GATAAAACGG         2050

ACCTGAAGTG TTGCGGTCTG CCGAGCGATG CCCGTAAGAT TATCATTGGT         2100

CAAGGTTTCG ACGAGTTTTA TCTGGGCAAA AATGTCGAAG GTAAGAAGCA         2150

ACGCAAAAAA GTGATCGGCG GTTGCCTGCT GCTGGACACC CTGTTTACGA         2200

TCAAGAAAAT CATGTTCTAA                                          2220
```

SEQ ID NO: 4 - Po16-44-X1 with His-tag/SpyCatcher

```
MHHHHHHHHS GDYDIPTTEN LYFQGAMVDT LSGLSSEQGQ SGDMTIEEDS          50

ATHIKFSKRD EDGKELAGAT MELRDSSGKT ISTWISDGQV KDFYLYPGKY         100

TFVETAAPDG YEVATAITFT VNEQGQVTVN GKATKGDAHI GGSDKHTQYV         150

KEHSFNYDEY KKANFDKIEC LIFATESCTN YENDNTGARV YGWGLGVTRN         200

HNMIYGQNLN QFWEVCQNIF NDWYHDNKHT IKITKTKKGF PKRKYIKFPI         250

AVHNLGWDVE FLKYSLVENG FNYDKGLLKT VFSKGAPYQT VTDVEEPKTF         300

HIVQNNNIVY GCNVYMDKFF EVENKDGSTT EIGLCLDFFD SYKIITCAES         350

QFHNYVHDVD PMFYKMGEEY DYDTWRSPTH KQTTLELRYQ YNDIYMLREV         400

IEQFYIDGLC GGELPLTGMR TASSIAFNVL KKMTFGEEKT EEGYINYFEL         450

DKKTKFEFLR KRIEMESYTG GYTHANHKAV GKTINKIGCS LDINSAYPSQ         500

MAYKVFPYGK PVRKTWGRKP KTEKNEVYLI EVGFDFVEPK HEEYALDIFK         550
```

-continued

IGAVNSKALS PITGAVSGQE YFCTNIKDGK AIPVYKELKD TKLTTNYNVV       600

LTSVEYEFWI KHFNFGVFKK DEYDCFEVDN LEFTGLKIGS ILYYKAEKGK       650

FKPYVDHFMK MKVENKKLGN KPLTNQFKLI LNGAYGKFGT KQNKEEKDLI       700

MDKNGLLTFT GSVTEYEGKE FYRPYASFVT AYGRLQLWNA IIYAVGVENF       750

LYCDTDSIYC NREVNSLIED MNAIGETIDK TILGKWDVEH VFDKFKVLGQ       800

KKYMYHDCKE DKTDLKCCGL PSDARKIIIG QGFDEFYLGK NVEGKKQRKK       850

VIGGCLLLDT LFTIKKIMF\*       869

SEQ ID NO: 5 - Po16-44-X1 with His-tag/SpyCatcher (DNA sequence)
ATG<u>CATCACC ATCATCATCA CCACCAC</u>*AGC GGTGACTACG ACATCCCGAC*       50

*CACCGAGAAC CTGTACTTCC AGGGCGCCAT GGTGGACACA CTGAGCGGTC*       100

*TGAGCAGTGA ACAGGGCCAG AGCGGCGACA TGACCATTGA AGAGGACAGC*       150

*GCCACCCACA TCAAGTTCAG CAAGCGTGAC GAGGACGGTA AGGAACTGGC*       200

*CGGCGCCACC ATGGAACTGC GTGACAGCAG CGGCAAGACC ATCAGCACCT*       250

*GGATCAGCGA TGGCCAGGTG AAGGACTTCT ACCTGTACCC GGGCAAGTAC*       300

*ACCTTCGTGG AGACAGCCGC ACCGGACGGT TACGAGGTTG CCACCGCCAT*       350

*CACCTTCACC GTGAACGAGC AGGGCCAAGT GACCGTTAAC GGCAAGGCCA*       400

*CCAAGGGTGA CGCCCACATC* GGCGGTTCCG ACAAACACAC GCAGTACGTC       450

AAAGAGCATA GCTTCAATTA TGACGAGTAT AAGAAAGCGA ATTTCGACAA       500

GATCGAGTGC CTGATCTTTG CGACCGAGAG CTGCACGAAT TATGAGAACG       550

ATAATACCGG TGCACGTGTT TACGGTTGGG GTCTTGGCGT CACCCGCAAC       600

CACAATATGA TCTACGGCCA AAATCTGAAT CAGTTTTGGG AAGTATGCCA       650

GAACATTTTC AATGATTGGT ATCACGACAA CAAACATACC ATTAAGATTA       700

CCAAGACCAA GAAAGGCTTC CCGAAACGTA AGTACATTAA GTTTCCGATT       750

GCAGTTCACA ATTTGGGCTG GGATGTTGAA TTCCTGAAGT ATAGCCTGGT       800

GGAGAATGGT TTCAATTACG ACAAGGGTCT GCTGAAAACT GTTTTTAGCA       850

AGGGTGCGCC GTACCAAACC GTGACCGATG TTGAGGAACC GAAAACGTTC       900

CATATCGTCC AGAATAACAA CATCGTTTAT GGTTGTAACG TGTATATGGA       950

CAAATTCTTT GAGGTCGAGA ACAAAGACGG CTCTACCACC GAGATTGGCC       1000

TGTGCTTGGA TTTCTTCGAT AGCTATAAGA TCATCACGTG TGCTGAGAGC       1050

CAGTTCCACA ATTACGTTCA TGATGTGGAT CCAATGTTCT ACAAAATGGG       1100

TGAAGAGTAT GATTACGATA CTTGGCGTAG CCCGACGCAC AAGCAGACCA       1150

CCCTGGAGCT GCGCTACCAA TACAATGATA TCTATATGCT GCGTGAAGTC       1200

ATCGAACAGT TTTACATTGA CGGTTTATGT GGCGGCGAGC TGCCGCTGAC       1250

CGGCATGCGC ACCGCTTCCA GCATTGCGTT CAACGTGCTG AAAAAGATGA       1300

CCTTTGGTGA GGAAAAGACG GAAGAGGGCT ACATCAACTA TTTTGAATTG       1350

GACAAGAAAA CCAAATTCGA GTTTCTGCGT AAGCGCATTG AAATGGAATC       1400

GTACACCGGT GGCTATACGC ACGCAAATCA CAAAGCCGTT GGTAAGACTA       1450

TTAACAAGAT CGGTTGCTCT TTGGACATTA ACAGCGCGTA CCCTTCGCAG       1500

ATGGCGTACA AGGTCTTTCC GTATGGCAAA CCGGTTCGTA AGACCTGGGG       1550

TCGTAAACCA AAGACCGAGA AGAACGAAGT TTATCTGATT GAAGTTGGCT       1600

TTGACTTCGT GGAGCCGAAA CACGAAGAAT ACGCGCTGGA TATCTTTAAG       1650

-continued

```
ATTGGTGCGG TGAACTCTAA AGCGCTGAGC CCGATCACCG GCGCTGTCAG          1700

CGGTCAAGAG TATTTCTGTA CGAACATTAA AGACGGCAAA GCAATCCCGG          1750

TTTACAAAGA ACTGAAGGAC ACCAAATTGA CCACTAACTA CAATGTCGTG          1800

CTGACCAGCG TGGAGTACGA GTTCTGGATC AAACACTTCA ATTTTGGTGT          1850

GTTTAAGAAA GACGAGTACG ACTGTTTCGA AGTTGACAAT CTGGAGTTTA          1900

CGGGTCTGAA GATTGGTCC  ATTCTGTACT ACAAGGCAGA GAAAGGCAAG          1950

TTTAAACCTT ACGTGGATCA CTTCATGAAA ATGAAAGTGG AGAACAAGAA          2000

ACTGGGTAAT AAGCCGCTGA CGAATCAGTT TAAGCTGATT CTGAACGGTG          2050

CGTACGGCAA ATTCGGCACC AAACAAAACA AGAAGAGAA  AGATTTGATC          2100

ATGGATAAGA ACGGTTTGCT GACCTTCACG GGTAGCGTCA CGGAATACGA          2150

GGGTAAAGAA TTCTATCGTC CGTATGCGAG CTTCGTTACT GCCTATGGTC          2200

GCCTGCAACT GTGGAACGCG ATTATCTACG CGGTTGGTGT GGAGAATTTT          2250

CTGTACTGCG ACACCGACAG CATCTATTGT AACCGTGAAG TTAACAGCCT          2300

CATTGAGGAT ATGAACGCCA TTGGTGAAAC CATCGATAAA ACGATTCTGG          2350

GTAAATGGGA CGTGGAGCAT GTCTTTGATA AGTTTAAGGT CCTGGGCCAG          2400

AAGAAGTACA TGTATCATGA TTGCAAAGAA GATAAAACGG ACCTGAAGTG          2450

TTGCGGTCTG CCGAGCGATG CCCGTAAGAT TATCATTGGT CAAGGTTTCG          2500

ACGAGTTTTA TCTGGGCAAA AATGTCGAAG GTAAGAAGCA ACGCAAAAAA          2550

GTGATCGGCG GTTGCCTGCT GCTGGACACC CTGTTTACGA TCAAGAAAAT          2600

CATGTTCTAA                                                      2610
```

SEQ ID NO: 6 - Pol6-44-X1 with His-tag/SpyCatcher + E585K of
SEQ ID NO: 2, which corresponds to E715K of SEQ ID NO: 6

```
MHHHHHHHHS GDYDIPTTEN LYFQGAMVDT LSGLSSEQGQ SGDMTIEEDS            50

ATHIKFSKRD EDGKELAGAT MELRDSSGKT ISTWISDGQV KDFYLYPGKY           100

TEVETAAPDG YEVATAITFT VNEQGQVTVN GKATKGDAHI GGSDKHTQYV           150

KEHSFNYDEY KKANFDKIEC LIFATESCTN YENDNTGARV YGWGLGVTRN           200

HNMIYGQNLN QFWEVCQNIF NDWYHDNKHT IKITKTKKGF PKRKYIKFPI           250

AVHNLGWDVE FLKYSLVENG FNYDKGLLKT VFSKGAPYQT VTDVEEPKTF           300

HIVQNNNIVY GCNVYMDKFF EVENKDGSTT EIGLCLDFFD SYKIITCAES           350

QFHNYVHDVD PMFYKMGEEY DYDTWRSPTH KQTTLELRYQ YNDIYMLREV           400

IEQFYIDGLC GGELPLTGMR TASSIAFNVL KKMTFGEEKT EEGYINYFEL           450

DKKTKFEFLR KRIEMESYTG GYTHANHKAV GKTINKIGCS LDINSAYPSQ           500

MAYKVFPYGK PVRKTWGRKP KTEKNEVYLI EVGFDFVEPK HEEYALDIFK           550

IGAVNSKALS PITGAVSGQE YFCTNIKDGK AIPVYKELKD TKLTTNYNVV           600

LTSVEYEFWI KHFNFGVFKK DEYDCFEVDN LEFTGLKIGS ILYYKAEKGK           650

FKPYVDHFMK MKVENKKLGN KPLTNQFKLI LNGAYGKFGT KQNKEEKDLI           700

MDKNGLLTFT GSVTKYEGKE FYRPYASFVT AYGRLQLWNA IIYAVGVENF           750

LYCDTDSIYC NREVNSLIED MNAIGETIDK TILGKWDVEH VFDKFKVLGQ           800

KKYMYHDCKE DKTDLKCCGL PSDARKIIIG QGFDEFYLGK NVEGKKQRKK           850

VIGGCLLLDT LFTIKKIMF*                                            869
```

-continued

SEQ ID NO: 7 - Pol6-44-X1 with His-tag/SpyCatcher + E585K+L731K
of SEQ ID NO: 2, which correspond to E715K+L861K of SEQ ID NO: 6

```
MHHHHHHHHS GDYDIPTTEN LYFQGAMVDT LSGLSSEQGQ SGDMTIEEDS          50

ATHIKFSKRD EDGKELAGAT MELRDSSGKT ISTWISDGQV KDFYLYPGKY          100

TFVETAAPDG YEVATAITFT VNEQGQVTVN GKATKGDAHI GGSDKHTQYV          150

KEHSFNYDEY KKANFDKIEC LIFATESCTN YENDNTGARV YGWGLGVTRN          200

HNMIYGQNLN QFWEVCQNIF NDWYHDNKHT IKITKTKKGF PKRKYIKFPI          250

AVHNLGWDVE FLKYSLVENG FNYDKGLLKT VFSKGAPYQT VTDVEEPKTF          300

HIVQNNNIVY GCNVYMDKFF EVENKDGSTT EIGLCLDFFD SYKIITCAES          350

QFHNYVHDVD PMFYKMGEEY DYDTWRSPTH KQTTLELRYQ YNDIYMLREV          400

IEQFYIDGLC GGELPLTGMR TASSIAFNVL KKMTFGEEKT EEGYINYFEL          450

DKKTKFEFLR KRIEMESYTG GYTHANHKAV GKTINKIGCS LDINSAYPSQ          500

MAYKVFPYGK PVRKTWGRKP KTEKNEVYLI EVGFDFVEPK HEEYALDIFK          550

IGAVNSKALS PITGAVSGQE YFCTNIKDGK AIPVYKELKD TKLTTNYNVV          600

LTSVEYEFWI KHFNFGVFKK DEYDCFEVDN LEFTGLKIGS ILYYKAEKGK          650

FKPYVDHFMK MKVENKKLGN KPLTNQFKLI LNGAYGKFGT KQNKEEKDLI          700

MDKNGLLTFT GSVTKYEGKE FYRPYASFVT AYGRLQLWNA IIYAVGVENF          750

LYCDTDSIYC NREVNSLIED MNAIGETIDK TILGKWDVEH VFDKFKVLGQ          800

KKYMYHDCKE DKTDLKCCGL PSDARKIIIG QGFDEFYLGK NVEGKKQRKK          850

VIGGCLLLDT KFTIKKIMF*                                          869
```

SEQ ID NO: 8 - Pol6-44-X1 with His-tag/SpyCatcher + E585K+M738K
of SEQ ID NO: 2, which correspond to E715K+M868K of SEQ ID NO: 6

```
MHHHHHHHHS GDYDIPTTEN LYFQGAMVDT LSGLSSEQGQ SGDMTIEEDS          50

ATHIKFSKRD EDGKELAGAT MELRDSSGKT ISTWISDGQV KDFYLYPGKY          100

TFVETAAPDG YEVATAITFT VNEQGQVTVN GKATKGDAHI GGSDKHTQYV          150

KEHSFNYDEY KKANFDKIEC LIFATESCTN YENDNTGARV YGWGLGVTRN          200

HNMIYGQNLN QFWEVCQNIF NDWYHDNKHT IKITKTKKGF PKRKYIKFPI          250

AVHNLGWDVE FLKYSLVENG FNYDKGLLKT VFSKGAPYQT VTDVEEPKTF          300

HIVQNNNIVY GCNVYMDKFF EVENKDGSTT EIGLCLDFFD SYKIITCAES          350

QFHNYVHDVD PMFYKMGEEY DYDTWRSPTH KQTTLELRYQ YNDIYMLREV          400

IEQFYIDGLC GGELPLTGMR TASSIAFNVL KKMTFGEEKT EEGYINYFEL          450

DKKTKFEFLR KRIEMESYTG GYTHANHKAV GKTINKIGCS LDINSAYPSQ          500

MAYKVFPYGK PVRKTWGRKP KTEKNEVYLI EVGFDFVEPK HEEYALDIFK          550

IGAVNSKALS PITGAVSGQE YFCTNIKDGK AIPVYKELKD TKLTTNYNVV          600

LTSVEYEFWI KHFNFGVFKK DEYDCFEVDN LEFTGLKIGS ILYYKAEKGK          650

FKPYVDHFMK MKVENKKLGN KPLTNQFKLI LNGAYGKFGT KQNKEEKDLI          700

MDKNGLLTFT GSVTKYEGKE FYRPYASFVT AYGRLQLWNA IIYAVGVENF          750

LYCDTDSIYC NREVNSLIED MNAIGETIDK TILGKWDVEH VFDKFKVLGQ          800

KKYMYHDCKE DKTDLKCCGL PSDARKIIIG QGFDEFYLGK NVEGKKQRKK          850

VIGGCLLLDT LFTIKKIKF*                                          869
```

-continued

SEQ ID NO: 9 - His 6 tag: HHHHHH

SEQ ID NO: 10 - SpyCatcher
SGDYDIPTTENLYFQGAMVDTLSGLSSEQGQSGDMTIEEDSATHIKFSKRDEDGKELAGATMELRDS

SGKTISTWISDGQVKDFYLYPGKYTFVETAAPDGYEVATAITFTVNEQGQVTVNGKATKGDAHI

SEQ ID NO: 11 - SpyTag: AHIVMVDAYKPTK

SEQ ID NOS 12 and 21 - Cy5-labelled fluorogenic DNA template
Cy5/AGA GTG ATA GTA TGA TTA TGT AGA TGT AGG ATT TGA TAT GTG AGT AGC CGA ATG AAA CCT T/iSpC3/TT GGT TTC ATT CGG SEQ ID NO: 13 - Black Hole Quencher® dye-labelled quencher
oligonucleotide
TTT TCA TAA TCA TAC TAT CAC TCT /3BHQ_2/

SEQ ID NO: 14 - Pol6-67 X2 (with His tag and T529M-S366A-
A547F-N545L-Y225L-D657R Y242A)
MHHHHHHHHS GGSDKHTQYV KEHSFNYDEY KKANFDKIEC LIFDTESCTN                    50

YENDNTGARV YGWGLGVTRN HNMIYGQNLN QFWEVCQNIF NDWYHDNKHT                   100

IKITKTKKGF PKRKYIKFPI AVHNLGWDVE FLKYSLVENG FNYDKGLLKT                   150

VFSKGAPYQT VTDVEEPKTF HIVQNNNIVY GCNVYMDKFF EVENKDGSTT                   200

EIGLCLDFFD SYKIITCAES QFHNLVHDVD PMFYKMGEEY DADTWRSPTH                   250

KQTTLELRYQ YNDIYMLREV IEQFYIDGLC GGELPLTGMR TASSIAFNVL                   300

KKMTFGEEKT EEGYINYFEL DKKTKFEFLR KRIEMESYTG GYTHANHKAV                   350

GKTINKIGCS LDINSAYPSQ MAYKVFPYGK PVRKTWGRKP KTEKNEVYLI                   400

EVGFDFVEPK HEEYALDIFK IGAVNSKALS PITGAVSGQE YFCTNIKDGK                   450

AIPVYKELKD TKLTTNYNVV LTSVEYEFWI KHFNFGVFKK DEYDCFEVDN                   500

LEFTGLKIGS ILYYKAEKGK FKPYVDHFMK MKVENKKLGN KPLTLQFKLI                   550

LNGAYGKFGT KQNKEEKDLI MDKNGLLTFT GSVTEYEGKE FYRPYASFVT                   600

AYGRLQLWNA IIYAVGVENF LYCDTDSIYC NREVNSLIED MNAIGETIDK                   650

TILGKWRVEH VFDKFKVLGQ KKYMYHDCKE DKTDLKCCGL PSDARKIIIG                   700

QGFDEFYLGK NVEGKKQRKK VIGGCLLLDT LFTIKKIMF*                              739

SEQ ID NOS 15 and 22 -- Fluorescent Hairpin DNA template
/5deSBioTEG/ACTGCTGATCTGTTCCTGAATCGACTACTACTATCATCATACCACCTCAGCTGCACG /iFluorT/T/iSpC3/AAGTGCAGCTGAGGTGG SEQ ID NO: 16 -- Chase Template
AGAGTGATAGTATGATTATGTATGTGAGTAGTCCACTGAAACCTTTGGTTTCAGTGGA/3ddC/

SEQ ID NOS 17 and 22 - LongHP-Cy5-ExoR
/5Cy5/ATCTCTTCAACTCGACTTATGTTCTACTGCTGATCTGTTCCTGAATCGACT ACTACTATCATCATACCACCTCAGCTGCACGT/iSpC3/AAGTGCAGCTGAGGTGG SEQ ID NO: 18 - Quencher Primer
TTTGATTCAGGAACAGATCAGCAGTAGAACATAAGTCGAGTTGAAGAGAT/3BHQ_2/

---

The invention claimed is:

1. A method for preparing a polymerase-template complex, the method comprising incubating a polynucleotide template with a polymerase in a solution comprising one or more nucleotides for a period of time sufficient to allow the polymerase and the polynucleotide template to form the polymerase-template complex; wherein the polymerase is a variant of a Pol6 polymerase comprising at least three amino acid modifications, wherein the at least three amino acid modifications are selected from T529M, S366A, A547F, N545L, Y225L, Y242A, and D657R, wherein the Pol6 polymerase has at least 95% identity to that of SEQ ID NO: 2; and wherein the incubation is performed at a temperature of at least 30° C.

2. The method of claim 1, wherein the variant of the Pol6 polymerase further comprises at least one amino acid modification selected from the group consisting of G438K, E565K, E585K, L731K, and M738K.

3. The method of claim 1, wherein the incubation temperature ranges from about 35° C. to about 45° C.

4. The method of claim 1, wherein the incubation temperature is about 36° C.

5. The method of claim 1, wherein the polymerase is present in a molar excess concentration relative to the concentration of the polynucleotide template.

6. The method of claim 1, wherein the solution further comprises a potassium salt.

7. The method of claim 6, wherein the potassium salt is potassium citrate.

8. The method of claim 1, wherein the solution further comprises at least one of a buffer, a surfactant, and a preservative.

9. A method for preparing a polymerase-template complex, the method comprising incubating a polynucleotide template with a polymerase in a solution for a period of time sufficient to allow the polymerase and the polynucleotide template to form the polymerase-template complex, wherein the incubation is performed at a temperature of at least 30° C.; wherein the solution comprises (i) a potassium salt, and (ii) one or more nucleotides; and wherein the polymerase is a variant of a Pol6 polymerase comprising at least one amino acid modification selected from the group consisting of T529M, S366A, A547F, N545L, Y225L, Y242A, and D657R; and wherein the Pol6 polymerase has at least 95% identity to that of SEQ ID NO: 2.

10. The method of claim 9, wherein the variant of the Pol6 polymerase comprises at least two amino acid modifications selected from the group consisting of T529M, S366A, A547F, N545L, Y225L, Y242A, and D657R.

11. The method of claim 9, wherein the variant of the Pol6 polymerase further comprises at least one amino acid modification selected from the group consisting of G438K, E565K, E585K, L731K, and M738K.

12. The method of claim 9, wherein the potassium salt is potassium citrate.

13. A method of sequencing a DNA template, the method comprising:
   (a) forming a primed DNA template by annealing a primer to the DNA template;
   (b) forming a polymerase-template complex according to the method of claim 1 or claim 10;
   (c) forming a nanopore-sequencing complex comprising:
      (c1) a nanopore deposited in a membrane, wherein the nanopore is positioned adjacent to or in proximity to a sensing electrode of a biochip; and
      (c2) the polymerase-template complex, wherein the DNA polymerase of the polymerase-template complex is linked to the nanopore;
   (d) providing tagged nucleotides to the nanopore sequencing complex to initiate a primer extension reaction that polymerizes the tagged nucleotides into a nucleic acid complementary to the DNA template;

(e) detecting tags associated with tagged nucleotides incorporated into the complementary strand by measuring a current flowing through the nanopore; and (f) deriving the sequence of the DNA template from the measured current flowing through the nanopore.

14. The method of claim 13, wherein the forming of the polymerase-template complex occurs at a temperature ranging from about 35° C. to about 45° C.

15. The method of claim 13, wherein the forming of the polymerase-template complex occurs in a solution comprising a potassium salt; and wherein the variant of the Pol6 polymerase comprises at least three amino acid modifications, wherein the at least three amino acid modifications are selected from the group consisting of T529M, S366A, A547F, N545L, Y225L, Y242A, and D657R.

16. The method of claim 13, wherein the variant of the Pol6 polymerase comprises the amino acid modifications T529M, S366A, A547F, N545L, Y225L, Y242A, and D657R.

17. The method of claim 16, wherein the variant of the Pol6 polymerase further comprises at least one amino acid modification selected from the group consisting of G438K, E565K, E585K, L731K, and M738K.

18. The method of claim 1, wherein the variant of the Pol6 polymerase comprises at least the amino acid modifications T529M, S366A, A547F, N545L, Y225L, Y242A, and D657R.

19. The method of claim 9, wherein the variant of the Pol6 polymerase comprises at least the amino acid modifications T529M, S366A, A547F, N545L, Y225L, Y242A, and D657R.

20. The method of claim 1, wherein the Pol6 polymerase has at least 98% identity to that of SEQ ID NO: 2.

21. The method of claim 1, wherein the Pol6 polymerase has at least 99% identity to that of SEQ ID NO: 2.

* * * * *